(12) United States Patent
Matsushita et al.

(10) Patent No.: US 11,701,128 B2
(45) Date of Patent: Jul. 18, 2023

(54) HEMOSTATIC DEVICE

(71) Applicant: TERUMO KABUSHIKI KAISHA, Tokyo (JP)

(72) Inventors: Shuhei Matsushita, Hadano (JP); Hiroshi Yagi, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/993,607

(22) Filed: Aug. 14, 2020

(65) Prior Publication Data
US 2020/0367907 A1  Nov. 26, 2020

Related U.S. Application Data

(60) Division of application No. 15/908,882, filed on Mar. 1, 2018, now abandoned, which is a continuation of
(Continued)

(30) Foreign Application Priority Data

Sep. 3, 2015 (JP) .................. 2015-174197
Sep. 3, 2015 (JP) .................. 2015-174198
Sep. 3, 2015 (JP) .................. 2015-174201

(51) Int. Cl.
*A61B 17/135* (2006.01)
*A61B 17/132* (2006.01)
*A61B 17/00* (2006.01)

(52) U.S. Cl.
CPC ........ *A61B 17/135* (2013.01); *A61B 17/1325* (2013.01); *A61B 2017/00557* (2013.01)

(58) Field of Classification Search
CPC ... A61B 17/12; A61B 17/132; A61B 17/1322; A61B 17/1325; A61B 17/1327;
(Continued)

(56) References Cited

U.S. PATENT DOCUMENTS 37,156 A    12/1862 Dunton et al.
2,245,998 A  6/1941 Herbert
(Continued)

FOREIGN PATENT DOCUMENTS

CN    201977871 U    9/2011
CN    204207803 U    3/2015
(Continued)

OTHER PUBLICATIONS

U.S. Appl. No. 15/908,965, filed Jan. 3, 2018, Matsuhita, Shuhei, et al.
(Continued)

*Primary Examiner* — Kankindi Rwego
(74) *Attorney, Agent, or Firm* — Buchanan Ingersoll & Rooney PC

(57) ABSTRACT

A hemostatic device includes a flexible band allowed to be wrapped around a wrist in which a radial artery and an ulnar artery run, a hook and loop fastener that secures the band in a state of being wrapped around the wrist, an inflatable portion connected to the band and allowed to press a puncture site of the radial artery by being inflated in response to injection of a fluid, and a pressing member disposed at a different position from a position of the inflatable portion in a longitudinal direction of the band and allowed to press the ulnar artery. Further, a length of the pressing member along the longitudinal direction of the band is shorter than a width of the pressing member along a direction orthogonal to the longitudinal direction of the band.

11 Claims, 25 Drawing Sheets

Related U.S. Application Data application No. PCT/JP2016/075912, filed on Sep. 2, 2016.

(58) Field of Classification Search
CPC ...... A61B 17/1355; A61B 2017/00557; A61B 2017/00907; A61B 2017/00955; A61B 2017/12004; A61B 5/021; A61B 5/02141; A61B 5/022; A61B 2017/00243; A61B 2017/00778; A61F 5/01; A61F 5/0118; A61F 5/05816; A61F 5/05866; A61F 5/05875; A61F 5/012; A61F 5/013; A61F 5/30; A61F 2007/0001; A61F 2007/0029; A61F 2007/0036; A61F 2007/0037; A61F 2007/0038; A61F 5/32; A61F 5/34; A61H 9/0078; A61H 9/0085; A61H 9/0092; A61H 1/006
USPC ................................ 606/201, 202, 203, 204
See application file for complete search history.

(56) References Cited

U.S. PATENT DOCUMENTS

| | | | |
|---|---|---|---|
| 3,905,361 | A | 9/1975 | Hewson et al. |
| 4,469,099 | A | 9/1984 | McEwen |
| 4,760,846 | A | 8/1988 | Mers et al. |
| 4,920,971 | A | 5/1990 | Blessinger |
| 4,981,133 | A | 1/1991 | Rollband |
| 5,152,302 | A | 10/1992 | Fareed |
| 5,295,951 | A | 3/1994 | Fareed |
| 5,307,811 | A | 5/1994 | Sigwart et al. |
| 5,433,724 | A | 7/1995 | Kawasaki et al. |
| 5,464,420 | A | 11/1995 | Hori et al. |
| 5,496,262 | A | 3/1996 | Johnson, Jr. et al. |
| 5,514,155 | A | 5/1996 | Daneshvar |
| 5,569,297 | A | 10/1996 | Makower et al. |
| 5,643,315 | A | 7/1997 | Daneshvar |
| 5,660,182 | A | 8/1997 | Kuroshaki et al. |
| 5,728,120 | A | 3/1998 | Shani et al. |
| 5,779,657 | A | 7/1998 | Daneshvar |
| 5,792,173 | A | 8/1998 | Breen et al. |
| 5,840,037 | A | 11/1998 | Tochikubo et al. |
| 6,007,562 | A | 12/1999 | Harren et al. |
| 6,231,517 | B1 | 5/2001 | Forstner |
| 6,336,901 | B1 | 1/2002 | Itonaga et al. |
| 6,361,496 | B1 | 3/2002 | Zikorus et al. |
| 6,527,727 | B2 | 3/2003 | Itonaga et al. |
| 6,694,821 | B2 | 2/2004 | Yamakoshi et al. |
| 6,827,727 | B2 | 12/2004 | Stalemark et al. |
| 7,498,477 | B2 | 3/2009 | Wada et al. |
| 7,927,295 | B2 | 4/2011 | Bates et al. |
| 8,034,009 | B2 | 10/2011 | Bates et al. |
| 8,481,803 | B2 | 7/2013 | Wada et al. |
| 8,481,805 | B2 | 7/2013 | Wada et al. |
| 8,524,974 | B2 | 9/2013 | Wada et al. |
| 8,759,603 | B2 | 6/2014 | Wada et al. |
| 9,895,155 | B2 | 2/2018 | Wada et al. |
| 9,936,959 | B2 | 4/2018 | Wada et al. |
| 9,949,741 | B2 | 4/2018 | Wada et al. |
| 10,219,809 | B2 | 3/2019 | Wada et al. |
| 2002/0147404 | A1 | 10/2002 | Kato et al. |
| 2002/0170359 | A1 | 11/2002 | Yamakoshi et al. |
| 2003/0199922 | A1 | 10/2003 | Buckman |
| 2004/0049214 | A1 | 3/2004 | Akerfeldt |
| 2004/0068290 | A1 | 4/2004 | Bates et al. |
| 2004/0098035 | A1 | 5/2004 | Wada et al. |
| 2004/0122469 | A1 | 6/2004 | Akerfeldt et al. |
| 2013/0245674 | A1 | 9/2013 | Wada et al. |
| 2013/0282048 | A1 | 10/2013 | Wada et al. |
| 2013/0289613 | A1 | 10/2013 | Wada et al. |
| 2013/0304111 | A1 | 11/2013 | Zhadkevich |
| 2015/0018869 | A1 | 1/2015 | Benz et al. |
| 2015/0335334 | A1 | 11/2015 | Pancholy et al. |
| 2016/0338709 | A1 | 11/2016 | Wada et al. |
| 2018/0000491 | A1 | 1/2018 | Wada et al. |
| 2018/0014833 | A1 | 1/2018 | Wada et al. |
| 2018/0250017 | A1 | 9/2018 | Matsushita |

FOREIGN PATENT DOCUMENTS

| | | |
|---|---|---|
| EP | 0601756 A1 | 6/1994 |
| EP | 1382306 A2 | 1/2004 |
| EP | 2070483 A2 | 6/2009 |
| EP | 2245998 A1 | 11/2010 |
| EP | 2662034 A1 | 11/2013 |
| JP | S5633526 Y2 | 8/1981 |
| JP | H01265941 A | 10/1989 |
| JP | H05137730 A | 6/1993 |
| JP | H05305093 A | 11/1993 |
| JP | H0779983 A | 3/1995 |
| JP | H0871077 A | 3/1996 |
| JP | H08140990 A | 6/1996 |
| JP | 3031486 U | 11/1996 |
| JP | H1057386 A | 3/1998 |
| JP | H11347005 A | 12/1999 |
| JP | 2000515773 A | 11/2000 |
| JP | 2004154413 A | 6/2004 |
| JP | 2005521464 A | 7/2005 |
| JP | 2007021112 A | 2/2007 |
| JP | 3136041 U | 9/2007 |
| JP | 2015066028 A | 4/2015 |
| JP | 2018522706 A | 8/2018 |
| WO | 9702783 A1 | 1/1997 |
| WO | 9717900 A1 | 5/1997 |
| WO | 2012126154 A1 | 9/2012 |
| WO | 2016095038 A1 | 6/2016 |
| WO | 2017023499 A1 | 2/2017 |

OTHER PUBLICATIONS

Chinese Search Report dated Mar. 26, 2020, corresponding to Chinese Application 201680051211.5 with English translation, 26 pages.

English translation of Written Opinion of the International Searching Authority dated Jan. 10, 2017, in corresponding International Application No. PCT/JP2016/075912 (8 pages).

International Search Report (PCT/ISA/210) dated Jan. 10, 2017, by the Japanese Patent Office as the International Searching Authority for International Application No. PCT/JP2016/075912.

Office Action (Notice of Reasons for Refusal) dated May 21, 2019, by the Japanese Patent Office in corresponding Japanese Patent Application No. 2015-174197 and an English Translation of the Office Action. (7 pages).

Office Action (Notice of Reasons for Refusal) dated May 28, 2019, by the Japanese Patent Office in corresponding Japanese Patent Application No. 2015-174198 and an English Translation of the Office Action. (7 pages).

The extended European Search Report dated Aug. 13, 2019, by the European Patent Office in corresponding European Patent Application No. 16842036.2-1122. (33 pages).

The partial supplementary European Search Report dated May 6, 2019, by the European Patent Office in corresponding European Patent Application No. 16842036.2-1122. (16 pages).

Written Opinion (PCT/ISA/237) dated Jan. 10, 2017, by the Japanese Patent Office as the International Searching Authority for International Application No. PCT/JP2016/075912.

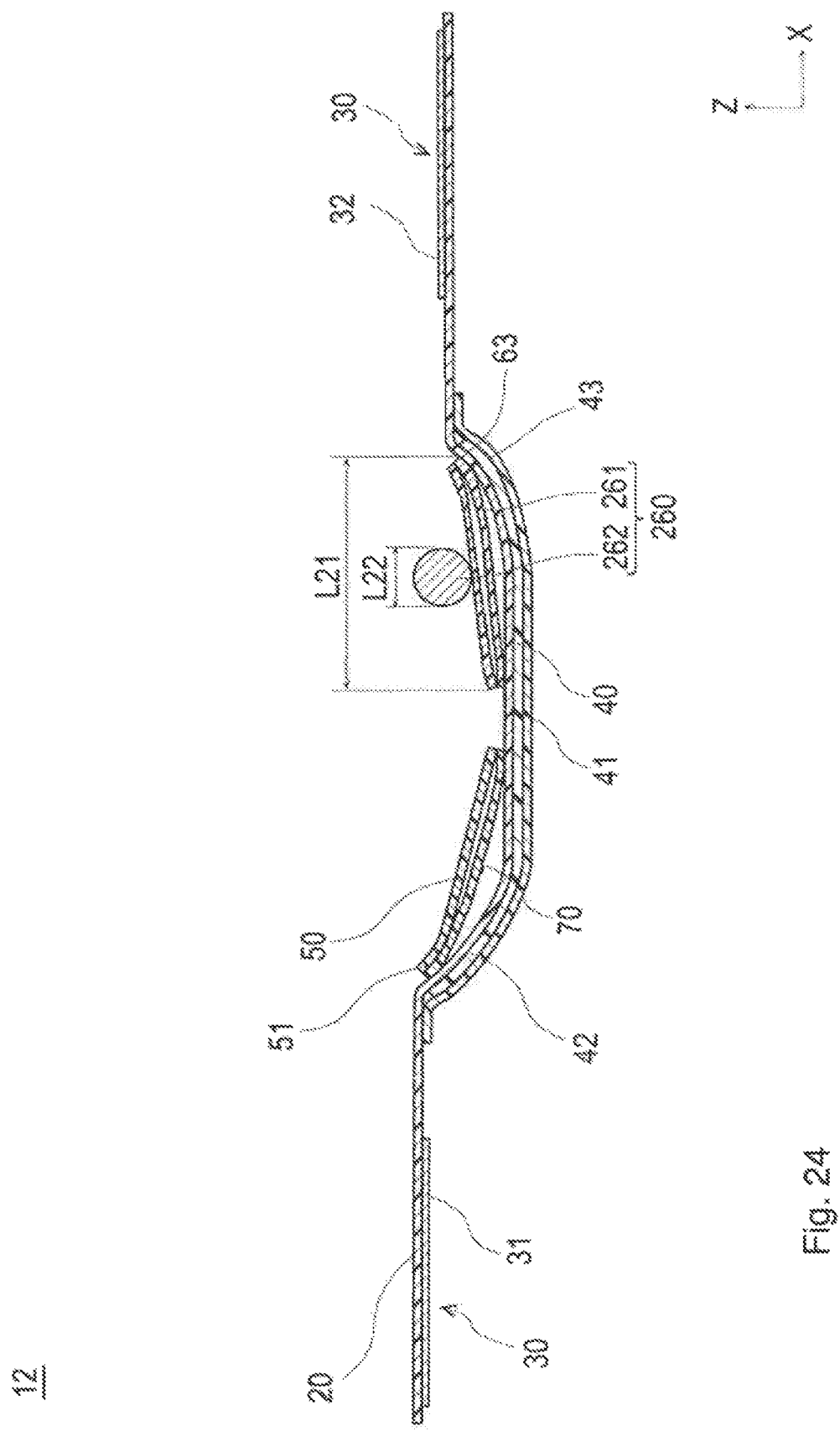

HEMOSTATIC DEVICE

CROSS-REFERENCES TO RELATED APPLICATIONS

This application is a divisional of U.S. application Ser. No. 15/908,882 filed on Mar. 1, 2018, which is a continuation of International Application No. PCT/JP2016/075912 filed on Sep. 2, 2016, which claims priority to Japanese Application No. 2015-174197 filed on Sep. 3, 2015, Japanese Application No. 2015-174198 filed on Sep. 3, 2015 and Japanese Application No. 2015-174201 filed on Sep. 3, 2015, the entire content of each of which is incorporated herein by reference.

TECHNICAL FIELD

The present invention generally relates to a hemostatic device for performing hemostasis by pressing a punctured site.

BACKGROUND ART

Recently, treatment/examination, etc. have been percutaneously performed by puncturing a blood vessel such as a radial artery, etc. of an arm, introducing an introducer sheath to a puncture site, and inserting a catheter, etc. into a lesion of the blood vessel, etc. through a lumen of the introducer sheath. When such a procedure is performed, it is necessary to perform hemostasis at the puncture site after withdrawing the introducer sheath. To perform hemostasis, there has been a known hemostatic device including a band for wrapping around the puncture site of the arm, a securing portion that secures the band in a state of being wrapping around the puncture site, and an inflatable portion that can press the puncture site by inflating in response to injection of a fluid. An example of such a device is disclosed in Japanese Application No. 2004-154413. This hemostatic device performs hemostasis by directly applying a pressing force acting from the inflatable portion to the puncture site.

SUMMARY OF THE INVENTION

A radial artery and an ulnar artery branch from a brachial artery near an elbow and are connected to each other in a palm. For this reason, when only the radial artery is pressed (compressed) for a long time, blood may hardly flow to the radial artery, and a blood flow rate of the ulnar artery may excessively increase. As a result, a blood flow rate of the radial artery decreases, so that the blood vessel occludes or the amount of platelets, etc. decreases, thereby requiring a long time for hemostasis at the puncture site. For this reason, for example, it is known to press the ulnar artery to reopen the occluded radial artery after performing hemostasis at the puncture site of the radial artery. An example of this is described in the following non-patent document—Ivo Bernat, M D et al., "Efficacy and Safety of Transient Ulnar Artery Compression to Recanalize Acute Radial Artery Occlusion After Transradial Catheterization", American Journal of Cardiology (U.S.), 2011, 107(11), p. 1698-1701.

In response to such a problem, for example, when a pressing member for pressing the ulnar artery is further provided in the above-described hemostatic device, it is considered that an excessive increase in blood flow flowing to the ulnar artery may be prevented by pressing the ulnar artery, thereby suppressing a decrease in blood flow rate of the radial artery at the time of pressing the radial artery.

However, in the hemostatic device configured as described above, when the pressing member presses a wide range along a circumferential direction of the arm, a tendon, a nerve, etc. around the ulnar artery are also pressed, which causes numbness or pain.

The hemostatic device disclosed here is configured to enhance the hemostatic effect by suppressing a decrease in blood flow rate of a radial artery, and reducing numbness or pain caused by pressing an ulnar artery.

A hemostatic device disclosed here includes: a flexible band configured to be wrapped around an arm in which a radial artery and an ulnar artery are located, with the flexible band possessing a longitudinal extent that extends in a longitudinal direction; a securing portion that secures the flexible band on the arm while the flexible band is wrapped around the arm in a wrapped state; an inflatable member connected to the flexible band and expandable upon being inflated in response to introducing fluid into an interior of the inflatable member to press a part of the radial artery to be subjected to hemostasis, with the inflatable member possessing oppositely facing surfaces; and a pressing member disposed at a position spaced from a position of the inflatable member in the longitudinal direction of the flexible band to press the ulnar artery, with the pressing member possessing oppositely facing surfaces. The pressing member possessing a length along the longitudinal direction of the flexible band that is shorter than a width of the pressing member along a direction orthogonal to the longitudinal direction of the flexible band.

According to the hemostatic device configured as described above, it is possible to enhance hemostatic effect by suppressing a decrease in blood flow rate of a radial artery. In addition, the length of the pressing member along the longitudinal direction of the band is shorter than the width of the pressing member along the direction orthogonal to the longitudinal direction of the band. For this reason, a part in which the pressing member comes into contact with the arm at the time of mounting the hemostatic device on the arm has a shape extending along running of the ulnar artery. In this way, it is possible to narrow a range of a part other than the ulnar artery (a tendon, a nerve, etc.) pressed by the pressing member while favorably pressing the ulnar artery by the pressing member. As a result, it is possible to reduce numbness or pain caused by pressing the ulnar artery.

The hemostatic device can also include a plate that is more rigid than the flexible band and that is mounted on the flexible band so that the plate and the flexible band move together as a unit. The plate includes an inner surface that faces toward the arm when the flexible band is wrapped around the arm in the wrapped state. The inner surface of the plate includes a center inner surface portion, a first curved inner surface portion and a second curved inner surface portion, with the center inner surface portion being positioned between the first and second inner surface portions along the longitudinal direction of the flexible band. The inner surface of the center portion may have a radius of curvature greater than the radius of curvature of the first and second curved inner surface portions.

According to another aspect, a hemostatic device comprises: a flexible band configured to be wrapped around an arm in which a radial artery and an ulnar artery are located, wherein the flexible band possesses a longitudinal extent that extends in a longitudinal direction; a securing portion that secures the flexible band on the arm while the flexible band is wrapped around the arm in a wrapped state; a support plate held by the flexible band and made of a material more rigid than the material from which the flexible band is made; and an inflatable member connected to the flexible band and expandable upon being inflated in response to introducing fluid into an interior of the inflatable member to press a part of the radial artery to be subjected to hemostasis. A pressing member is disposed at a position spaced from a position of the inflatable portion in the longitudinal direction of the flexible band and configured to press the ulnar artery, and the inflatable member possesses a first surface disposed on a side that will face the arm when the flexible band is in the wrapper state and a second surface disposed on a side facing the band. The pressing member includes a third surface disposed on a side that will face the arm when the flexible band is in the wrapper state and a fourth surface disposed on a side facing the band. The length of a perpendicular line from the support plate to the first surface is longer than a length of a perpendicular line from the support plate to the third surface when the inflatable portion is inflated in a state in which at least a part of the second surface of the inflatable portion and at least a part of the fourth surface of the pressing member are in contact with a portion of the band in which the support plate is disposed.

In accordance with another aspect, a hemostatic device comprises: a flexible band configured to be wrapped around an arm in which a radial artery and an ulnar artery are located, wherein the flexible band possesses a longitudinal extent that extends in a longitudinal direction; a securing portion that secures the flexible band on the arm while the flexible band is in a state of being wrapped around the arm; an inflatable member connected to the band and expandable upon being inflated in response to introducing fluid into an interior of the inflatable portion to press a part of the radial artery to be subjected to hemostasis, wherein the inflatable member possesses oppositely facing surfaces; and a pressing member disposed at a position spaced from a position of the inflatable portion in the longitudinal direction of the band to press the ulnar artery, with the pressing member possessing oppositely facing surfaces. The pressing member includes a main body and a projection disposed on the main body and protruding with respect to the main body.

BRIEF DESCRIPTION OF THE DRAWINGS

FIG. 24 is a cross-sectional view corresponding to FIG. 18, as a cross-sectional view illustrating a hemostatic device according to Modification 2 of the third embodiment.

DETAILED DESCRIPTION

Figure 1:
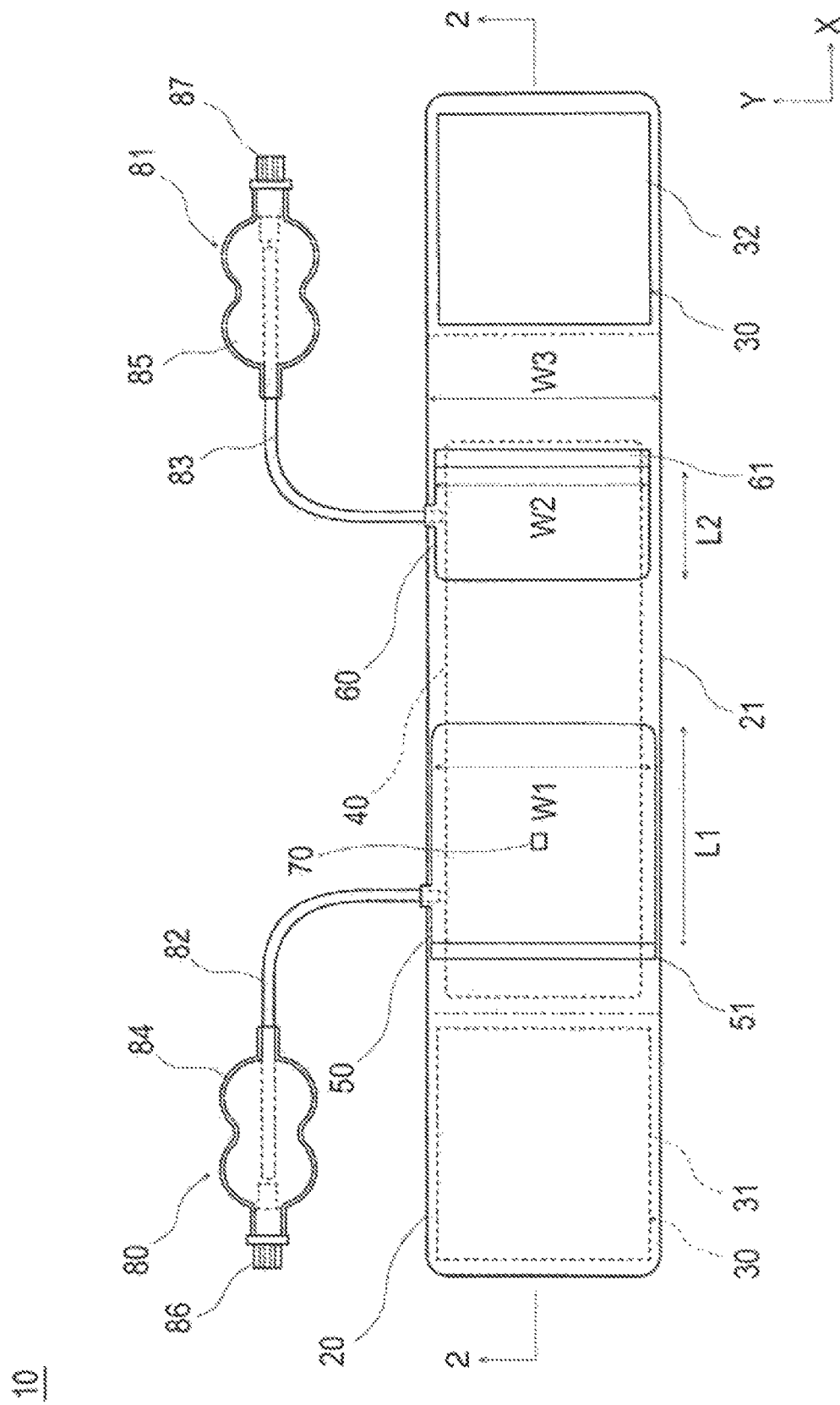
FIG. 1 is a plan view of a hemostatic device according to a first embodiment viewed from an inner surface side.

Hereinafter, embodiments of the hemostatic device, representing examples of the inventive hemostatic device disclosed here, will be described with reference to the accompanying drawings. The description below does not restrict a technical scope or a meaning of terms described in claims. In addition, a ratio of dimensions in the drawings is exaggerated for convenience of description and illustration, and may be different from an actual ratio.

First Embodiment

Figure 4:
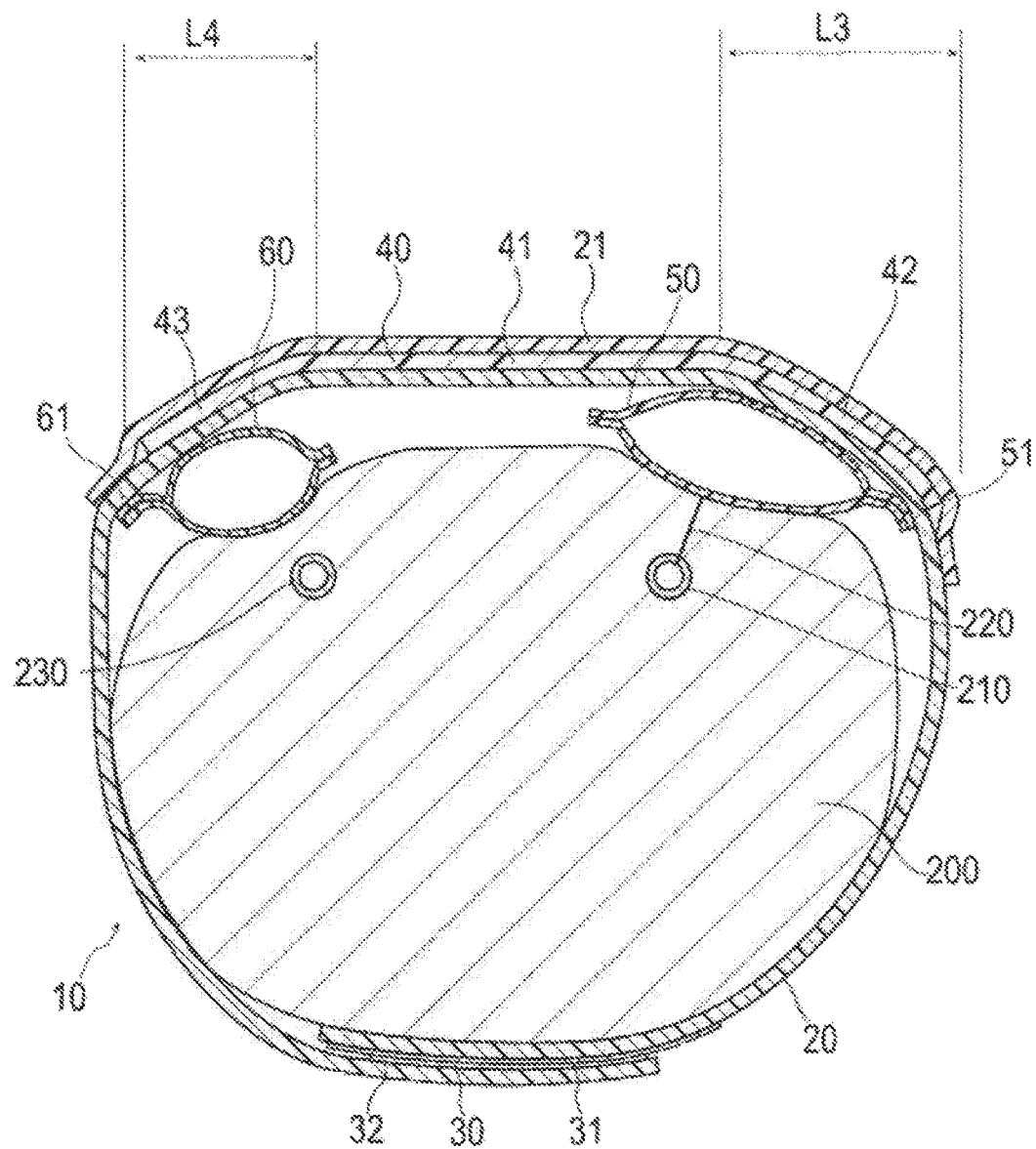
FIG. 4 is a cross-sectional view taken along the section line 4-4 of FIG. 3.

As illustrated in FIG. 4, a hemostatic device 10 according to a first embodiment is used to perform hemostasis at a puncture site 220 after withdrawing an introducer sheath indwelled in the puncture site 220 (corresponding to a part to be subjected to hemostasis) formed in a radial artery 210 of a wrist 200 (corresponding to an arm) to insert a catheter, etc. performing treatment/examination, etc. into a blood vessel.

Figure 2:
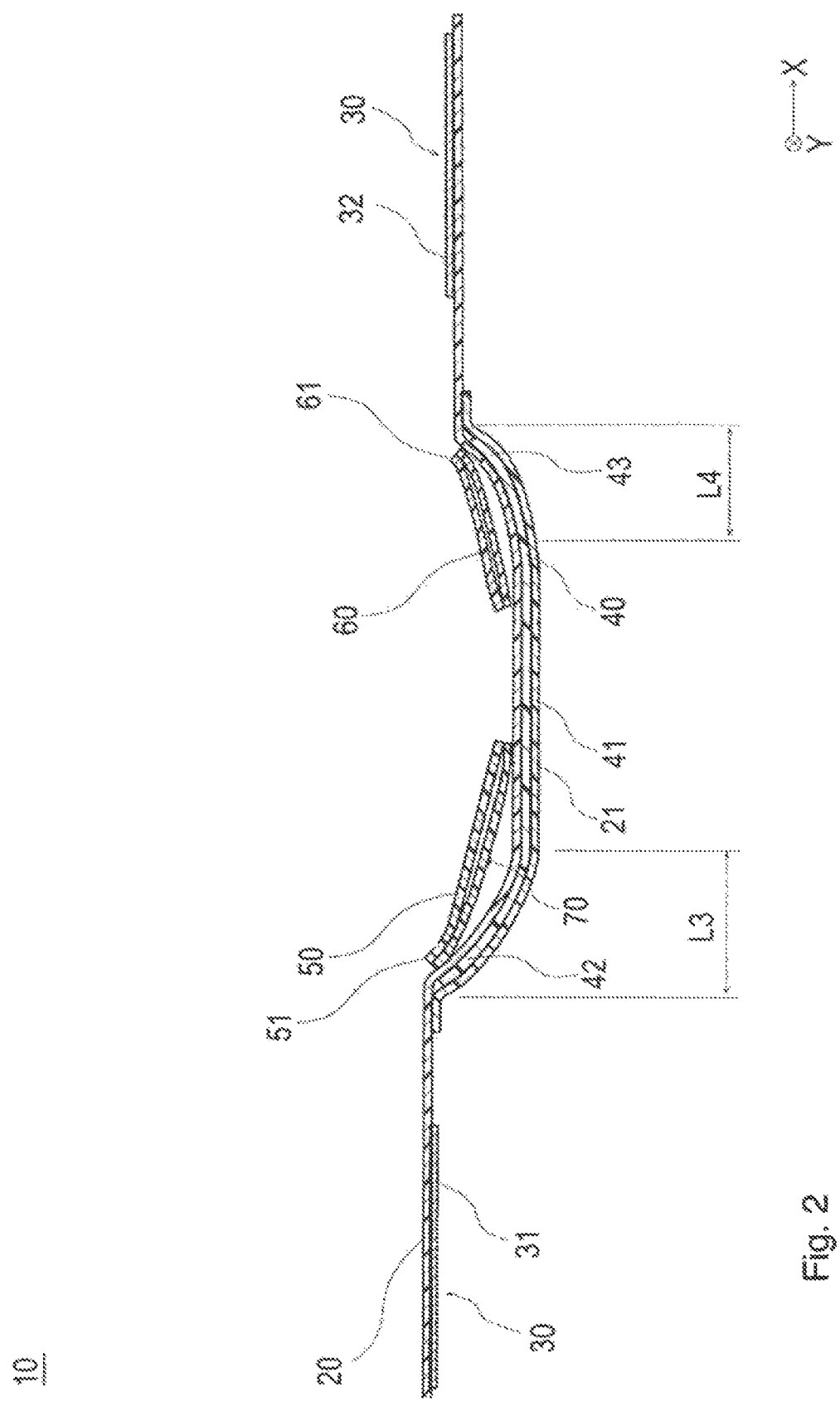
FIG. 2 is a cross-sectional view taken along the section line 2-2 of FIG. 1.

As illustrated in FIG. 1 and FIG. 2, the hemostatic device 10 includes a band 20 for wrapping around the wrist 200, a hook and loop fastener 30 (corresponding to a securing portion) for securing the band 20 while the band is in a wrapped state in which the band is wrapped around the wrist 200, a plate 40, a first inflatable portion 50 (corresponding to an inflatable portion or inflatable member/element), a second inflatable portion 60 (corresponding to a pressing member), a marker 70, a first injection portion 80, and a second injection portion 81.

In this specification, a side (mounting surface side) of the band 20 facing a body surface of the wrist 200 is referred to as an "inner surface side", and an opposite side of the band 20 is referred to as an "outer surface side" when the band 20 is wrapped around the wrist 200.

In addition, in the drawings, a longitudinal direction of the band 20 is indicated as an arrow X, and a direction orthogonal to the longitudinal direction of the band 20 is indicated as an arrow Y.

The band 20 may be a flexible band-shaped member possessing a longitudinal extent that extends in the longitudinal direction. As illustrated in FIG. 4, the band 20 is wrapped around an outer periphery of the wrist 200 substantially once. As illustrated in FIG. 2, a curved plate holding portion 21 that holds the curved plate 40 is formed at a central portion of the band 20 (central portion in the longitudinal direction X of the band 20). The curved plate holding portion 21 may be doubled by separate band-shaped members joined to an outer surface side (or inner surface side) using a method such as fusing (heat-fusing, high-frequency fusing, ultrasonic fusing, etc.), adhesion (adhesion by an adhesive or a solvent), etc. and holds the curved plate 40 positioned in a gap between the two separate band-shaped members.

Figure 3:
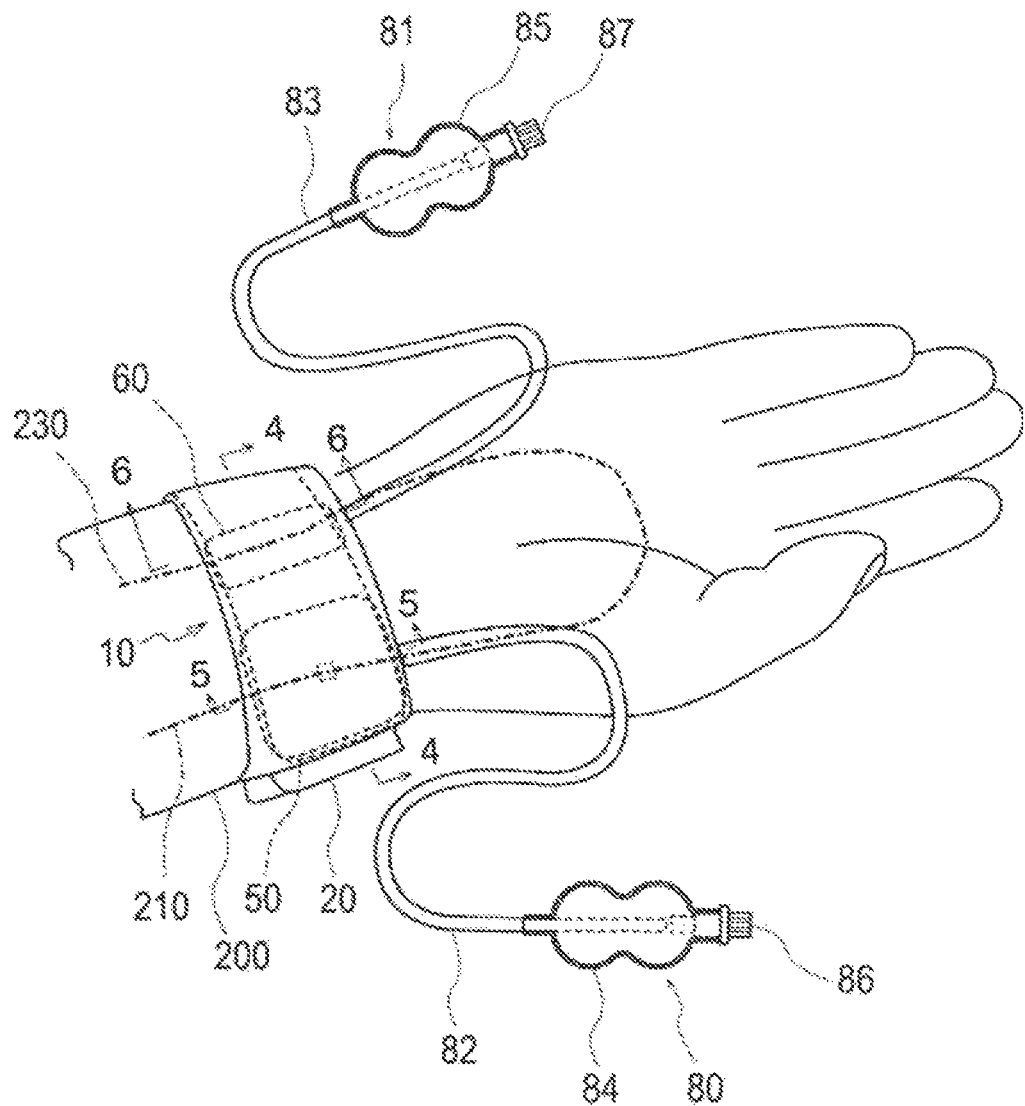
FIG. 3 is a perspective view illustrating a state of mounting the hemostatic device according to the first embodiment.

A male side (or a female side) 31 of the hook and loop fastener 30 generally referred to as Magic Tape (registered trademark), etc. may be disposed on the outer surface side of the band 20 near a left end of FIG. 1, and a female side (or a male side) 32 of the hook and loop fastener 30 may be disposed on the inner surface side of the band 20 near a right end of FIG. 1. As illustrated in FIG. 3 and FIG. 4, the band 20 may be wrapped around the wrist 200, and the male side 31 and the female side 32 are joined together, thereby mounting the band 20 on the wrist 200. The means for securing the band 20 to the wrist 200 in a wrapped state is not limited to the hook and loop fastener 30. For example, the means for securing may correspond to a snap, a button, a clip, or a frame member passing an end portion of the band 20.

A constituent material forming the band 20 is not particularly limited as long as the material has flexibility, and examples of the material for forming the band 20 include polyvinyl chloride, polyolefins such as polyethylene, polypropylene, polybutadiene and ethylene-vinyl acetate copolymers (EVA), polyesters such as polyethylene terephthalate (PET) and polybutylene terephthalate (PBT), polyvinylidene chloride, silicone, polyurethane, various thermoplastic elastomers such as polyamide elastomers, polyurethane elastomers and polyester elastomers, and an arbitrary combination of the above (blend resin, polymer alloy, laminate, etc.).

The band 20 is preferably substantially transparent. However, the band 20 may not be transparent, and may be translucent or colored transparent. In this way, the puncture site 220 may be visually recognized from the outer surface side, and the marker 70 described below may be relatively easily positioned in the puncture site 220.

As illustrated in FIG. 2, the plate 40 may be a curved plate 40 held in the band 20 by being inserted into or positioned in the doubly formed curved plate holding portion 21 of the band 20. At least a portion of the curved plate 40 may have a shape curved toward the inner surface side (outer surface side). The plate 40 in the illustrated example includes an inner surface on the side of the inflatable members 50, 60, and the plate 40 is curved so that portions of the inner surface of the plate are curved. The curved plate 40 may be made of a more rigid material than the material of the band 20 (the plate 40 is more rigid than the flexible band 20) and may maintain a substantially constant shape.

The curved plate 40 may have a shape elongated in the longitudinal direction (a direction of an arrow X) of the band 20. A central portion 41 of the curved plate 40 in the longitudinal direction may have a flat plate shape almost without being curved, and a first curved portion 42 (left side of FIG. 2) and a second curved portion 43 (right side of FIG. 2) curved toward an inner peripheral side and along the longitudinal direction of the band 20 (a circumferential direction of the wrist 200) are formed at both sides of the central portion 41, respectively. FIGS. 2 and 4 show that the first curved portion 42 possesses a radius of curvature smaller than the inner surface of central portion 41. Additionally, FIGS. 2 and 4 show that the first curved portion 42 possesses a curvature (curvature is a reciprocal of a radius of curvature) greater than the curvature of the inner surface of central portion 41. FIGS. 2 and 4 also illustrate that the second curved portion 43 possesses a radius of curvature smaller than the inner surface of central portion 41, and that the second curved portion 43 possesses a curvature greater than the curvature of the inner surface of the central portion 41.

A constituent material forming the curved plate 40 is not particularly limited as long as the puncture site 220 can be visually recognized. Examples of the material include acrylic resins, polyvinyl chloride (particularly rigid polyvinyl chloride), polyolefins such as polyethylene, polypropylene and polybutadiene, polystyrene, poly(4-methyl pentene-1), polycarbonates, ABS resins, polymethyl methacrylate (PMMA), polyacetals, polyarylates, polyacrylonitriles, polyvinylidene fluorides, ionomers, acrylonitrile-butadiene-styrene copolymers, polyesters such as polyethylene terephthalate (PET) and polybutylene terephthalate (PBT), butadiene-styrene copolymers, aromatic or aliphatic polyamides, and fluorocarbon resins such as polytetrafluoroethylene.

Similarly to the band 20, the curved plate 40 is preferably substantially transparent. However, the curved plate 40 may not be transparent, and may be translucent or colored transparent. In this way, the puncture site 220 may be reliably visually recognized from the outer surface side, and the marker 70 described below may be relatively easily positioned in the puncture site 220. The curved plate 40 may not have a non-curved part such as the central portion 41, that is, may be curved over an entire length of the plate 40.

The first inflatable portion 50 and the second inflatable portion 60 are connected to the band 20. The first inflatable portion 50 and the second inflatable portion 60 inflate by being injected with a fluid (gas such as air or liquid). The first inflatable portion 50 presses the puncture site 220 located in the radial artery 210 of the wrist 200. The second inflatable portion 60 presses an ulnar artery 230 and the vicinity of the ulnar artery 230 by pressing the body surface of the wrist 200.

As illustrated in FIG. 2, the first inflatable portion 50 may be located to overlap the vicinity of a part between the first curved portion 42 and the central portion 41.

A constituent material forming the first inflatable portion 50 is not particularly limited as long as the material has flexibility. For example, it is possible to use the same material as the constituent material forming the band 20 mentioned above. In addition, the first inflatable portion 50 may be preferably made of the same or a similar material as or to that of the band 20. In this way, joining the first inflatable portion 50 to the band 20 by fusing may be relatively easily performed, and manufacture may be rather easily performed.

Similarly to the band 20 and the curved plate 40, the first inflatable portion 50 is preferably substantially transparent. In this way, the puncture site 220 may be visually recognized from the outer surface side, and the marker 70 described below may be relatively easily positioned in the puncture site 220.

For example, as illustrated in FIG. 2, a structure of the first inflatable portion 50 may be formed in a shape of a bag obtained by overlapping two sheet materials made of the above-described materials and joining edge portions using a method such as fusing, adhesion, etc. As illustrated in FIG. 1, an external shape of the first inflatable portion 50 may be a rectangle in a state of not being inflated.

As illustrated in FIG. 2, the first inflatable portion 50 may be connected to the band 20 through a first holding portion 51 having flexibility. The first holding portion 51 is preferably provided on the first curved portion 42 side of the curved plate 40. In addition, the first holding portion 51 is preferably made of the same material as that of the first inflatable portion 50. In this way, joining the first holding portion 51 of the first inflatable portion 50 to the band 20 by fusing may be rather easily performed, and manufacture may be rather easily performed.

As illustrated in FIG. 2, the second inflatable portion 60 may be disposed at a different position from that of the first inflatable portion 50 in the longitudinal direction of the band 20. Specifically, the second inflatable portion 60 is disposed to overlap the vicinity of a part between the second curved portion 43 and the central portion 41.

Similarly to the first inflatable portion 50, a constituent material forming the second inflatable portion 60 preferably corresponds to a material having flexibility. For example, it is possible to use the same material as the constituent material forming the band 20 mentioned above. When the same material as that of the band 20 is used, it is possible to rather easily join the second inflatable portion 60 to the band 20 by fusing. Similar to the band 20 and the curved plate 40, the second inflatable portion 60 is preferably substantially transparent.

Similarly to the first inflatable portion 50, a structure of the second inflatable portion 60 may be formed in a shape of a bag obtained by overlapping two sheet materials made of the above-described materials and joining edge portions using a method such as fusing, adhesion, etc.

As illustrated in FIG. 2, the second inflatable portion 60 may be connected to the band 20 through a second holding portion 61 having flexibility. The second holding portion 61 is preferably provided on the second curved portion 43 side of the curved plate 40. In addition, the second holding portion 61 is preferably made of the same material as that of the second inflatable portion 60. In this way, joining the second holding portion 61 of the second inflatable portion 60 to the band 20 by fusing may be rather easily performed, and manufacture may be relatively easily performed.

As illustrated in FIG. 1, a dimension of the second inflatable portion 60 (a length L2 of the second inflatable portion 60) along the longitudinal direction of the band 20 (the direction of the arrow X) is shorter than a dimension of the second inflatable portion 60 (a width W2 of the second inflatable portion 60) along a direction orthogonal to the longitudinal direction of the band 20 (a direction of the arrow Y). That is, when an aspect ratio of the second inflatable portion 60 is defined as a value obtained by dividing the length L2 of the second inflatable portion 60 by the width W2 of the second inflatable portion 60, the aspect ratio of the second inflatable portion 60 is preferably a value less than 1.

In addition, as illustrated in FIG. 1, the width W2 of the second inflatable portion 60 may be less than or equal to a width W3 of the band 20. Further, the second inflatable portion 60 may be attached to the band 20 on the inside of an outer edge of the band 20 in the longitudinal direction.

In addition, the length L2 of the second inflatable portion 60 may be shorter than a length L1 of the first inflatable portion 50 along the longitudinal direction of the band 20. For example, when the length L1 of the first inflatable portion 50 is 25 to 40 mm, the length L2 of the second inflatable portion 60 may be 20 mm or less. That is, the length L1 of the first inflatable portion 50 may be 25 mm to 40 mm, in which case the length L2 of the second inflatable portion 60 is 20 mm or less.

In addition, a volume of the first inflatable portion 50 in an inflated state is larger than a volume of the second inflatable portion 60 in an inflated state. In other words, the interior volume of the first inflatable portion 50 while inflated during use is larger than the interior volume of the second inflatable portion 60 while inflated during use. In the present embodiment, the first inflatable portion 50 and the second inflatable portion 60 are made of the same material. Further, in a state in which the first inflatable portion 50 and the second inflatable portion 60 are not inflated, the length L1 of the first inflatable portion 50 may be longer (greater) than the length L2 of the second inflatable portion 60, and the width W1 of the first inflatable portion 50 may be longer (greater) than the width W2 of the second inflatable portion 60. In this way, the volume of the first inflatable portion 50 in the inflated state is larger than the volume of the second inflatable portion 60. The volume of the first inflatable portion 50 in the inflated state may be larger than the volume of the second inflatable portion 60 by setting an elastic modulus of the constituent material forming the first inflatable portion 50 to be larger than an elastic modulus of the constituent material forming the second inflatable portion 60.

In addition, a relationship between a length L3 of the first curved portion 42 and a length L4 of the second curved portion 43 along a longitudinal direction of the curved plate 40 corresponds to a relationship between the length L1 of the first inflatable portion 50 and the length L2 of the second inflatable portion 60. Specifically, as illustrated in FIG. 2 and FIG. 4, the length L3 of the first curved portion 42 provided on a side where the first inflatable portion 50 is located may be longer than the length L4 of the second curved portion 43 provided on a side where the second inflatable portion 60 is located. For this reason, when the hemostatic device 10 is mounted on the wrist 200, the first inflatable portion 50 and the second inflatable portion 60 may be pressed against the wrist 200 by conforming the first curved portion 42 and the second curved portion 43 to shapes of the first inflatable portion 50 and the second inflatable portion 60, which are inflated, respectively.

As illustrated in FIG. 2, the marker 70 may be provided on the outer surface side of the first inflatable portion 50, that is, on a surface of the first inflatable portion 50 not facing the body surface of the wrist 200. When such a marker 70 is provided in the first inflatable portion 50, the first inflatable portion 50 may be rather easily positioned with respect to the puncture site 220, and thus a position shift of the first inflatable portion 50 is suppressed.

A shape of the marker 70 is not particularly limited. Examples of the shape include a circle, a triangle, a rectangle, etc. In the present embodiment, the shape corresponds to the rectangle.

A size of the marker 70 is not particularly limited. However, for example, when the shape of the marker 70 is a rectangle, a length of a side of the rectangular mark is preferably in a range of 1 to 4 mm. When the length of the side is 5 mm or more, the size of the marker 70 becomes larger when compared to a size of the puncture site 220, and thus it is difficult to position a central portion of the first inflatable portion 50 in the puncture site 220.

A material forming the marker 70 is not particularly limited. Examples thereof include an oily coloring agent such as ink, a resin kneaded with a pigment, etc.

A color of the marker 70 is not particularly limited so long as the color allows the first inflatable portion 50 to be positioned at the puncture site 220. However, a green-based color (green color) is preferable. When the green-based color is adopted, it is relatively easy to visually recognize the marker 70 on blood or skin, and thus the first inflatable portion 50 is more easily positioned in the puncture site 220.

In addition, the marker 70 is preferably translucent or colored transparent. In this way, the puncture site 220 may be visually recognized from an outer surface side of the marker 70.

The manner in which the marker 70 is provided on the first inflatable portion 50 is not particularly limited. For example, it is possible to print the marker 70 on the first inflatable portion 50, to fuse the marker 70 to the first inflatable portion 50, to apply an adhesive to one surface of the marker 70 to paste the marker 70 to the first inflatable portion 50, etc.

The marker 70 may be provided on the inner surface side of the first inflatable portion 50. In this instance, the marker 70 is preferably provided on an inner surface, etc. of the first inflatable portion 50 so as not to directly come into contact with the puncture site 220.

The first injection portion 80 and the second injection portion 81 are parts for injecting a fluid into the first inflatable portion 50 and the second inflatable portion 60, respectively, and are connected to the first inflatable portion 50 and the second inflatable portion 60, respectively, as illustrated in FIG. 1.

The first injection portion 80 includes a flexible first tube 82 having a proximal portion connected to the first inflatable portion 50 and a lumen communicating with the inside (interior) of the first inflatable portion 50, a first bag body 84 disposed at a distal portion of the first tube 82 to communicate with the lumen of the first tube 82, and a tube-shaped first connector 86 connected to the first bag body 84. A check valve (not illustrated) may be incorporated in the first connector 86.

Similarly, the second injection portion 81 includes a flexible second tube 83 having a proximal portion connected to the second inflatable portion 60 and a lumen communicating with an inside (interior) of the second inflatable portion 60, a second bag body 85 disposed at a distal portion of the second tube 83 to communicate with the lumen of the second tube 83, and a tube-shaped second connector 87 connected to the second bag body 85. A check valve (not illustrated) may be incorporated in the second connector 87.

At the time of inflating (expanding) the first inflatable portion 50, a tip of a syringe (not illustrated) is inserted into the first connector 86 to open the check valve, and a plunger of this syringe is pushed to inject a fluid in the syringe into the first inflatable portion 50 through the first injection portion 80. When the first inflatable portion 50 expands, the first bag body 84 communicating with the first inflatable portion 50 through the first tube 82 also expands, and it is possible to visually confirm that the first inflatable portion 50 can be pressed without leakage of the fluid. When the tip of the syringe is withdrawn from the first connector 86 after the fluid is injected into the first inflatable portion 50, the check valve incorporated in the first connector 86 is closed to prevent leakage of the fluid, and so the first inflatable portion 50 is maintained in the expanded state. When the same operation is performed with respect to the second injection portion 81 connected to the second inflatable portion 60, the expanded state of the second inflatable portion 60 is maintained.

Next, a description will be given of an operation using the hemostatic device 10 according to the present embodiment.

Before the hemostatic device 10 is mounted on the wrist 200, the first inflatable portion 50 and the second inflatable portion 60 are in a state of not being inflated (i.e., the first inflatable portion 50 and the second inflatable portion 60 are deflated or substantially empty). When the wrist 200 is punctured, the puncture site 220 with respect to the radial artery 210 is normally biased to a thumb side of the right hand wrist 200. Normally, the introducer sheath is indwelled in the puncture site 220. The band 20 is wrapped around the wrist 200 in which the introducer sheath is indwelled, the first inflatable portion 50 and the band 20 are positioned such that the marker 70 provided in the first inflatable portion 50 overlaps the puncture site 220, and the male side 31 and the female side 32 of the hook and loop fastener 30 are brought into contact with each other and joined to each other, thereby mounting the band 20 on the wrist 200.

The hemostatic device 10 may be mounted on the wrist 200 such that the first injection portion 80 and the second injection portion 81 face a downstream side of a blood flow of the radial artery 210. In this way, the first injection portion 80 and the second injection portion 81 may be operated without interfering with manipulation on the upstream side of the wrist or a device (for example, a sphygmomanometer, etc.) located on the upstream side. In addition, when the hemostatic device 10 is mounted on the right hand wrist 200 such that the first injection portion 80 and the second injection portion 81 face the downstream side, the first inflatable portion 50 is located on the radial artery 210 biased to the thumb side of the wrist 200, and the second inflatable portion 60 is located around the ulnar artery 230. In the case of the artery, the upstream side of the blood vessel refers to a direction of the blood vessel approaching a heart. In addition, the downstream side of the blood vessel refers to a direction of the blood vessel away from the heart.

Figure 5:
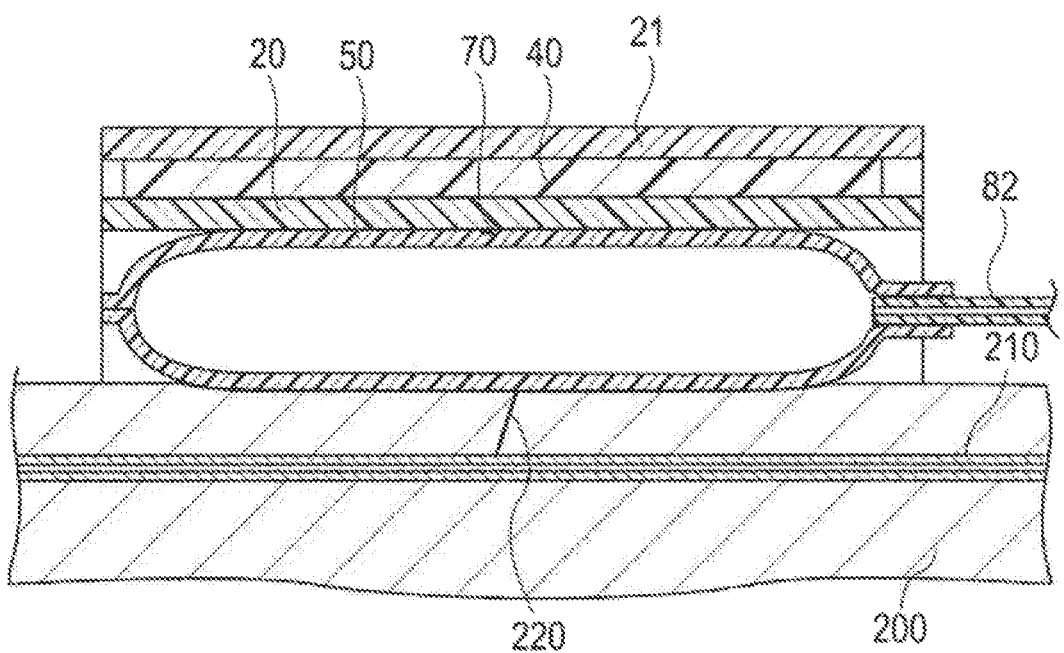
FIG. 5 is a cross-sectional view taken along the section line 5-5 of FIG. 3.

After the hemostatic device 10 is mounted on the wrist 200, the syringe (not illustrated) is connected to the first connector 86 of the first injection portion 80, the fluid is injected into the first inflatable portion 50 as described above, and the first inflatable portion 50 is inflated to press the puncture site 220 as illustrated in FIG. 4 and FIG. 5. A degree of inflation of the first inflatable portion 50, that is, a pressing force to the puncture site 220 located in the radial artery 210 may be rather easily adjusted depending on the case according to an injection amount of the fluid at this time.

After the first inflatable portion 50 is inflated, the syringe is detached from the first connector 86. Then, the introducer sheath is withdrawn from the puncture site 220. In this way, the first inflatable portion 50 maintains an inflated state, and a state of pressing the puncture site 220 is maintained.

Figure 6:
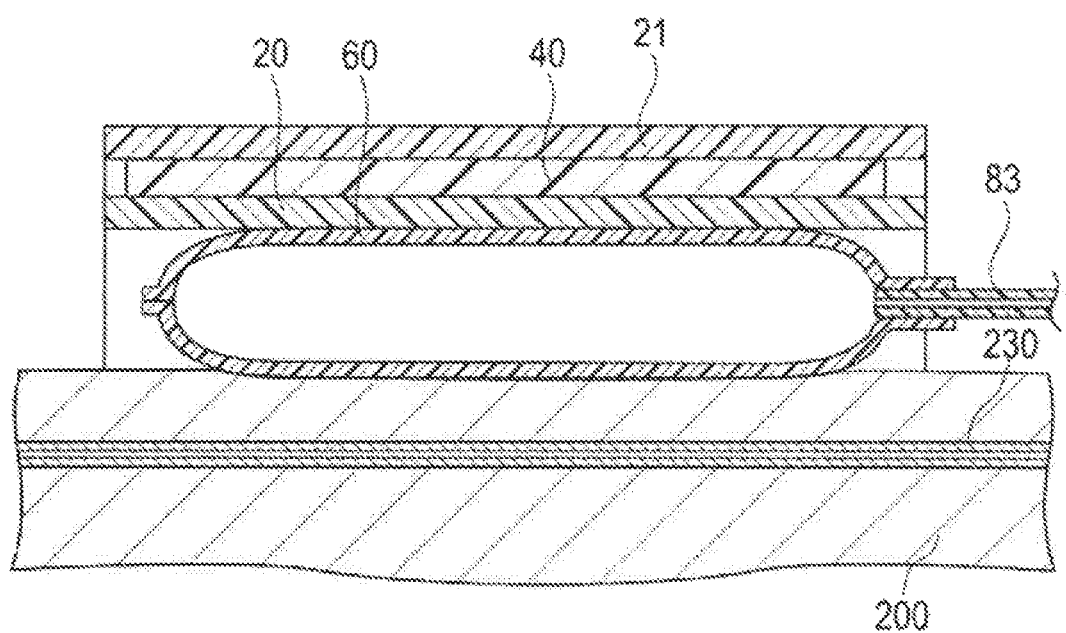
FIG. 6 is a cross-sectional view taken along the section line 6-6 of FIG. 3.

Subsequently, the syringe (not illustrated) is connected to the second connector 87 of the second injection portion 81, the fluid is injected into the second inflatable portion 60 as described above, and the second inflatable portion 60 is inflated to press the ulnar artery 230 as illustrated in FIG. 4 and FIG. 6. A degree of inflation of the second inflatable portion 60, that is, a pressing force to the vicinity of the ulnar artery 230 may be relatively easily adjusted according to an injection amount of the fluid at this time.

When the first inflatable portion 50 and the second inflatable portion 60 are inflated, the curved plate 40 is separated from the body surface of the wrist 200 and hardly comes into contact with the wrist 200. In addition, when the first inflatable portion 50 and the second inflatable portion 60 are inflated after the hemostatic device 10 is mounted, inflation of the first inflatable portion 50 and the second inflatable portion 60 in a direction away from the body surface of the wrist 200 is suppressed by the curved plate 40, and a pressing force of the first inflatable portion 50 and the second inflatable portion 60 is concentrated on the wrist 200 side. For this reason, a pressing force from the first inflatable portion 50 intensively acts on the vicinity of the puncture site 220, and thus the hemostatic effect may be improved.

In addition, when the first inflatable portion 50 presses the radial artery 210, the second inflatable portion 60 may press the ulnar artery 230, thereby preventing an excessive increase in the blood flow flowing to the ulnar artery 230, and suppressing a decrease in the blood flow rate of the radial artery 210. In this way, occlusion of the blood vessel may be prevented, and a decrease in the amount of the platelets, etc. may be suppressed, thereby performing hemostasis at the puncture site 220 in a relatively short time.

The pressing force of the first inflatable portion 50 and the second inflatable portion 60 may be adjusted by adjusting the amount of the fluid injected into the first inflatable portion 50 and the second inflatable portion 60 depending on the progress of hemostasis or the elapsed time.

When hemostasis is completed, the pressing force of the first inflatable portion 50 to the puncture site 220 may be further reduced and the hemostatic device 10 is removed.

When hemostasis in the puncture site 220 is completed and the hemostatic device 10 is removed, the first inflatable portion 50 is contracted, and then the male side 31 and the female side 32 of the hook and loop fastener 30 are peeled off or separated to remove the hemostatic device 10 from the wrist 200. The first inflatable portion 50 may not be contracted when the hemostatic device 10 is removed.

As described above, the hemostatic device 10 according to the present embodiment includes the flexible band 20 that can be wrapped around the wrist 200 in which the radial artery 210 and the ulnar artery 230 run, the hook and loop fastener 30 that secures the band 20 in a state of being wrapped around the wrist 200, the first inflatable portion 50 connected to the band 20 and allowed to press the puncture site 220 of the radial artery 210 by being inflated in response to injection of the fluid, and the second inflatable portion 60 disposed at a different position from that of the first inflatable portion 50 in the longitudinal direction of the band 20 and allowed to press the ulnar artery 230. Further, the length L2 of the second inflatable portion 60 along the longitudinal direction of the band 20 is shorter than the width W2 of the second inflatable portion 60 along the direction orthogonal to the longitudinal direction of the band 20.

According to the hemostatic device 10 configured as described above, it is possible to enhance the hemostatic effect by suppressing a decrease in blood flow rate of the radial artery. In addition, the length L2 of the second inflatable portion 60 is shorter than the width W2 of the second inflatable portion 60. For this reason, a part of the second inflatable portion 60 coming into contact with the wrist 200 may have a shape extending along running of the ulnar artery 230 (i.e., extending along the direction of extent of the ulnar artery 230). As a result, it is possible to further narrow a range in a part (a tendon, a nerve, etc.) other than the ulnar artery 230 pressed by the second inflatable portion 60 while favorably pressing the ulnar artery 230. That is, the inflated second portion 60 is able to press on the ulnar artery 230, yet is not so likely to press on other parts not intended to be pressed. For this reason, it is possible to reduce numbness or pain at the time of using the hemostatic device 10.

In addition, the width W2 of the second inflatable portion 60 may be less than or equal to the width W3 of the band 20. For this reason, the second inflatable portion 60 does not protrude outward from the band 20, and the second inflatable portion 60 may be configured not to interfere with manipulation performed around a mounting position of the hemostatic device 10, another device, etc.

In addition, the length L2 of the second inflatable portion 60 is shorter than the length L1 of the first inflatable portion 50 along the longitudinal direction of the band 20. The first inflatable portion 50 needs to tightly press the puncture site 220 to perform hemostasis, and thus preferably presses not only the puncture site 220 but also the vicinity thereof. On the other hand, it is sufficient for the second inflatable portion 60 to be able to press only the ulnar artery 230 to prevent an excessive increase in the blood flow rate of the ulnar artery 230. When the length L2 of the second inflatable portion 60 is shorter than the length L1 of the first inflatable portion 50, it is possible to narrow a range in a part (a tendon, a nerve, etc.) other than the ulnar artery 230 pressed by the second inflatable portion 60 while ensuring a range pressed by the first inflatable portion 50.

In addition, the second inflatable portion 60 can be inflated by injection of a fluid, and the volume of the first inflatable portion 50 in the inflated state may be larger than the volume of the second inflatable portion 60 in the inflated state. The first inflatable portion 50 requires a relatively strong compressive force to perform hemostasis. On the other hand, it is sufficient for the second inflatable portion 60 to be able to press the ulnar artery 230 to such an extent as to prevent an excessive increase in the blood flow rate of the ulnar artery 230, and a strong pressing force required by the first inflatable portion 50 is unnecessary. When the volume in the inflated state is large, the wrist 200 is more strongly pressed. Thus, when the volume of the first inflatable portion 50 in the inflated state is larger than the volume of the second inflatable portion 60 in the inflated state, it is possible to decrease a pressing force by the second inflatable portion 60 while ensuring a pressing force by the first inflatable portion 50.

Modification of First Embodiment

First, a description will be given of second inflatable portions 160, 260, 360, and 460 according to Modifications 1 to 4. In the description below, features that are the same or similar to those described above are identified by the same reference numerals and a detailed description of such features is not repeated.

Figure 7A:
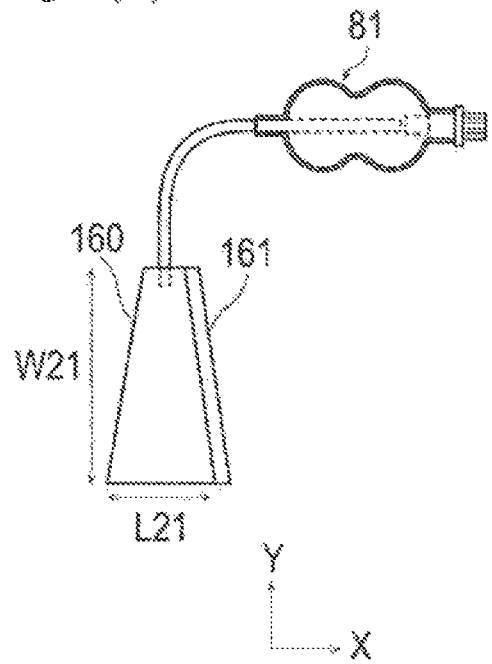
FIG. 7(A) is a schematic view illustrating a pressing member according to Modification 1 of the first embodiment.

While an external shape of the second inflatable portion 60 according to the above-described embodiment is a rectangle in a state of not being inflated (see FIG. 1), the external shape of the second inflatable portion 160 according to Modification 1 is a trapezoidal shape (see FIG. 7(A)). The second inflatable portion 160 may be connected to the band 20 through a second holding portion 161. In addition, a maximum length L21 of the second inflatable portion 160 along the longitudinal direction of the band 20 (a maximum separation distance between two sides of the trapezoidal extending along a Y direction) may be shorter than a maximum width W21 of the second inflatable portion 160 along the direction orthogonal to the longitudinal direction of the band 20.

Figure 7B:
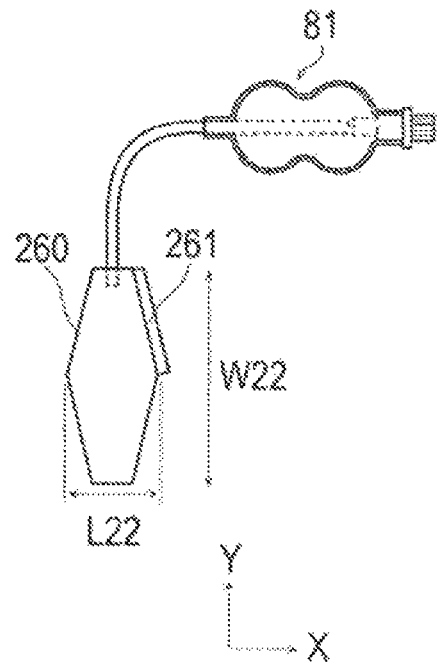
FIG. 7(B) is a schematic view illustrating a pressing member according to Modification 2 of the first embodiment.

In addition, the external shape of the second inflatable portion 260 according to Modification 2 is a hexagonal shape (see FIG. 7(B)). The second inflatable portion 260 may be connected to the band 20 through a second holding portion 261. In addition, a maximum length L22 of the second inflatable portion 260 along the longitudinal direction of the band 20 (a maximum separation distance among distances between apexes of the hexagon facing each other along the longitudinal direction of the band 20) is shorter than a maximum width W22 of the second inflatable portion 260 along the direction orthogonal to the longitudinal direction of the band 20.

Figure 7C:
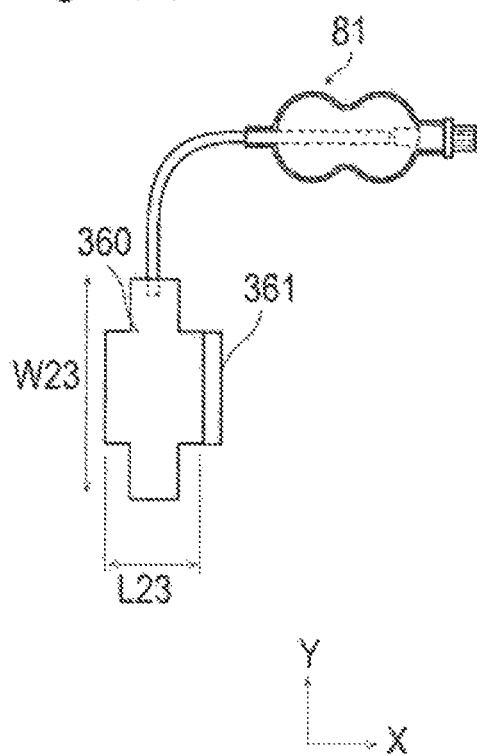
FIG. 7(C) is a schematic view illustrating a pressing member according to Modification 3 of the first embodiment.

In addition, the external shape of the second inflatable portion 360 according to Modification 3 is a cross shape including a rectangle elongated in the direction orthogonal to the longitudinal direction of the band 20 and two protrusions protruding outward in rectangular shapes along the longitudinal direction of the band 20 from substantially central parts of two long sides of the rectangle, respectively (see FIG. 7(C)). The second inflatable portion 360 may be connected to the band 20 through a second holding portion 361. In addition, a maximum length L23 of the second inflatable portion 360 along the longitudinal direction of the band 20 (a distance between an edge portion of one protrusion extending in a Y direction and an edge portion of the other protrusion extending in the Y direction) may be shorter than a maximum width W23 of the second inflatable portion 360 along the direction orthogonal to the longitudinal direction of the band 20.

Figure 7D:
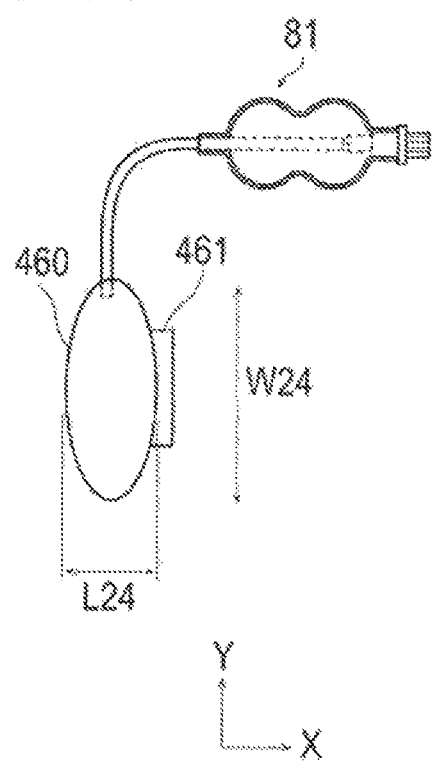
FIG. 7(D) is a schematic view illustrating a pressing member according to Modification 4 of the first embodiment.

In addition, the external shape of the second inflatable portion 460 according to Modification 4 is an elliptical shape (see FIG. 7(D)). The second inflatable portion 460 may be connected to the band 20 through a second holding portion 461. In addition, a maximum length L24 of the second inflatable portion 460 along the longitudinal direction of the band 20 may be shorter than a maximum width W24 of the second inflatable portion 460 along the direction orthogonal to the longitudinal direction of the band 20.

According to a hemostatic device 10 according to the above-described Modifications 1 to 4, a part of the second inflatable portions 160, 260, 360, and 460 coming into contact with the wrist 200 at the time of mounting the hemostatic device 10 on the wrist 200 may have a shape extending along running of the ulnar artery 230 (i.e., the direction of extent of the ulnar artery 230). For this reason, it is possible to favorably press the ulnar artery 230 by the second inflatable portions 160, 260, 360, and 460, and it is possible to reduce a press range (range or area at which pressure is applied) of a part (a tendon, a nerve, etc.) other than the ulnar artery 230. As a result, it is possible to reduce numbness or pain felt by a user at the time of using the hemostatic device 10.

As described above in Modifications 1 to 4, the external shape of the second inflatable portion in plan view in a state of not being inflated is not limited to the rectangular shape described in the above embodiment when the maximum length of the second inflatable portion along the longitudinal direction of the band 20 may be shorter than the maximum length of the second inflatable portion along the direction orthogonal to the longitudinal direction of the band 20.

Next, a description will be given of second inflatable portions 560 and 660 according to Modifications 5 and 6.

Figure 8A:
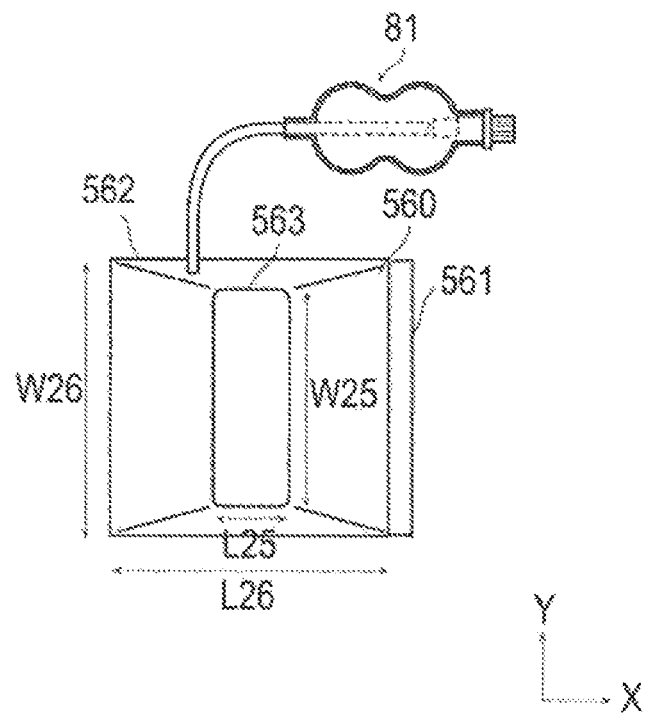
FIG. 8(A) is a schematic view illustrating a pressing member according to Modification 5 of the first embodiment.

The second inflatable portion 60 according to the above-described embodiment is configured by overlapping two flat and rectangular sheets and joining edge portions of the overlapping sheets (see FIG. 1). On the other hand, the second inflatable portion 560 according to Modification 5 may be configured by overlapping a sheet, whose central part protrudes, with one flat sheet and joining edge portions of the two sheets such that the external shape of the second inflatable portion 560 in an inflated state corresponds to a shape of a truncated prism (see FIG. 8(A)). The second inflatable portion 560 may be connected to the band 20 through a second holding portion 561.

The second inflatable portion 560 comes into contact with the band 20 on a first surface 562 whose area is largest in an inflated state and comes into contact with a wrist 200 on a second surface 563 side corresponding to a tapered end surface in the shape of the truncated prism. Further, a length L25 of the second surface 563 along the longitudinal direction of the band 20 is shorter than a width W25 of the second surface 563 along the direction orthogonal to the longitudinal direction of the band 20.

According to a hemostatic device 10 according to the above-described Modification 5, a part of the second inflatable portion 560 coming into contact with the wrist 200 at the time of mounting the hemostatic device 10 on the wrist 200 may have a shape extending along the running (direction of extent) of the ulnar artery 230. For this reason, it is possible to press the ulnar artery 230 by the second inflatable portion 560, and it is possible to reduce a press range (range or area at which pressure is applied) other than the ulnar artery 230 such as a tendon, a nerve, etc. around the ulnar artery 230. As a result, it is possible to reduce numbness or pain felt by the user at the time of using the hemostatic device 10.

In this way, when the above relationship between the length L25 and W25 of the second surface 563 holds, a relationship between a length L26 of the first surface 562 along the longitudinal direction of the band 20 and a width W26 of the first surface 562 along the direction orthogonal to the longitudinal direction of the band 20 is not limited. For example, the length L26 of the first surface 562 may be greater than or equal to the width W26 of the first surface 562.

Figure 8B:
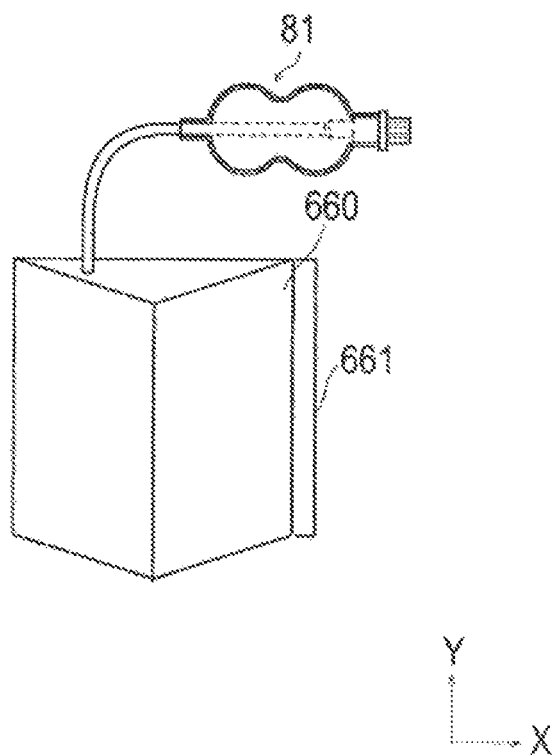
FIG. 8(B) is a schematic view illustrating a pressing member according to Modification 6 of the first embodiment.

In addition, an external shape of the second inflatable portion 660 according to Modification 6 in an inflated state corresponds to a triangular prism unlike Modification 5 (see FIG. 8(B)). In this case, the ulnar artery 230 is pressed around a tapered distal portion of the triangular prism. For this reason, a part of the second inflatable portion 660 coming into contact with the wrist 200 at the time of mounting the hemostatic device 10 on the wrist 200 may have a shape extending along running (direction of extent) of the ulnar artery 230. Therefore, it is possible to favorably press the ulnar artery 230 by the second inflatable portion 660, and it is possible to reduce a press range (range or area at which pressure is applied) of a part (a tendon, a nerve, etc.) other than the ulnar artery 230. As a result, it is possible to reduce numbness or pain felt by the user at the time of using the hemostatic device 10.

The hemostatic devices according to the first embodiment and the modifications of the first embodiment described above may be appropriately modified while still being within the scope of the description in the claims.

For example, each portion included in the hemostatic device may be replaced with a portion having a desired configuration capable of exerting the same or similar function. In addition, an arbitrary component may be added.

In addition, the invention is not limited to the hemostatic device used by being mounted on the wrist, and is applicable to a hemostatic device used by being mounted on any part of the arm in which the radial artery and the ulnar artery run.

In addition, the pressing member may not be inflated by being injected with the fluid. For example, the pressing member may be made of a material such as metal, plastic, etc.

In addition, it is possible to provide an auxiliary compressing portion that compresses the first inflatable portion to overlap with the first inflatable portion between the first inflatable portion and the band in order to adjust a pressing direction of the first inflatable portion. For example, the auxiliary compressing portion may be inflated by being injected with a fluid similar to the first inflatable portion, or it is possible to use a sponge-like substance, an elastic material, an aggregate of fibers such as cotton, a combination thereof, etc.

In addition, the external shape of the first inflatable portion is not limited to the rectangle in the state in which the first inflatable portion is not inflated. For example, it is possible to adopt a circle, an ellipse, or a polygon such as a pentagon.

In addition, the marker may not be provided in the first inflatable portion, and may be provided in the band, the curved plate, or the auxiliary compressing portion. In addition, the marker may be more preferably provided to overlap the central portion of the first inflatable portion.

In addition, a projection provided on a pressing member of a hemostatic device according to a third embodiment described below may be provided on the pressing member (second inflatable portion) of the hemostatic device according to the first embodiment and the pressing member (second inflatable portion) of the hemostatic device according to Modifications of the first embodiment.

Second Embodiment

Next, a description will be given of a hemostatic device according to a second embodiment of the hemostatic device disclosed here.

Figure 13:
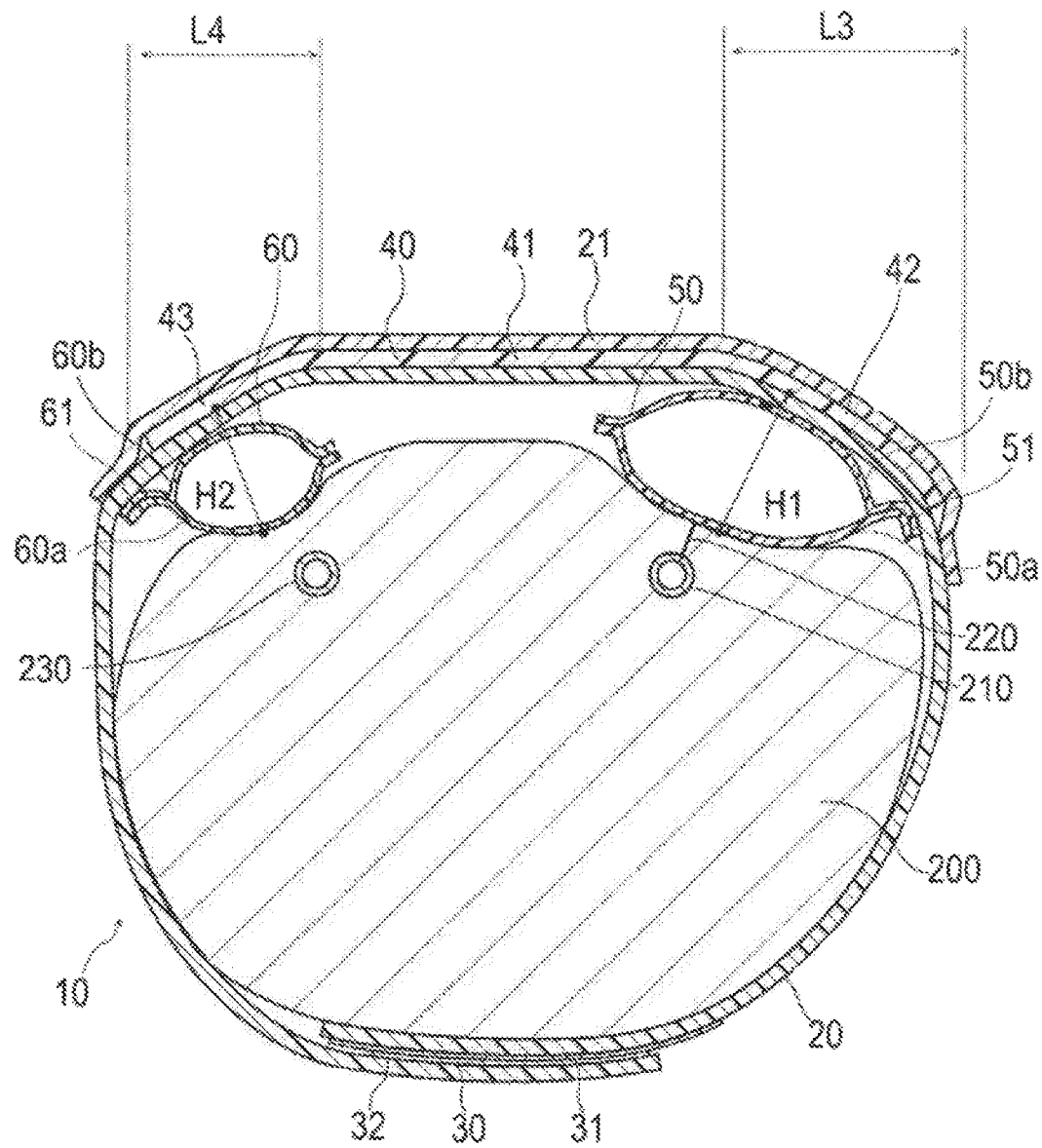
FIG. 13 is a cross-sectional view taken along the section line 13-13 of FIG. 12.

As illustrated in FIG. 13, a hemostatic device 10 according to the second embodiment of the invention is used to perform hemostasis at a puncture site 220 after withdrawing an introducer sheath indwelled in the puncture site 220 (corresponding to a part to be subjected to hemostasis) formed in a radial artery 210 of a wrist 200 to insert a catheter, etc. performing treatment/examination, etc. into a blood vessel.

Figure 9:
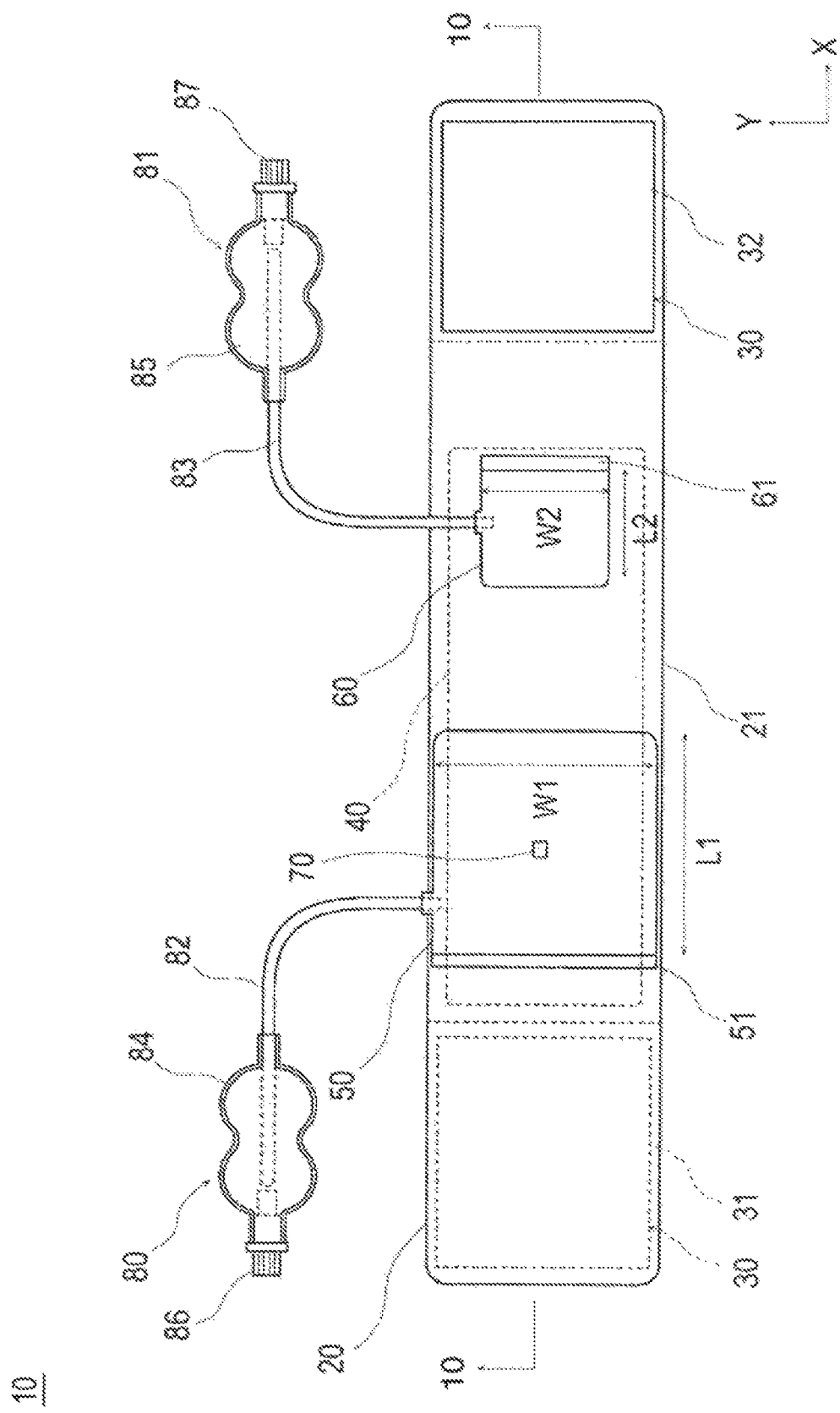
FIG. 9 is a plan view of a hemostatic device according to a second embodiment viewed from an inner surface side.
Figure 10:
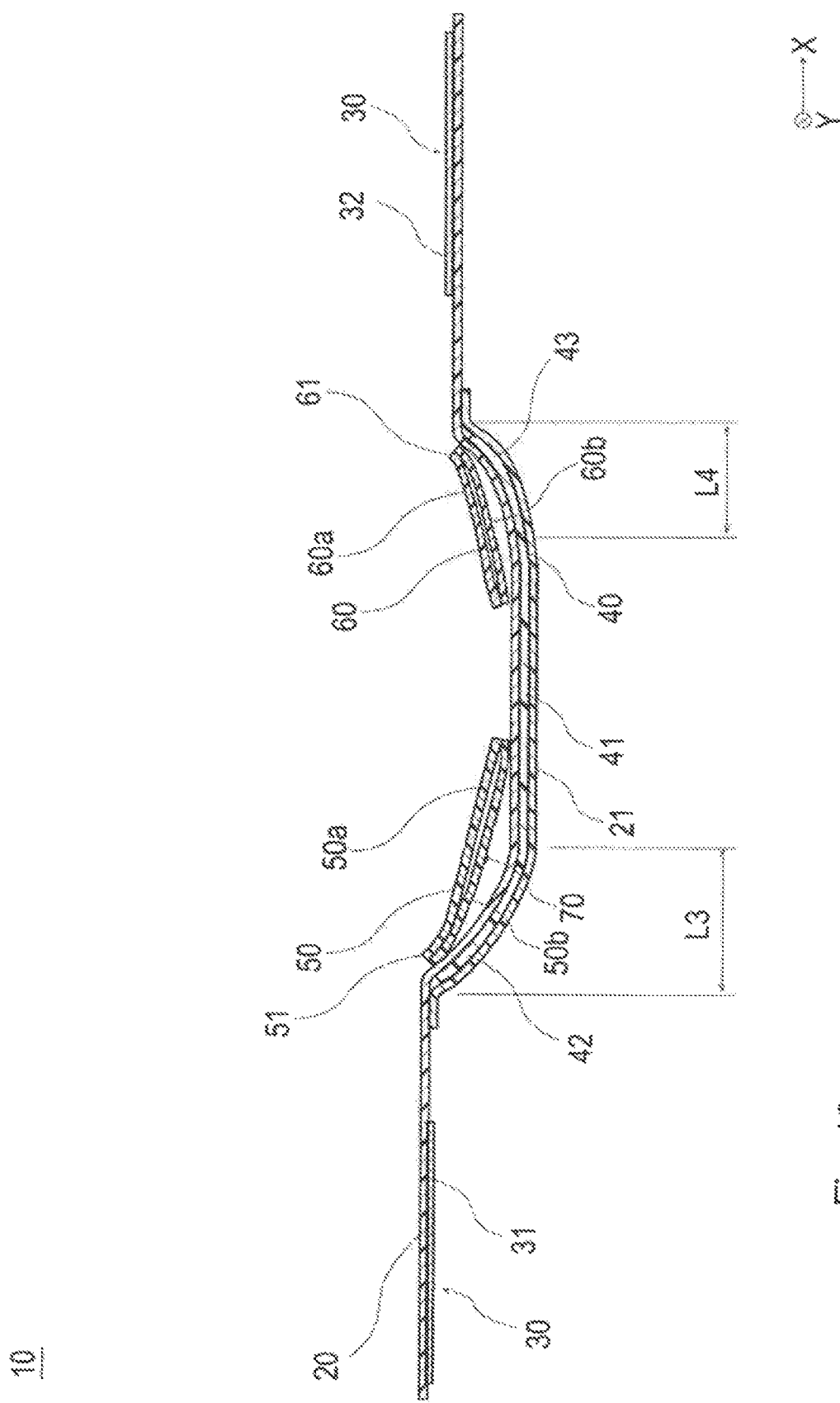
FIG. 10 is a cross-sectional view taken along the section line 10-10 of FIG. 9.

As illustrated in FIG. 9 and FIG. 10, the hemostatic device 10 includes a band 20 for wrapping around the wrist 200, a hook and loop fastener 30 (corresponding to a securing portion) for securing the band 20 in a state of being wrapped around the wrist 200, a curved plate 40 (corresponding to a support plate), a first inflatable portion 50 (corresponding to an inflatable portion or inflatable member/element), a second inflatable portion 60 (corresponding to a pressing member), a marker 70, a first injection portion 80, and a second injection portion 81.

In the description here, a side (mounting surface side) of the band 20 facing a body surface of the wrist 200 is referred to as an "inner surface side", and an opposite side of the band is referred to as an "outer surface side" when the band 20 is wrapped around the wrist 200.

In addition, in the drawings, a longitudinal direction of the band 20 is indicated as an arrow X, and a direction orthogonal to the longitudinal direction of the band 20 is indicated as an arrow Y.

The band 20 may be a flexible band-shaped member. As illustrated in FIG. 13, the band 20 may be wrapped around an outer periphery of the wrist 200 substantially once. As illustrated in FIG. 10, a curved plate holding portion 21 that holds the curved plate 40 is formed at a central portion of the band 20. The curved plate holding portion 21 may be doubled by separate band-shaped members joined to an outer surface side (or inner surface side) using a method such as fusing (heat-fusing, high-frequency fusing, ultrasonic fusing, etc.), adhesion (adhesion by an adhesive or a solvent), etc. and holds the curved plate 40 inserted into a gap therebetween.

Figure 12:
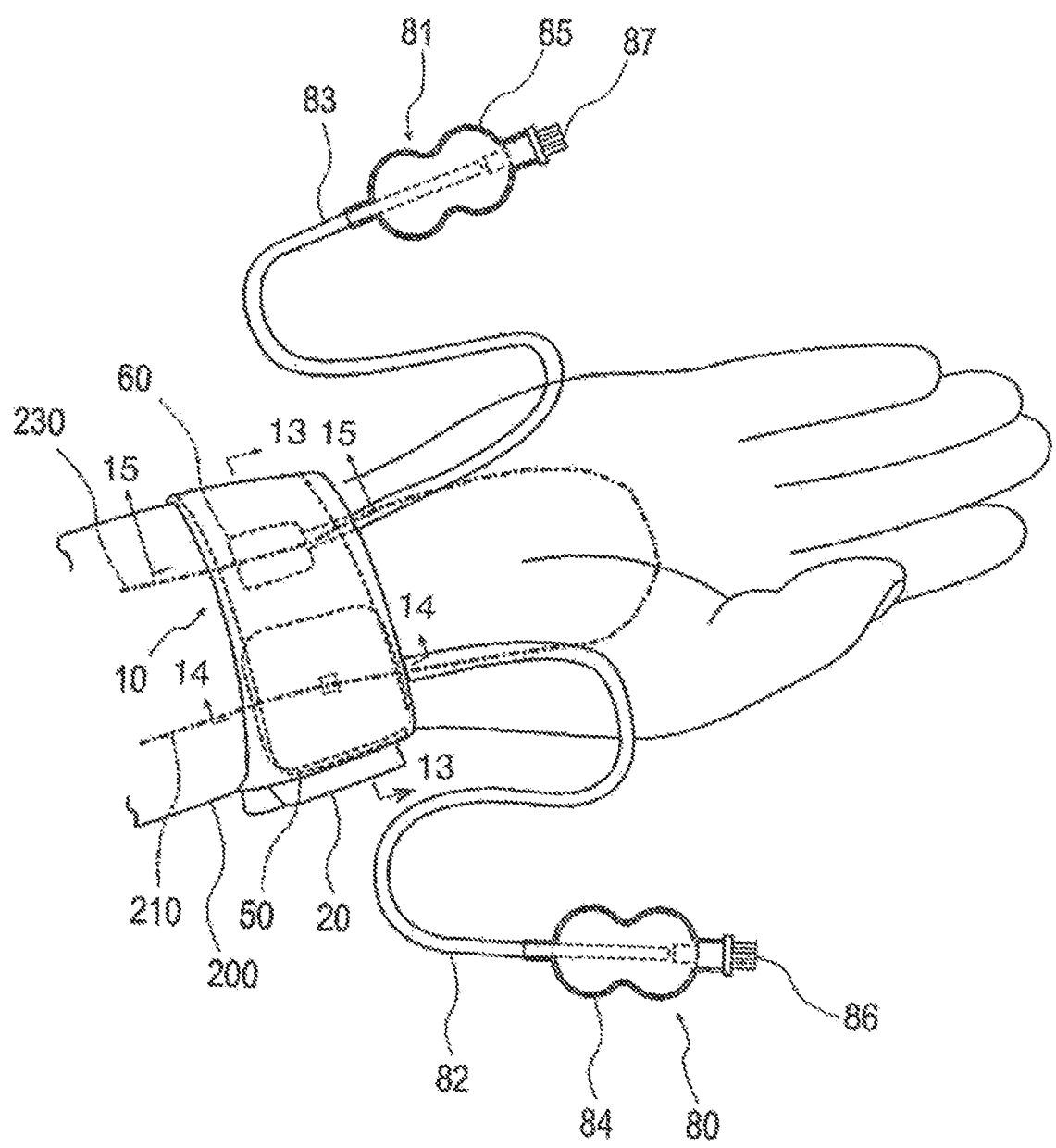
FIG. 12 is a perspective view illustrating a state of mounting the hemostatic device according to the second embodiment around an arm.
Figure 14:
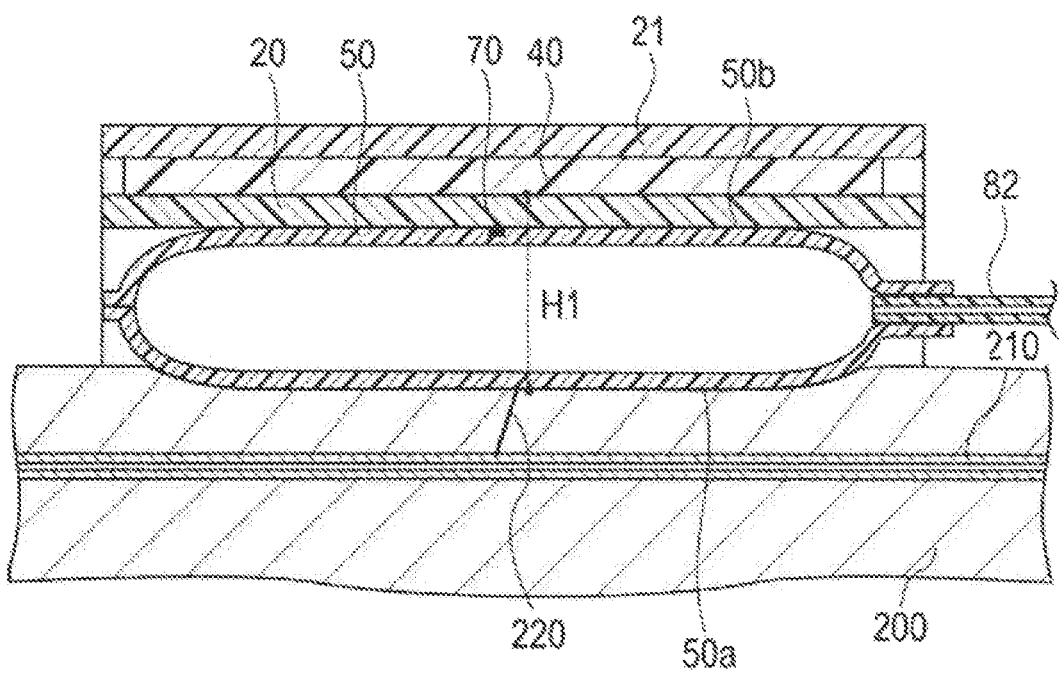
FIG. 14 is a cross-sectional view taken along the section line 14-14 of FIG. 12.

A male side (or a female side) 31 of the hook and loop fastener 30 generally referred to as Magic Tape (registered trademark), etc. may be disposed on the outer surface side of the band 20 near a left end of FIG. 9, and a female side (or a male side) 32 of the hook and loop fastener 30 may be disposed on the inner surface side of the band 20 near a right end of FIG. 9. As illustrated in FIG. 12 and FIG. 14, the band 20 is wrapped around the wrist 200, and the male side 31 and the female side 32 are joined together, thereby mounting the band 20 on the wrist 200. Means for securing the band 20 to the wrist 200 in a wrapped state is not limited to the hook and loop fastener 30. For example, the means may correspond to a snap, a button, a clip, or a frame member passing an end portion of the band 20.

A constituent material forming the band 20 is not particularly limited as long as the material has flexibility, and examples thereof include polyvinyl chloride, polyolefins such as polyethylene, polypropylene, polybutadiene and ethylene-vinyl acetate copolymers (EVA), polyesters such as polyethylene terephthalate (PET) and polybutylene terephthalate (PBT), polyvinylidene chloride, silicone, polyurethane, various thermoplastic elastomers such as polyamide elastomers, polyurethane elastomers and polyester elastomers, and an arbitrary combination of the above (blend resin, polymer alloy, laminate, etc.).

The band 20 is preferably substantially transparent. However, the band 20 may not be transparent, and may be translucent or colored transparent. In this way, the puncture site 220 may be visually recognized from the outer surface side, and the marker 70 described below may be rather easily positioned in the puncture site 220.

As illustrated in FIG. 10, the curved plate 40 may be held in the band 20 by being inserted into or positioned in the doubly formed curved plate holding portion 21 of the band 20. The curved plate 40 may be made of a material more rigid than the material of the band 20 so that the plate 40 is more rigid that the flexible band 20 and may maintain a substantially constant shape.

The curved plate 40 may have a shape elongated in the longitudinal direction of the band 20 (a direction of the arrow X). A central portion 41 of the curved plate 40 in the longitudinal direction may have a flat plate shape almost without being curved, and a first curved portion 42 (left side of FIG. 10) and a second curved portion 43 (right side of FIG. 10) curved toward an inner peripheral side and along the longitudinal direction of the band 20 (a circumferential direction of the wrist 200) are formed at both sides of the central portion 41, respectively.

A constituent material forming the curved plate 40 is not particularly limited as long as the puncture site 220 can be visually recognized. Examples of the material include acrylic resins, polyvinyl chloride (particularly rigid polyvinyl chloride), polyolefins such as polyethylene, polypropylene and polybutadiene, polystyrene, poly(4-methyl pentene-1), polycarbonates, ABS resins, polymethyl methacrylate (PMMA), polyacetals, polyarylates, polyacrylonitriles, polyvinylidene fluorides, ionomers, acrylonitrile-butadiene-styrene copolymers, polyesters such as polyethylene terephthalate (PET) and polybutylene terephthalate (PBT), butadiene-styrene copolymers, aromatic or aliphatic polyamides, and fluorocarbon resins such as polytetrafluoroethylene.

Similar to the band 20, the curved plate 40 is preferably substantially transparent. However, the curved plate 40 may not be transparent, and may be translucent or colored transparent. In this way, the puncture site 220 may be reliably visually recognized from the outer surface side, and the marker 70 described below may be easily positioned in the puncture site 220. The curved plate 40 may not have a non-curved part such as the central portion 41, that is, may be curved over an entire length of the plate.

The first inflatable portion 50 and the second inflatable portion 60 are connected to the band 20. The first inflatable portion 50 and the second inflatable portion 60 inflate by being injected with a fluid (gas such as air or liquid). The first inflatable portion 50 presses the puncture site 220 located in the radial artery 210 of the wrist 200. The second inflatable portion 60 presses the ulnar artery 230 and the vicinity of the ulnar artery 230 by pressing the body surface of the wrist 200.

As illustrated in FIG. 10, the first inflatable portion 50 may be located to overlap the vicinity of a part between the first curved portion 42 and the central portion 41.

A constituent material forming the first inflatable portion 50 is not particularly limited as long as the material has flexibility. For example, it is possible to use the same material as the constituent material forming the band 20 mentioned above. In addition, the first inflatable portion 50 is preferably made of the same or a similar material as or to that of the band 20. In this way, joining the first inflatable portion 50 to the band 20 by fusing may be rather easily performed, and manufacture may be relatively easily performed.

Similar to the band 20 and the curved plate 40, the first inflatable portion 50 may be preferably substantially transparent. In this way, the puncture site 220 may be visually recognized from the outer surface side, and the marker 70 described below may be easily positioned in the puncture site 220.

For example, as illustrated in FIG. 10, a structure of the first inflatable portion 50 may be formed in a shape of a bag obtained by overlapping two sheet materials made of the above-described materials and joining edge portions using a method such as fusing, adhesion, etc. As illustrated in FIG. 9, an external shape of the first inflatable portion 50 may be a rectangle in a state of not being inflated.

As illustrated in FIG. 10, the first inflatable portion 50 is connected to the band 20 through a first holding portion 51 having flexibility. The first holding portion 51 is preferably provided on the first curved portion 42 side of the curved plate 40. In addition, the first holding portion 51 is preferably made of the same material as that of the first inflatable portion 50. In this way, joining to the band 20 by fusing may be easily performed, and manufacture may be easily performed.

As illustrated in FIG. 10, the second inflatable portion 60 may be disposed at a different position from that of the first inflatable portion 50 in the longitudinal direction of the band 20. Specifically, the second inflatable portion 60 may be disposed to overlap the vicinity of a part between the second curved portion 43 and the central portion 41.

Similar to the first inflatable portion 50, a constituent material forming the second inflatable portion 60 preferably corresponds to a material having flexibility. For example, it is possible to use the same material as the constituent material forming the band 20 mentioned above. When the same material as that of the band 20 is used, it is possible to rather easily join the second inflatable portion 60 to the band 20 by fusing. Similar to the band 20 and the curved plate 40, the second inflatable portion 60 is preferably substantially transparent.

Like the first inflatable portion 50, a structure of the second inflatable portion 60 may be formed in a shape of a bag obtained by overlapping two sheet materials made of the above-described materials and joining edge portions using a method such as fusing, adhesion, etc. Even though a member (the second inflatable portion 60) that inflates by being injected with a fluid is given as an example of the pressing member that presses the ulnar artery 230 in the present embodiment, the pressing member may be configured differently than described above. For example, the pressing member that presses the ulnar artery 230 may correspond to a relatively rigid member such as plastic, metal, etc. or may correspond to a sponge-like substance, an elastic material, an aggregate of fibers such as cotton, or an elastic member formed by combining these materials.

As illustrated in FIG. 10, the second inflatable portion 60 may be connected to the band 20 through a second holding portion 61 having flexibility. The second holding portion 61 is preferably provided on the second curved portion 43 side of the curved plate 40. In addition, the second holding portion 61 is preferably made of the same material as that of the second inflatable portion 60. In this way, joining to the band 20 by fusing may be relatively easily performed, and manufacture may be rather easily performed.

Figure 11:
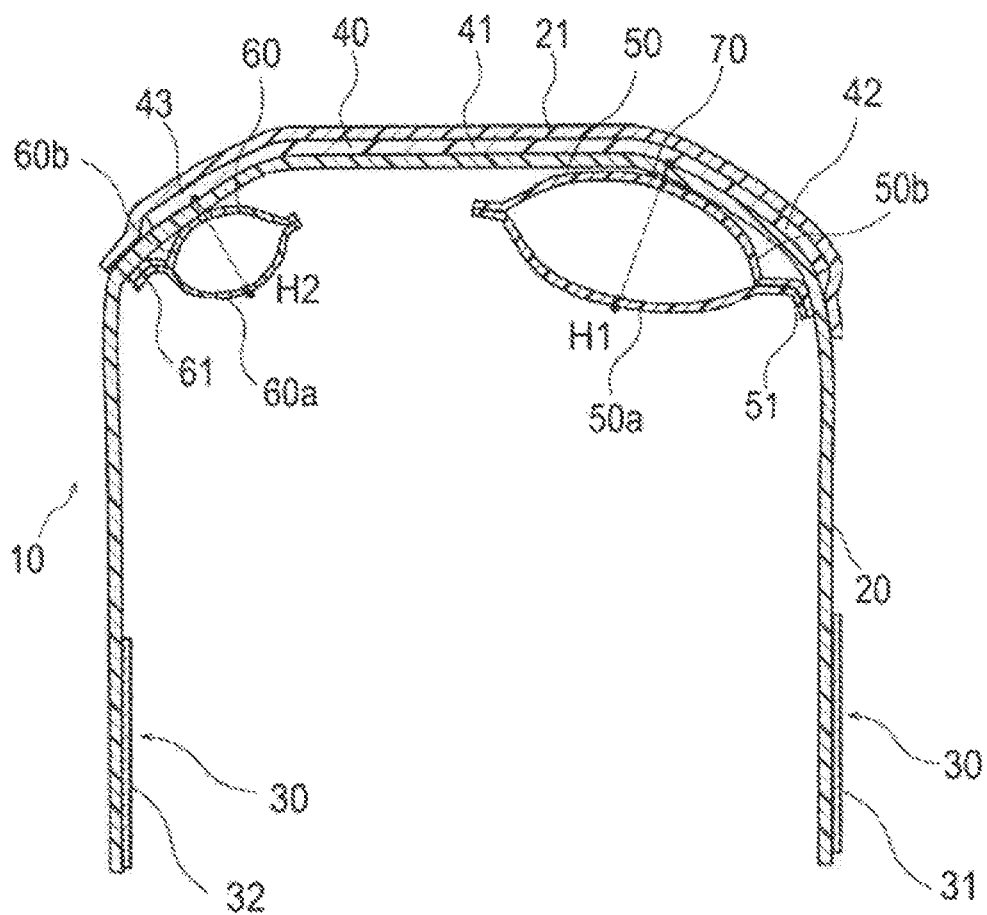
FIG. 11 is a cross-sectional view illustrating a dimension example of an inflatable portion and a dimension example at the time of inflating a pressing member of the hemostatic device according to the second embodiment.

As illustrated in FIG. 11, a surface of the first inflatable portion 50 disposed on the wrist 200 side is a first surface 50a, a surface of the first inflatable portion 50 disposed on the band 20 side is a second surface 50b, a surface of the second inflatable portion 60 disposed on the wrist 200 side is a third surface 60a, and a surface of the second inflatable portion 60 disposed on the band 20 side is set to a fourth surface 60b. In a state in which at least a portion of the second surface 50b of the first inflatable portion 50 and at least a portion of the fourth surface 60b of the second inflatable portion 60 are brought into contact with a range of the band 20 in which the curved plate 40 is disposed, a length H1 of a perpendicular line from the curved plate 40 (line H1 is perpendicular to the portion of the plate intersected by the line H1) to the first surface 50a at the time of inflating the first inflatable portion 50 is longer than a length H2 of a perpendicular line from the curved plate 40 (line H2 is perpendicular to the portion of the pate intersected by the line H2) to the third surface 60a at the time of inflating the second inflatable portion 60.

Even though the length of the perpendicular line from the curved plate 40 to the first surface 50a differs depending on the position on the curved plate 40 set to a start point of the perpendicular line, the above-mentioned "length H1 of the perpendicular line from the curved plate 40 to the first surface 50a" is defined as a maximum length of a perpendicular line from a surface of the curved plate 40 on the wrist 200 side to the first surface 50a in the present embodiment. Similarly, "the length H2 of the perpendicular line from the curved plate 40 to the third surface 60a" is defined as a maximum length of a perpendicular line from a surface of the curved plate 40 on the wrist 200 side to the third surface 60a. Specifically, as illustrated in FIG. 11, a start point on the curved plate 40 side is selected to set an approximate center of the first surface 50a at which the curved plate 40 and the first surface 50a are most distant from each other as an end point, thereby defining the length H1 of the perpendicular line from the curved plate 40 to the first surface 50a. Similarly, a start point on the curved plate 40 side is selected to set an approximate center of the third surface 60a at which the curved plate 40 and the third surface 60a are most distant from each other as an end point, thereby defining the length H2 of the perpendicular line from the curved plate 40 to the third surface 60a.

Positions corresponding to the start points of the respective perpendicular lines H1 and H2 may allow comparison of a distance between the curved plate 40 and the first surface 50a with a distance between the curved plate 40 and the third surface 60a, and are not limited to the above definitions. For example, a surface of the curved plate 40 opposite to the surface on the wrist 200 side may be set as a start point of the perpendicular line.

An external shape, a structure, an elastic modulus of a constituent material, etc. of each of the first inflatable portion 50 and the second inflatable portion 60 are preferably selected or designed as appropriate such that the length H1 of the perpendicular line is longer than the length H2 of the perpendicular line.

In the present embodiment, the first inflatable portion 50 and the second inflatable portion 60 are made of the same material, and an external shape of the first inflatable portion 50 is larger than an external shape of the second inflatable portion 60 in a state of not being inflated, so that the length H1 of the perpendicular line is longer than the length H2 of the perpendicular line in an inflated state. Specifically, a dimension of the first inflatable portion 50 (the length L1 of the first inflatable portion 50) along the longitudinal direction of the band 20 may be longer than a dimension of the second inflatable portion 60 (the length L2 of the second inflatable portion 60) along the longitudinal direction of the band 20. In addition, a dimension of the first inflatable portion 50 (the width W1 of the first inflatable portion 50) along the direction orthogonal to the longitudinal direction of the band 20 is longer than a dimension of the second inflatable portion 60 (the width W2 of the second inflatable portion 60) along the direction orthogonal to the longitudinal direction of the band 20.

It is possible, for example, to include a structure in which the length H1 of the perpendicular line is longer than the length H2 of the perpendicular line by changing a material of a part of the second inflatable portion 60 to provide a portion that rarely inflates (inflates relatively little) in a direction of the perpendicular line. Alternatively, for example, the first inflatable portion 50 may be made of a material having a higher elastic modulus than that of the second inflatable portion 60, and the first inflatable portion 50 may be configured to be able to inflate more than the second inflatable portion 60, so that the length H1 of the perpendicular line is longer than the length H2 of the perpendicular line.

In addition, in the present embodiment, a description has been given of a case in which the external shape of the first inflatable portion 50 and the external shape of the second inflatable portion 60 are similar to each other. However, for example, even in a case in which the external shape of the first inflatable portion 50 and the external shape of the second inflatable portion 60 are not similar to each other, effects described below may be obtained similarly to the present embodiment by setting a maximum length of the perpendicular line from the curved plate 40 to the first surface 50a to be longer than a maximum length of the perpendicular line from the curved plate 40 to the third surface 60a.

In addition, as described above, the length L1 of the first inflatable portion 50 may be longer than the length L2 of the second inflatable portion 60, and the width W1 of the first inflatable portion 50 may be longer than the width W2 of the second inflatable portion 60. For this reason, a surface area of the first surface 50a of the first inflatable portion 50 in an inflated state is larger than a surface area of the third surface 60a of the second inflatable portion 60 in an inflated state. In addition, the first inflatable portion 50 can be inflated more than the second inflatable portion 60 in the longitudinal direction of the band 20, the direction orthogonal to the longitudinal direction of the band 20, and the direction of the perpendicular line mentioned above. For this reason, the volume of the first inflatable portion 50 in the inflated state is larger than the volume of the second inflatable portion in the inflated state.

The length L1 of the first inflatable portion 50 may be longer than the length L2 of the second inflatable portion 60, and the width W1 of the first inflatable portion 50 may be the same as the width W2 of the second inflatable portion 60. In this case, the surface area of the first surface 50a of the first inflatable portion 50 in the inflated state may be larger than the surface area of the third surface 60a of the second inflatable portion 60 in the inflated state. In addition, the volume of the first inflatable portion 50 in the inflated state may be larger than the volume of the second inflatable portion 60 in the inflated state.

In addition, both the first inflatable portion 50 and the second inflatable portion 60 according to the present embodiment are inflated by being injected with a fluid and formed using the same member. For this reason, when the external dimensions (L1, W1) of the first inflatable portion 50 and the external dimensions (L2, W2) of the second inflatable portion 60 are the same, a difference is not recognized at a glance, and there is a possibility that the first inflatable portion 50 and the second inflatable portion 60 will be mistaken (i.e., that the first inflatable portion 50 will be positioned to apply pressure to the ulnar artery 230 while the second inflatable portion 60 is positioned to apply pressure to the radial artery 210). However, as described above, when the respective inflatable portions 50 and 60 are formed such that the external dimensions (L1, W1) of the first inflatable portion 50 and the external dimensions (L2, W2) of the second inflatable portion 60 are different from each other, it is possible to rather easily distinguish between the first inflatable portion 50 and the second inflatable portion 60 having different appearance sizes.

In addition, a relationship between a length L3 of the first curved portion 42 and a length L4 of the second curved portion 43 along a longitudinal direction of the curved plate 40 corresponds to a relationship between the length L1 of the first inflatable portion 50 and the length L2 of the second inflatable portion 60. Specifically, as illustrated in FIG. 10 and FIG. 13, the length L3 of the first curved portion 42 provided on a side where the first inflatable portion 50 is located may be longer than the length L4 of the second curved portion 43 provided on a side where the second inflatable portion 60 is located. For this reason, when the hemostatic device 10 is mounted on the wrist 200, the first inflatable portion 50 and the second inflatable portion 60 may be pressed against the wrist 200 by conforming the first curved portion 42 and the second curved portion 43 to shapes of the first inflatable portion 50 and the second inflatable portion 60, which are inflated, respectively.

As illustrated in FIG. 10, the marker 70 is provided on the second surface 50b. When such a marker 70 is provided in the first inflatable portion 50, the first inflatable portion 50 may be relatively easily positioned with respect to the puncture site 220, and thus a position shift of the first inflatable portion 50 is suppressed.

A shape of the marker 70 is not particularly limited. Examples of the shape include a circle, a triangle, a rectangle, etc. In the present embodiment, the shape of the marker 70 is a rectangle.

A size of the marker 70 is not particularly limited. However, for example, when the shape of the marker 70 is the rectangle, a length of a side of the rectangular marker is preferably in a range of 1 to 4 mm. When the length of the side is 5 mm or more, the size of the marker 70 is larger when compared to a size of the puncture site 220, and thus it is difficult to position a central portion of the first inflatable portion 50 in the puncture site 220.

A material of the marker 70 is not particularly limited. Examples of the material for the marker 70 include an oily coloring agent such as ink, a resin kneaded with a pigment, etc.

A color of the marker 70 is not particularly limited when the color allows the first inflatable portion 50 to be positioned in the puncture site 220. However, a green-based color is preferable. When the green-based color is adopted, it is rather easy to visually recognize the marker 70 on blood or skin, and thus the first inflatable portion 50 is more easily positioned in the puncture site 220.

In addition, the marker 70 is preferably translucent or colored transparent. In this way, the puncture site 220 may be visually recognized from an outer surface side of the marker 70.

The manner in which the marker 70 is provided in the first inflatable portion 50 is not particularly limited. Examples of providing the marker at the first inflatable portion 50 include printing the marker 70 on the first inflatable portion 50, fusing the marker 70 to the first inflatable portion 50, applying an adhesive to one surface of the marker 70 to paste the marker 70 to the first inflatable portion 50, etc.

The marker 70 may be provided on the inner surface side of the first inflatable portion 50. In this instance, the marker 70 is preferably provided on an inner surface, etc. of the first inflatable portion 50 so as not to directly come into contact with the puncture site 220.

The first injection portion 80 and the second injection portion 81 are parts for injecting a fluid into the first inflatable portion 50 and the second inflatable portion 60, respectively, and are connected to the first inflatable portion 50 and the second inflatable portion 60, respectively, as illustrated in FIG. 9.

The first injection portion 80 includes a flexible first tube 82 having a proximal portion connected to the first inflatable portion 50 and a lumen communicating with an inside of the first inflatable portion 50, a first bag body 84 disposed at a distal portion of the first tube 82 to communicate with the lumen of the first tube 82, and a tube-shaped first connector 86 connected to the first bag body 84. A check valve (not illustrated) is incorporated in the first connector 86.

Similarly, the second injection portion 81 includes a flexible second tube 83 having a proximal portion connected to the second inflatable portion 60 and a lumen communicating with an inside of the second inflatable portion 60, a second bag body 85 disposed at a distal portion of the second tube 83 to communicate with the lumen of the second tube 83, and a tube-shaped second connector 87 connected to the second bag body 85. A check valve (not illustrated) may be incorporated in the second connector 87. The second tube 83 is preferably disposed on the same side as a side where the first tube 82 is disposed with respect to the band 20. In this way, it is possible to inject a fluid into the first tube 82 and the second tube 83 from the same side. For this reason, when the same syringe is used for the first tube 82 and the second tube 83, it is possible to easily perform an operation of inserting and withdrawing the syringe.

At the time of inflating (expanding) the first inflatable portion 50, a tip of a syringe (not illustrated) is inserted into the first connector 86 to open the check valve, and a plunger of this syringe is pushed to inject a fluid in the syringe into the first inflatable portion 50 through the first injection portion 80. When the first inflatable portion 50 expands, the first bag body 84 communicating with the first inflatable portion 50 through the first tube 82 also expands, and it is possible to visually confirm that the first inflatable portion 50 can be pressed without leakage of the fluid. When the tip of the syringe is withdrawn from the first connector 86 after the fluid is injected into the first inflatable portion 50, the check valve incorporated in the first connector 86 is closed to prevent leakage of the fluid, and an expanded state of the first inflatable portion 50 is maintained. When the same operation is performed with respect to the second injection portion 81 connected to the second inflatable portion 60, an expanded state of the second inflatable portion 60 is maintained.

Next, a description will be given of a manner of using the hemostatic device 10 according to the present embodiment.

Before the hemostatic device 10 is mounted on the wrist 200, the first inflatable portion 50 and the second inflatable portion 60 are in a state of not being inflated. When the wrist 200 is punctured, the puncture site 220 with respect to the radial artery 210 is normally biased to a thumb side of the right hand wrist 200. Normally, the introducer sheath is indwelled in the puncture site 220. The band 20 is wrapped around the wrist 200 in which the introducer sheath is indwelled, the first inflatable portion 50 and the band 20 are positioned such that the marker 70 provided in the first inflatable portion 50 overlaps the puncture site 220, and the male side 31 and the female side 32 of the hook and loop fastener 30 are brought into contact with each other and joined to each other, thereby mounting the band 20 on the wrist 200.

The hemostatic device 10 may be mounted on the wrist 200 such that the first injection portion 80 and the second injection portion 81 face a downstream side of a blood flow of the radial artery 210. In this way, the first injection portion 80 and the second injection portion 81 may be operated without interfering with manipulation on the upstream side of the wrist or a device (for example, a sphygmomanometer, etc.) located on the upstream side. In addition, when the hemostatic device 10 is mounted on the right hand wrist 200 such that the first injection portion 80 and the second injection portion 81 face the downstream side, the first inflatable portion 50 is located on the radial artery 210 biased to the thumb side of the wrist 200, and the second inflatable portion 60 is located around the ulnar artery 230. In the case of the artery, the upstream side of the blood vessel refers to a direction of the blood vessel approaching a heart. In addition, the downstream side of the blood vessel refers to a direction of the blood vessel away from the heart.

After the hemostatic device 10 is mounted on the wrist 200, the syringe (not illustrated) is connected to the first connector 86 of the first injection portion 80, the fluid is injected into the first inflatable portion 50 as described above, and the first inflatable portion 50 is inflated to press the puncture site 220 as illustrated in FIG. 13 and FIG. 14. A degree of inflation of the first inflatable portion 50, that is, a pressing force applied to the puncture site 220 located in the radial artery 210 may be rather easily adjusted depending on the case according to an injection amount of the fluid at this time.

After the first inflatable portion 50 is inflated, the syringe is detached from the first connector 86. Then, the introducer sheath is withdrawn from the puncture site 220. In this way, the first inflatable portion 50 maintains an inflated state, and a state of pressing the puncture site 220 is maintained.

Figure 15:
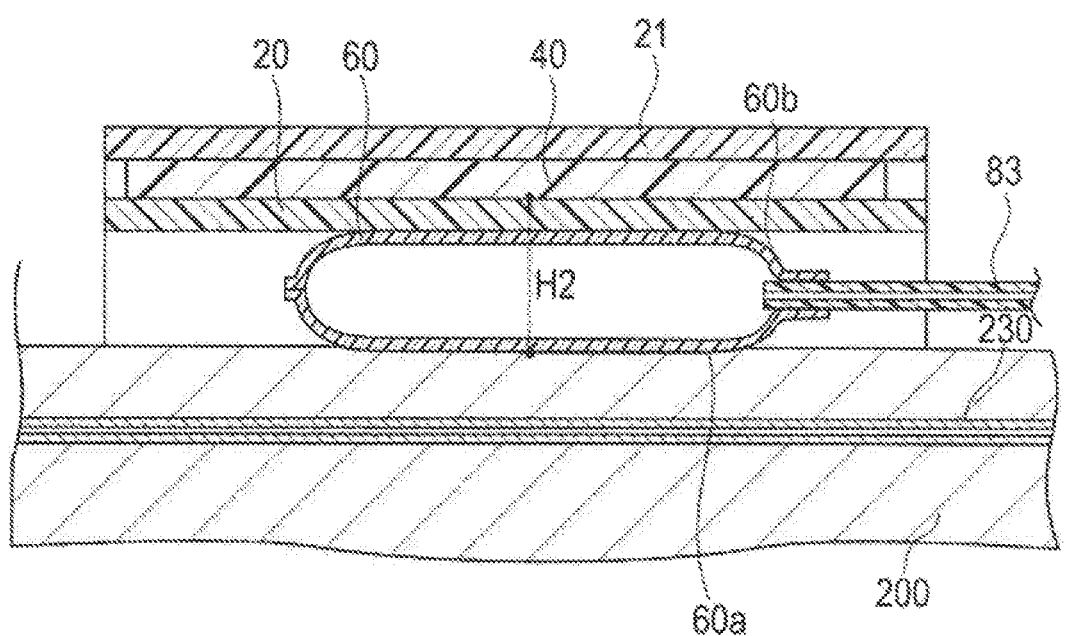
FIG. 15 is a cross-sectional view taken along the section line 15-15 of FIG. 12.

Subsequently, the syringe (not illustrated) is connected to the second connector 87 of the second injection portion 81, the fluid is injected into the second inflatable portion 60 as described above, and the second inflatable portion 60 is inflated to press the vicinity of the ulnar artery 230 as illustrated in FIG. 13 and FIG. 15. A degree of inflation of the second inflatable portion 60, that is, a pressing force applied to the vicinity of the ulnar artery 230 may be rather easily adjusted according to an injection amount of the fluid at this time.

When the first inflatable portion 50 and the second inflatable portion 60 are inflated, the curved plate 40 is separated from the body surface of the wrist 200 and hardly comes into contact with the wrist 200. In addition, when the first inflatable portion 50 and the second inflatable portion 60 are inflated after the hemostatic device 10 is mounted, inflation of the first inflatable portion 50 and the second inflatable portion 60 in a direction away from the body surface of the wrist 200 is suppressed by the curved plate 40, and a pressing force of the first inflatable portion 50 and the second inflatable portion 60 is concentrated on the wrist 200 side. For this reason, a pressing force from the first inflatable portion 50 intensively acts on the vicinity of the puncture site 220, and thus the hemostatic effect may be improved.

In addition, when the first inflatable portion 50 presses the radial artery 210, the second inflatable portion 60 may press the ulnar artery 230, thereby preventing an excessive increase in the blood flow flowing to the ulnar artery 230, and suppressing a decrease in the blood flow rate of the radial artery 210. In this way, occlusion of the blood vessel may be prevented, and a decrease in the amount of the platelets, etc. may be suppressed, thereby performing hemostasis at the puncture site 220 in a relatively short time.

In addition, as illustrated in FIG. 13, FIG. 14, and FIG. 15, in a state in which the hemostatic device 10 is mounted on the wrist 200, the respective inflatable portions 50 and 60 are inflated until a length of a perpendicular line H1 indicating an indication of an inflation state of the first inflatable portion 50 becomes longer than a length of a perpendicular line H2 indicating an indication of an inflation state of the second inflatable portion 60. In this way, when compared to a part of the second inflatable portion 60 coming into contact with the wrist, a part of the first inflatable portion 50 coming into contact with the wrist is convexly deformed toward the wrist and presses the puncture site 220 and the vicinity thereof with a larger pressing force than a pressing force applied to the ulnar artery 230 by the second inflatable portion 60.

The pressing force of the first inflatable portion 50 and the second inflatable portion 60 may be adjusted by adjusting the amount of the fluid injected into the first inflatable portion 50 and the second inflatable portion 60 depending on the progress of hemostasis or the elapsed time.

When hemostasis is completed, the pressing force of the first inflatable portion 50 to the puncture site 220 is further reduced and the hemostatic device 10 is removed.

When hemostasis in the puncture site 220 is completed and the hemostatic device 10 is removed, the first inflatable portion 50 is contracted, and then the male side 31 and the female side 32 of the hook and loop fastener 30 are peeled off or separated to remove the hemostatic device 10 from the wrist 200. The first inflatable portion 50 may not be contracted when the hemostatic device 10 is removed.

As described above, the hemostatic device 10 according to the present embodiment includes the flexible band 20 that can be wrapped around the wrist in which the radial artery 210 and the ulnar artery 230 run or are located, the hook and loop fastener 30 that secures the band 20 to the wrist 200 in a wrapped state, the curved plate 40 held by the band 20 and formed using a harder material than the material forming the band 20, the first inflatable portion 50 connected to the band 20 and allowed to press the puncture site 220 of the radial artery 210 by being inflated in response to injection of the fluid, and the second inflatable portion 60 disposed at a different position from that of the first inflatable portion 50 in the longitudinal direction of the band 20 and allowed to press the ulnar artery 230. The first inflatable portion 50 has the first surface 50a disposed on the wrist 200 side and the second surface 50b disposed on the band 20 side. The second inflatable portion 60 has the third surface 60a disposed on the wrist 200 side and the fourth surface 60b disposed on the band 20 side. In a state in which at least a portion of the second surface 50b in the first inflatable portion 50 and at least a portion of the fourth surface 60b in the second inflatable portion 60 are brought into contact with a range of the band 20 in which the curved plate 40 is disposed, the length H1 of the perpendicular line from the curved plate 40 to the first surface 50a at the time of inflating the first inflatable portion 50 may be longer than the length H2 of the perpendicular line from the curved plate 40 to the third surface 60a at the time of inflating the second inflatable portion 60.

According to the hemostatic device 10 configured as described above, the hemostatic effect may be enhanced by moderately suppressing a decrease in the blood flow rate of the radial artery 210. In addition, the length H1 of the perpendicular line from the curved plate 40 to the first surface 50a at the time of inflating the first inflatable portion 50 may be longer than the length H2 of the perpendicular line from the curved plate 40 to the third surface 60a at the time of inflating the second inflatable portion 60. For this reason, in the state in which the hemostatic device 10 is mounted on the wrist 200, a pressing force applied to the ulnar artery 230 by the second inflatable portion 60 may be smaller than a pressing force applied to the puncture site 220 by the first inflatable portion 50. As a result, it is possible to reduce numbness or pain caused by pressing the ulnar artery 230 by decreasing the pressing force applied to the ulnar artery 230 by the second inflatable portion 60 while ensuring the pressing force applied to the puncture site 220 by the first inflatable portion 50.

In addition, the surface area of the first surface 50a of the first inflatable portion 50 in the inflated state may be larger than the surface area of the third surface 60a of the second inflatable portion 60 in the inflated state. For this reason, in the state in which the hemostatic device 10 is mounted on the wrist 200, an area of a part in which the first inflatable portion 50 comes into contact with the wrist 200 becomes larger than an area of a part in which the second inflatable portion 60 comes into contact with the wrist 200. As a result, it is possible to ensure the pressing force applied to the puncture site 220 by the first inflatable portion 50 and stably press the puncture site 220 by pressing a relatively extensive range, and it is possible to decrease the pressing force applied to the ulnar artery 230 by the second inflatable portion 60 and reduce numbness or pain caused by pressing the ulnar artery 230.

In addition, the length L2 of the second inflatable portion 60 along the longitudinal direction of the band 20 may be shorter than the length of the first inflatable portion 50 along the longitudinal direction of the band 20. For this reason, it is possible to narrow a range in a part (a tendon, a nerve, etc.) other than the ulnar artery 230 pressed by the second inflatable portion 60 while ensuring a range pressed by the first inflatable portion 50. As a result, it is possible to reduce numbness or pain caused by pressing the ulnar artery 230.

In addition, the second inflatable portion 60 can be inflated by injection of a fluid, and the volume of the first inflatable portion 50 in the inflated state may be larger than the volume of the second inflatable portion 60 in the inflated state. When the volume in the inflated state is large, the wrist 200 is more strongly pressed. Thus, when the volume of the first inflatable portion 50 in the inflated state is larger than the volume of the second inflatable portion 60, it is possible to decrease the pressing force applied to the ulnar artery 230 by the second inflatable portion 60 while ensuring the pressing force applied to the puncture site 220 by the first inflatable portion 50.

Modification of Second Embodiment

Figure 16:
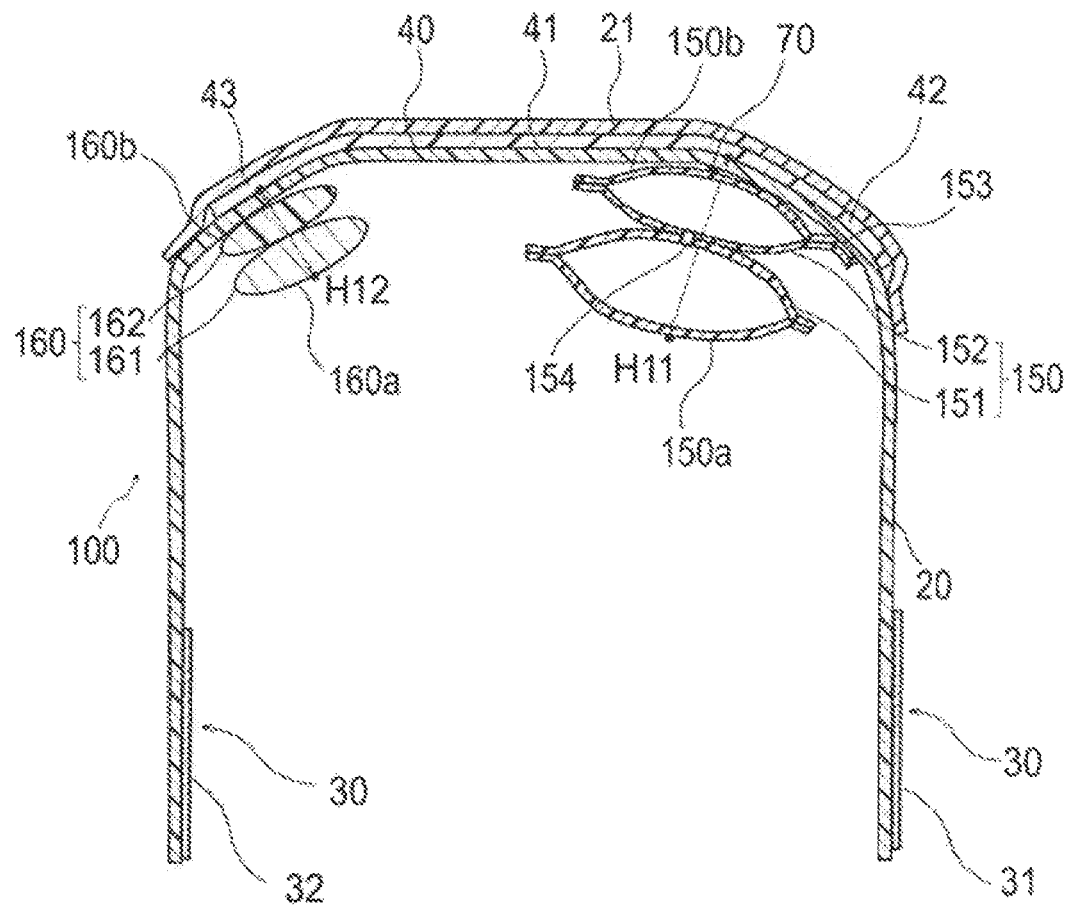
FIG. 16 is a schematic view illustrating a hemostatic device according to a modification of the second embodiment.

In the hemostatic device 10 according to the second embodiment, a member (inflatable portion) that presses the puncture site 220 includes the single first inflatable portion 50 that inflates by injection of a fluid. Meanwhile, as illustrated in FIG. 16, a hemostatic device 100 according to a modification of the second embodiment has a feature in that a fluid is injected in common with the second embodiment. However, the hemostatic device 100 is different from the second embodiment in that a member (inflatable portion 150) that presses the puncture site 220 includes two members corresponding to a main compression portion 151 and an auxiliary compressing portion 152.

In addition, in the hemostatic device 10 according to a second embodiment, the member (pressing portion) that presses the ulnar artery 230 includes the single second inflatable portion 60 that can inflate by injection of a fluid. On the other hand, in the hemostatic device 100 according to the modification of the second embodiment, a member (pressing member 160) that presses the ulnar artery 230 includes two members corresponding to a hard member (relatively hard member) 161 and a soft member (relatively soft member) 162. Other aspects and configurations of the modification of the second embodiment are substantially the same as in the second embodiment. Hereinafter, a detailed description will be given of the hemostatic device 100 according to the modification of the second embodiment. In the description below, features that are the same or similar to those described above are identified by the same reference numerals and a detailed description of such features is not repeated.

As illustrated in FIG. 16, the inflatable portion 150 includes the main compression portion 151 that presses the puncture site 220 of the radial artery 210 and the auxiliary compressing portion 152 disposed to overlap a part between the main compression portion 151 and the band 20. The main compression portion 151 and the auxiliary compressing portion 152 are located to overlap the vicinity of a part between the first curved portion 42 and the central portion 41.

The main compression portion 151 and the auxiliary compressing portion 152 inflate by injection of a fluid (gas such as air or liquid). The main compression portion 151 and the auxiliary compressing portion 152 communicate with each other, a communication path 154 that can allow communication between an inside of the main compression portion 151 and an inside of the auxiliary compressing portion 152 is provided, and the same injection portion (not illustrated) as that of the second embodiment is provided in one of the compression portions. For this reason, when one of the main compression portion 151 or the auxiliary compressing portion 152 is injected with a fluid and inflated, the other one inflates together. The inflated main compression portion 151 presses the puncture site 220 located in the radial artery 210 of the wrist 200. The inflated auxiliary compressing portion 152 presses the main compression portion 151 to adjust a pressing direction of the main compression portion 151. The auxiliary compressing portion is not limited to a portion inflated by being injected with a fluid as in the second embodiment. For example, it is possible to use a sponge-like substance, an elastic material, an aggregate of fibers such as cotton, or a combination thereof.

A constituent material forming the main compression portion 151 and the auxiliary compressing portion 152 is not particularly limited as long as the material has flexibility. For example, it is possible to use the same material as the constituent material forming the band 20 of the second embodiment mentioned above. In addition, the main compression portion 151 and the auxiliary compressing portion 152 are preferably made of the same or a similar material as or to that of the band 20. In this way, joining the main compression portion 151 and the auxiliary compressing portion 152 to the band 20 by fusing may be rather easily performed, and manufacture may be relatively easily performed.

Similar to the band 20 and the curved plate 40, the main compression portion 151 and the auxiliary compressing portion 152 are preferably substantially transparent. In this way, the puncture site 220 may be visually recognized from the outer surface side, and a marker 70 provided in the auxiliary compressing portion 152 may be relatively easily positioned in the puncture site 220.

Similar to the first inflatable portion 50 according to the second embodiment, structures of the main compression portion 151 and the auxiliary compressing portion 152 may be formed in a shape of a bag by overlapping two rectangular sheet materials and joining edge portions using a method such as fusing, adhesion, etc.

The auxiliary compressing portion 152 may be connected to the band 20 through a holding portion 153 having flexibility. The holding portion 153 is preferably provided on the first curved portion 42 side of the curved plate 40. In addition, the holding portion 153 is preferably made of the same material as that of the main compression portion 151 and the auxiliary compressing portion 152. In this way, joining to the band 20 by fusing may be rather easily performed, and manufacture may be rather easily accomplished.

The pressing member 160 includes the hard member (relatively harder member) 161 that presses the vicinity of the ulnar artery 230 and the soft member (relatively softer member) 162 which is softer than the hard member 161 and disposed to overlap a part between the hard member 161 and the band 20. The hard member 161 and the soft member 162 overlap the vicinity of a part between the second curved portion 43 and the central portion 41.

For example, the hard member 161 may be made of a hard material (relatively harder member) such as metal, plastic, etc. The soft member (relatively softer member) 162 may be softer than the hard member 161. For example, it is possible to use a sponge-like substance, an elastic material, an aggregate of fibers such as cotton, or a material obtained by combining these materials. In addition, for example, the soft member 162 may be configured to be inflated by being injected with a fluid (air, liquid, etc.). The hard member 161 presses the ulnar artery 230. The soft member 162 mitigates a pressing force applied to the hard member 161 by the curved plate 40 between the curved plate 40 and the hard member 161.

The external shapes of ach of the hard member 161 and the soft member 162 correspond to a cylindrical shape having an elliptical cross section. However, so long as the ulnar artery 230 can be pressed, the external shapes of the hard member 161 and the soft member 162 are not limited to the cylindrical shape. For example, it is possible to adopt a polygonal prism such as a quadrangular prism, a triangular prism, etc.

The hard member 161 and the soft member 162 are joined to each other using a method such as fusing (heat-fusing, high-frequency fusing, ultrasonic fusing, etc.), adhesion (adhesion by an adhesive or a solvent), etc. The soft member 162 and the band 20 are joined to each other using the same method.

In the present modification, a surface of the inflatable portion 150 disposed on the wrist 200 side (a surface of the main compression portion 151 disposed on the wrist 200 side) is a first surface 150a, and a surface of the inflatable portion 150 disposed on the band 20 side (a surface of the auxiliary compressing portion 152 disposed on the wrist 200 side) is a second surface 150b. In addition, a surface of the pressing member 160 disposed on the wrist 200 side (a surface of the hard member 161 disposed on the wrist 200 side) is a third surface 160a, and a surface of the pressing member 160 disposed on the band 20 side (a surface of the soft member 162 disposed on the wrist 200 side) is a fourth surface 160b. In a state in which at least a part of the second surface 150b in the inflatable portion 150 and at least a part of the fourth surface 160b in the pressing member 160 are brought into contact with a range of the band 20 in which the curved plate 40 is disposed, a length H11 of a perpendicular line from the curved plate 40 to the first surface 150a at the time of inflating the inflatable portion 150 is longer than a length H12 of a perpendicular line from the curved plate 40 to the third surface 160a.

According to the hemostatic device 100 configured as described above, it is possible to enhance the hemostatic effect by moderately suppressing a decrease in the blood flow rate of the radial artery 210. In addition, the length H11 of the perpendicular line from the curved plate 40 to the first surface 150a at the time of inflating the inflatable portion 150 may be longer than the length H12 of the perpendicular line from the curved plate 40 to the third surface 160a of the pressing member 160. For this reason, in the state in which the hemostatic device 100 is mounted on the wrist 200, a pressing force applied to the ulnar artery 230 by the pressing member 160 may be smaller than a pressing force applied to the puncture site 220 by the inflatable portion 150. As a result, it is possible to reduce numbness or pain caused by pressing the ulnar artery 230 by decreasing the pressing force applied to the ulnar artery 230 by the pressing member 160 while ensuring the pressing force applied to the puncture site 220 by the inflatable portion 150.

In addition, the pressing member 160 includes the soft member 162 between the hard member 161 and the curved plate 40, and the soft member 162 mitigates the pressing force applied from the curved plate 40 to the hard member 161 at the time of mounting the hemostatic device 100 on the wrist 200. In this way, when the wrist 200 is pressed by the hard member 161 which is solid, it is possible to reduce numbness or pain caused by pressing the ulnar artery 230 by providing the soft member 162 between the hard member 161 and the curved plate 40.

As described above in the modification of the second embodiment, when each of the inflatable portion and the pressing member has a structure in which a plurality of members is stacked, each surface on the wrist 200 side in a member disposed closest to the wrist 200 side may be set to the first surface or the third surface, each surface on the band 20 side in a member disposed closest to the band 20 side may be set to the second surface or the fourth surface, and the above-described length relationship of the perpendicular lines may be satisfied.

The hemostatic devices according to the second embodiment and the modification of the second embodiment described above may be appropriately modified while still being within the scope of the description in claims.

For example, each portion included in the hemostatic device may be replaced with a portion having an arbitrary configuration capable of exerting the same function. In addition, an arbitrary component may be added.

In addition, the invention is not limited to the hemostatic device used by being mounted on the wrist, and is applicable to a hemostatic device used by being mounted on any part of the arm in which the radial artery and the ulnar artery run.

In addition, shapes of the members (the first inflatable portion and the main compression portion) that press the puncture site, the auxiliary member (the auxiliary compressing portion), and the member (the second inflatable portion) that presses the ulnar artery in a state of not being inflated are not limited to the rectangle. For example, the shapes may be a circle, an ellipse, and a polygon such as a pentagon.

In addition, the marker may not be provided in the inflatable portion, and may be provided in the band, the curved plate, and the auxiliary compressing portion. In addition, the marker is more preferably provided to overlap the central portion of the inflatable portion.

In addition, similar to the pressing member of the hemostatic device according to the first embodiment described above, in the pressing member (second inflatable portion) of the hemostatic device according to the second embodiment and the pressing member of the hemostatic device according to the modification of the second embodiment, the dimension (length) along the longitudinal direction of the band may be shorter than the dimension (width) along the direction orthogonal to the longitudinal direction of the band.

In addition, in the pressing member (second inflatable portion) of the hemostatic device according to the second embodiment and the pressing member of the hemostatic device according to the modification of the second embodiment, it is possible to provide a projection provided in a pressing member of a hemostatic device according to a third embodiment described below. When the projection is provided in the pressing member (second inflatable portion) of the hemostatic device according to the second embodiment and the pressing member of the hemostatic device according to the modification of the second embodiment as described above, a surface disposed on the arm side of the projection corresponds to a third surface, and a length of a perpendicular line on the inflatable portion side (a length of a perpendicular line from the support plate to the first surface) L1 may be longer than a length of a perpendicular line on the pressing member side (a length of a perpendicular line from the support plate to the third surface) L2.

Third Embodiment

Next, a description will be given of the hemostatic device according to the third embodiment of the hemostatic device disclosed here.

Figure 20A:
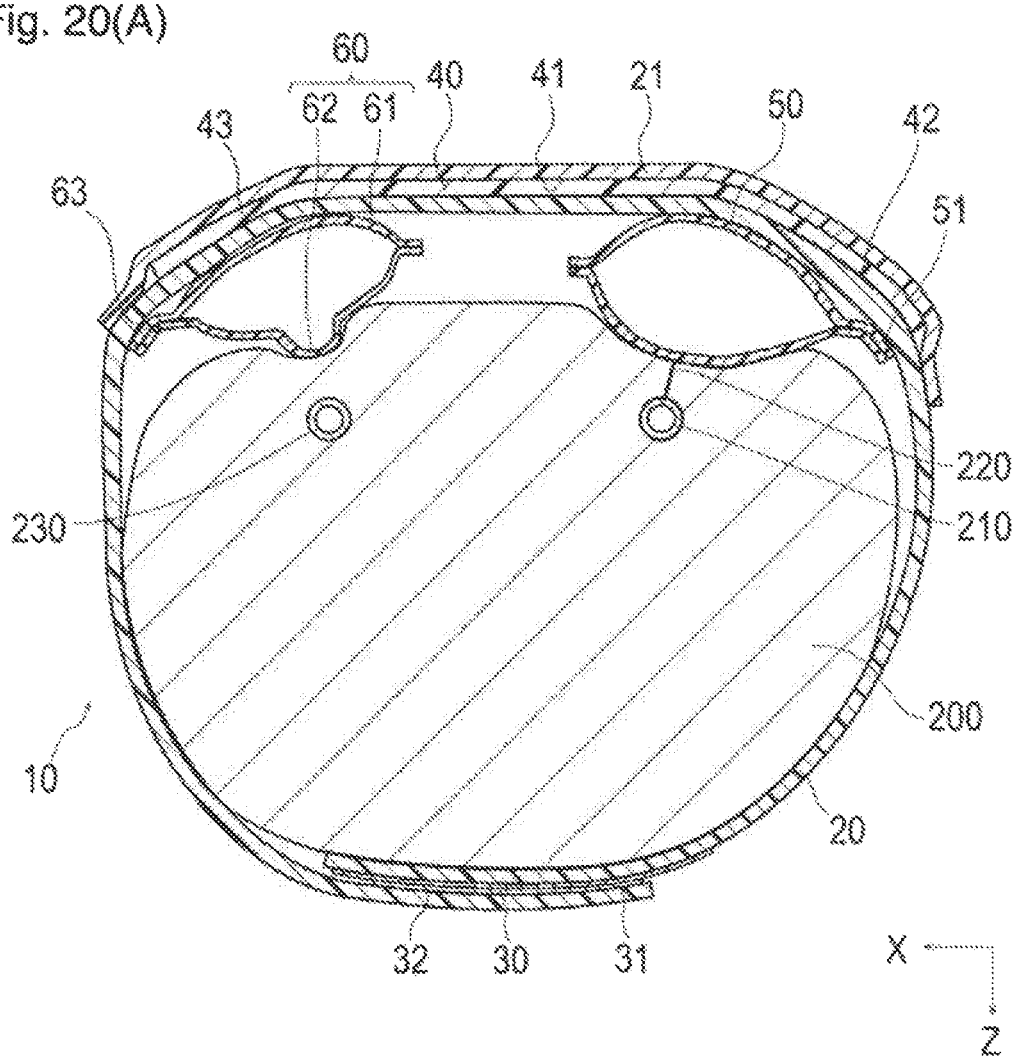
FIG. 20(A) is a cross-sectional view taken along the section line 20A-20A of FIG. 19.

As illustrated in FIG. 20(A), the hemostatic device 10 according to the third embodiment, representing another embodiment of the inventive hemostatic device disclosed here, is used to perform hemostasis at a puncture site 220 after withdrawing an introducer sheath indwelled in the puncture site 220 (corresponding to a part to be subjected to hemostasis) formed in a radial artery 210 of a wrist 200 to insert a catheter, etc. performing treatment/examination, etc. into a blood vessel.

Figure 17:
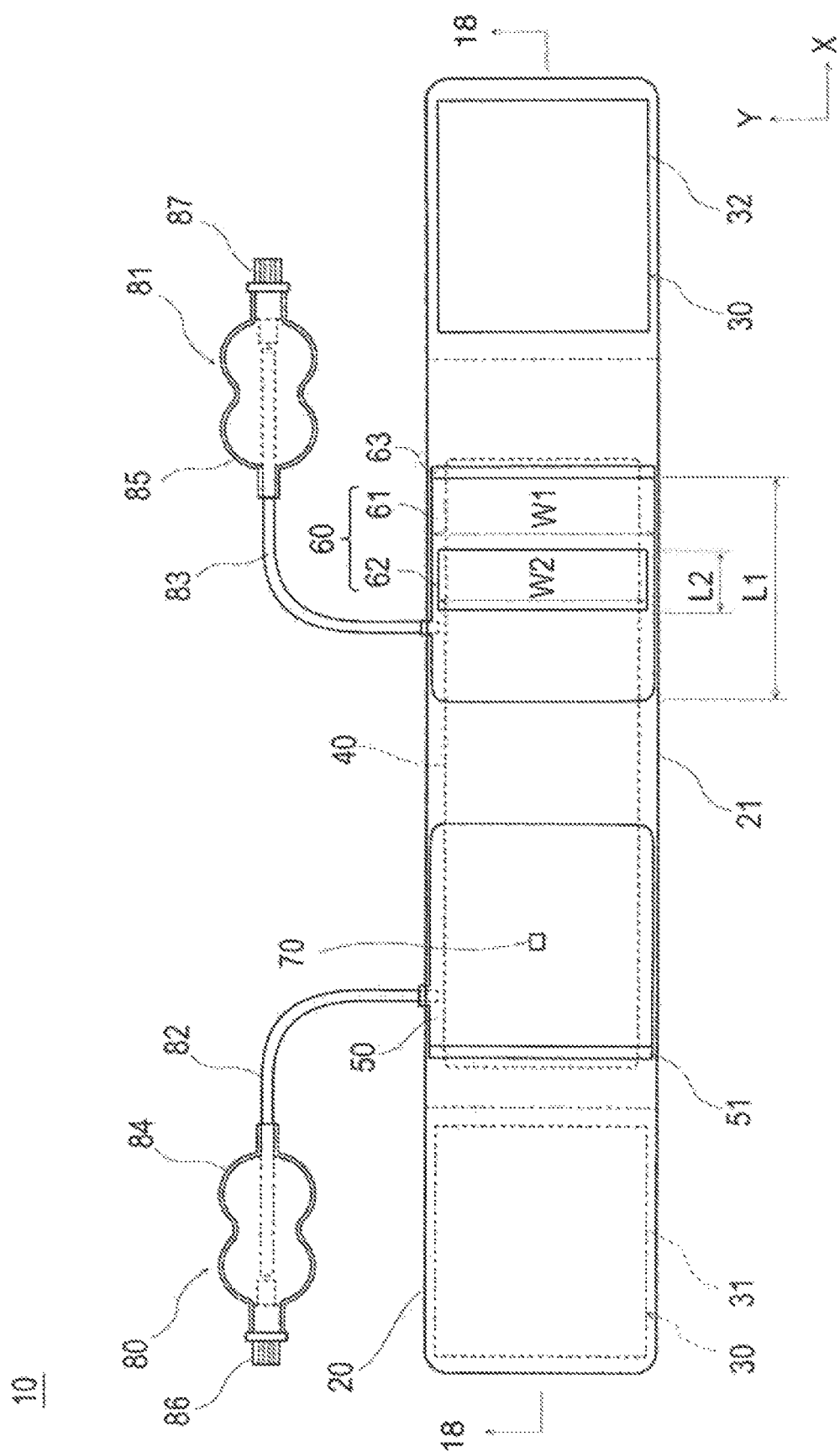
FIG. 17 is a plan view of a hemostatic device according to a third embodiment viewed from an inner surface side.
Figure 18:
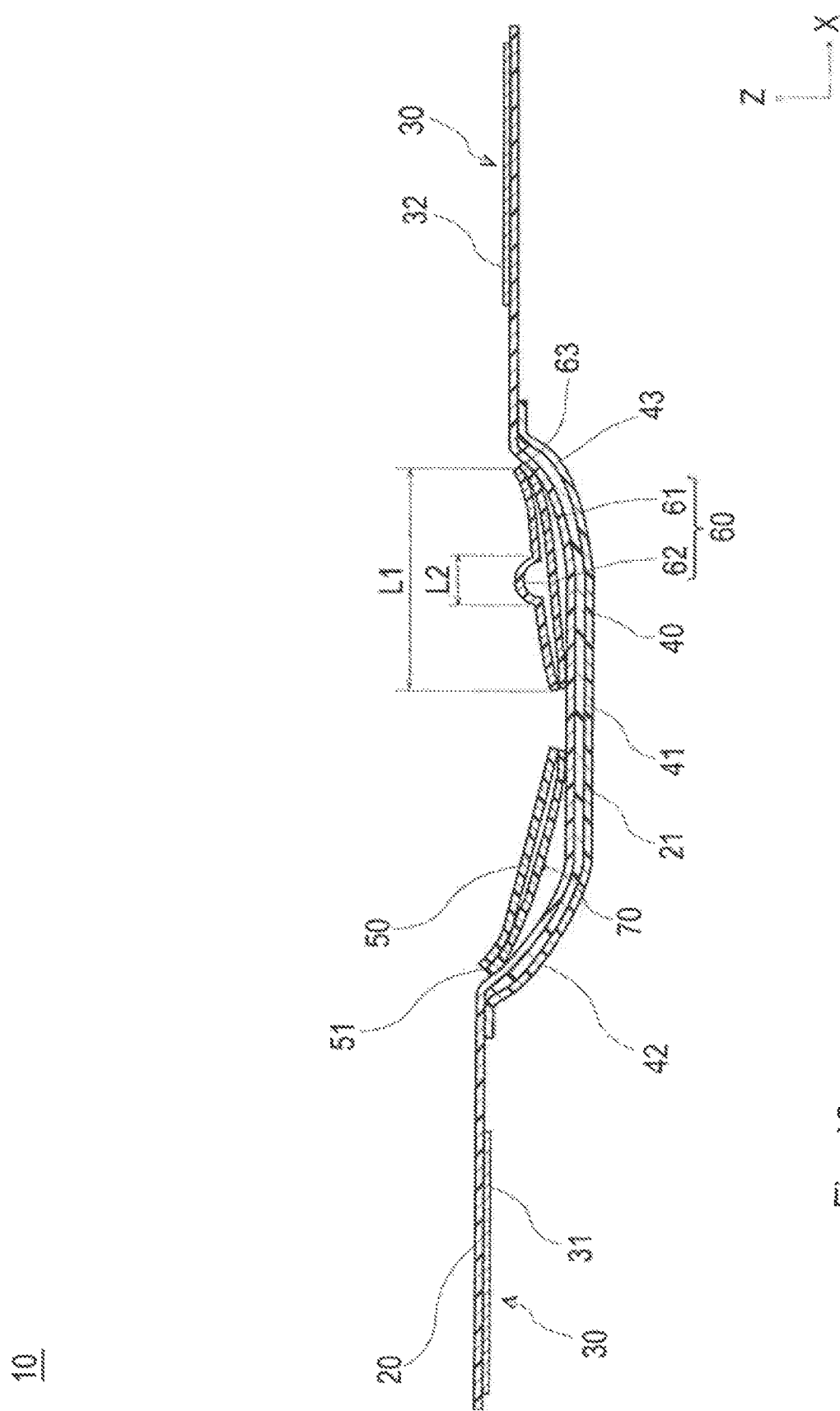
FIG. 18 is a cross-sectional view taken along the section line 18-18 of FIG. 17.

As illustrated in FIG. 17 and FIG. 18, the hemostatic device 10 includes a band 20 for wrapping around the wrist 200, a hook and loop fastener 30 (corresponding to a securing portion) for securing the band 20 in a state of being wrapped around the wrist 200, a curved plate 40, an inflatable portion or inflatable element/member 50, a pressing member 60, a marker 70, a first injection portion 80, and a second injection portion 81.

In this description, a side (mounting surface side) of the band 20 facing a body surface of the wrist 200 is referred to as an "inner surface side", and an opposite side thereof is referred to as an "outer surface side" when the band 20 is wrapped around the wrist 200.

In addition, in the drawings, a longitudinal direction of the band 20 is indicated as an arrow X, a direction orthogonal to the longitudinal direction of the band 20 is indicated as an arrow Y, and a direction orthogonal to the arrow Y and the arrow X is indicated as an arrow Z.

The band 20 may be a flexible band-shaped member. As illustrated in FIG. 20(A), the band 20 may be wrapped around an outer periphery of the wrist 200 substantially once. As illustrated in FIG. 18, a curved plate holding portion 21 that holds the curved plate 40 is formed at a central portion of the band 20. The curved plate holding portion 21 is doubled by separate band-shaped members joined to an outer surface side (or inner surface side) using a method such as fusing (heat-fusing, high-frequency fusing, ultrasonic fusing, etc.), adhesion (adhesion by an adhesive or a solvent), etc. and holds the curved plate 40 inserted into a gap therebetween.

Figure 19:
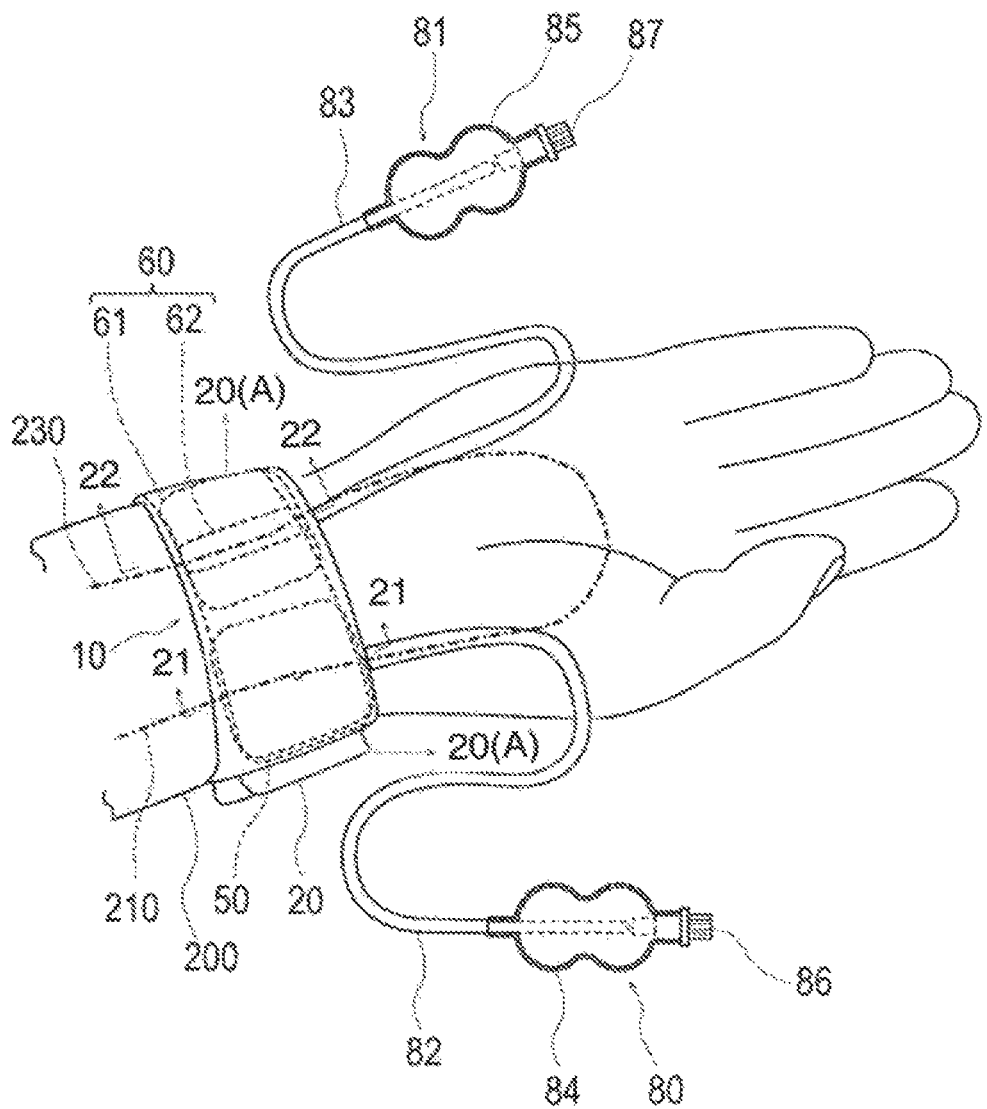
FIG. 19 is a perspective view illustrating a state of mounting the hemostatic device according to the third embodiment.

A male side (or a female side) 31 of the hook and loop fastener 30 generally referred to as Magic Tape (registered trademark), etc. may be disposed on the outer surface side of the band 20 near a left end of FIG. 17, and a female side (or a male side) 32 of the hook and loop fastener 30 may be disposed on the inner surface side of the band 20 near a right end of FIG. 17. As illustrated in FIG. 19 and FIG. 20(A), the band 20 may be wrapped around the wrist 200, and the male side 31 and the female side 32 are joined together, thereby mounting the band 20 on the wrist 200. Means for securing the band 20 to the wrist 200 in a wrapped state is not limited to the hook and loop fastener 30. For example, the means may correspond to a snap, a button, a clip, or a frame member passing an end portion of the band 20.

A constituent material of the band 20 is not particularly limited as long as the material has flexibility, and examples thereof include polyvinyl chloride, polyolefins such as polyethylene, polypropylene, polybutadiene and ethylene-vinyl acetate copolymers (EVA), polyesters such as polyethylene terephthalate (PET) and polybutylene terephthalate (PBT), polyvinylidene chloride, silicone, polyurethane, various thermoplastic elastomers such as polyamide elastomers, polyurethane elastomers and polyester elastomers, and an arbitrary combination of the above (blend resin, polymer alloy, laminate, etc.).

The band 20 is preferably substantially transparent. However, the band 20 may not be transparent, and may be translucent or colored transparent. In this way, the puncture site 220 may be visually recognized from the outer surface side, and the marker 70 described below may be easily positioned in the puncture site 220.

As illustrated in FIG. 18, the curved plate 40 may be held in the band 20 by being inserted into or positioned in the doubly formed curved plate holding portion 21 of the band 20. The curved plate 40 may be made of a harder material than the material of the band 20 and maintains a substantially constant shape.

The curved plate 40 may have a shape elongated in the longitudinal direction of the band 20 (a direction of the arrow X). A central portion 41 of the curved plate 40 in the longitudinal direction may have a flat plate shape almost without being curved, and a first curved portion 42 (left side of FIG. 18) and a second curved portion 43 (right side of FIG. 18) curved toward an inner peripheral side and along the longitudinal direction of the band 20 (a circumferential direction of the wrist 200) are formed at both sides of the central portion 41, respectively.

A constituent material forming the curved plate 40 is not particularly limited as long as the puncture site 220 can be visually recognized. Examples of the material include acrylic resins, polyvinyl chloride (particularly rigid polyvinyl chloride), polyolefins such as polyethylene, polypropylene and polybutadiene, polystyrene, poly(4-methyl pentene-1), polycarbonates, ABS resins, polymethyl methacrylate (PMMA), polyacetals, polyarylates, polyacrylonitriles, polyvinylidene fluorides, ionomers, acrylonitrile-butadiene-styrene copolymers, polyesters such as polyethylene terephthalate (PET) and polybutylene terephthalate (PBT), butadiene-styrene copolymers, aromatic or aliphatic polyamides, and fluorocarbon resins such as polytetrafluoroethylene.

Similar to the band 20, the curved plate 40 is preferably substantially transparent. However, the curved plate 40 may not be transparent, and may be translucent or colored transparent. In this way, the puncture site 220 may be reliably visually recognized from the outer surface side, and the marker 70 described below may be easily positioned in the puncture site 220. The curved plate 40 may not have a non-curved part such as the central portion 41, that is, may be curved over an entire length of the plate.

The inflatable portion 50 and the pressing member 60 are connected to the band 20. The inflatable portion 50 and the pressing member 60 inflate by being injected with a fluid (gas such as air or liquid). The inflatable portion 50 presses the puncture site 220 located in the radial artery 210 of the wrist 200. The pressing member 60 presses the ulnar artery 230 by pressing the body surface of the wrist 200.

As illustrated in FIG. 18, the inflatable portion 50 is located to overlap the vicinity of a part between the first curved portion 42 and the central portion 41.

A constituent material forming the inflatable portion 50 is not particularly limited as long as the material has flexibility. For example, it is possible to use the same material as the constituent material forming the band 20 mentioned above.

Similar to the band 20 and the curved plate 40, the inflatable portion 50 is preferably substantially transparent. In this way, the puncture site 220 may be visually recognized from the outer surface side, and the marker 70 described below may be rather easily positioned in the puncture site 220.

For example, as illustrated in FIG. 18, a structure of the inflatable portion 50 may be formed in a shape of a bag obtained by overlapping two sheet materials made of the above-described materials and joining edge portions using a method such as fusing, adhesion, etc. As illustrated in FIG. 17, an external shape of the inflatable portion 50 is a rectangle in a state of not being inflated.

As illustrated in FIG. 18, the inflatable portion 50 is connected to the band 20 through a first holding portion 51 having flexibility. The first holding portion 51 is preferably provided on the first curved portion 42 side of the curved plate 40. In addition, the first holding portion 51 is preferably made of the same material as that of the inflatable portion 50. In this way, joining to the band 20 by fusing may be relatively easily performed, and manufacture may be rather easily accomplished.

As illustrated in FIG. 18, the pressing member 60 is disposed at a different position from that of the inflatable portion 50 in the longitudinal direction of the band 20. Specifically, the pressing member 60 is disposed to overlap the vicinity of a part between the second curved portion 43 and the central portion 41.

The pressing member 60 is configured to be able to inflate by being injected with a fluid. The pressing member 60 includes a main body 61 forming a main part of the pressing member 60 and a projection 62 communicating with the main body 61 so as to inflate in response to injection of a fluid. In a state in which the main body 61 and the projection 62 inflate, the projection 62 includes a part protruding with respect to the main body 61. That is, in the inflated state, the projection 62 projects outwardly away from the main body 61. The main body 61 and the projection 62 are made of the same material and integrally formed, respectively.

As illustrated in FIG. 17, and FIG. 18, a length L2 of the projection 62 along the longitudinal direction of the band 20 is shorter than a length L1 of the main body 61 along the longitudinal direction of the band 20. More preferably, the length L2 of the projection 62 along the longitudinal direction of the band 20 is less than or equal to half the length L1 of the main body 61 along the longitudinal direction of the band 20. In this way, since the length L1 of the main body 61 disposed on the outer surface side is longer than the length L2 of the projection 62, it is possible to apply a pressing force to the projection 62 over the whole of the band 20 in width direction. Therefore, when the pressing member 60 is inflated, the projection 62 is held on the inner surface side of the main body 61, and a pressing direction of the projection 62 is defined based on a pressing direction of the main body 61. In this way, it is possible to prevent the projection 62 from pressing the wrist 200 in an unintended direction.

Figure 20B:
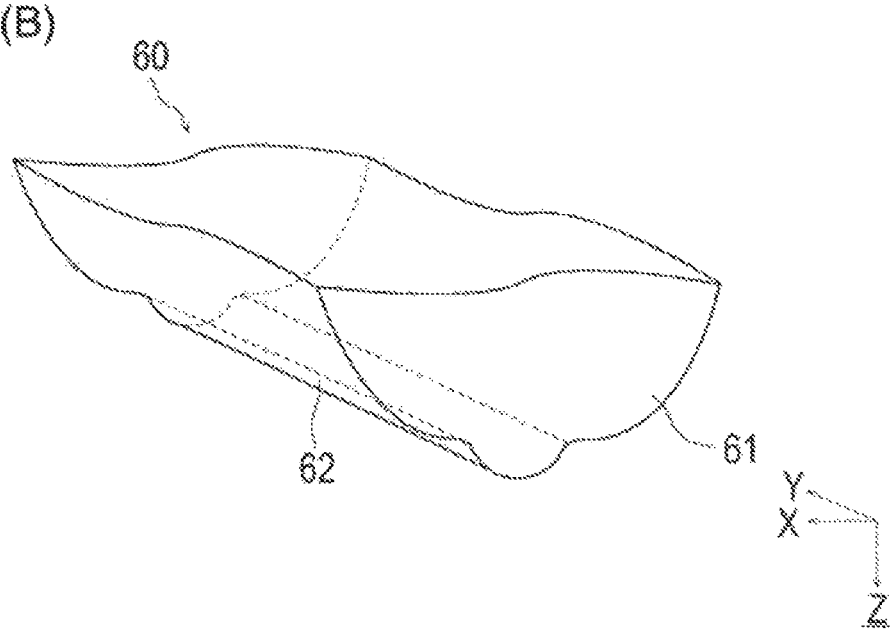
FIG. 20(B) is a perspective view schematically illustrating a pressing member.

The projection 62 may be formed in a convex shape as illustrated in FIG. 18 and FIG. 20(A) and may have a shape continuously extending along a width direction of the band 20 (a direction of the arrow Y) as illustrated in FIG. 17 and FIG. 20(B). In this way, a part of the projection 62 coming into contact with the wrist 200 may have a shape extending along running (direction of extent) of the ulnar artery 230.

In addition, as illustrated in FIG. 17, a length W2 of the projection 62 along the width direction of the band 20 may be less than or equal to a length W1 of the main body 61. In this way, since the length W2 of the projection 62 is relatively short, an area of the projection 62 coming into contact with the wrist 200 decreases correspondingly, and it is possible to narrow a range pressed by the pressing member 60. As a result, it is possible to restrict pressing a part other than the ulnar artery 230 such as a tendon, a nerve, etc. around the ulnar artery 230, and to reduce occurrence of numbness or pain on the wrist 200 due to pressing over a long period of time.

In addition, the length L2 of the projection 62 along the longitudinal direction of the band 20 may be shorter than the length W2 of the projection 62 along the width direction of the band 20. For this reason, a part of the pressing member 60 coming into contact with the wrist 200 may have a shape extending along running (direction of extent) of the ulnar artery 230. As a result, it is possible to further narrow a range of a part other than the ulnar artery 230 (a tendon, a nerve, etc.) pressed by the pressing member 60 while favorably pressing the ulnar artery 230. For this reason, it is possible to reduce numbness or pain at the time of using the hemostatic device 10.

As illustrated in FIG. 18, the pressing member 60 may be connected to the band 20 through a second holding portion 63 having flexibility. The second holding portion 63 is preferably provided on the second curved portion 43 side of the curved plate 40. In addition, the second holding portion 63 may preferably made of the same material as that of the pressing member 60. In this way, joining the second holding portion 63 to the band 20 by fusing may be rather easily performed, and manufacture may be relatively accomplished.

Similar to the inflatable portion 50, a constituent material forming the pressing member 60 preferably corresponds to a material having flexibility. For example, it is possible to use the same material as the constituent material forming the band 20 mentioned above. Similar to the band 20, the curved plate 40, and the inflatable portion 50, it is preferable that the pressing member 60 is substantially transparent.

Similar to the inflatable portion 50, a structure of the pressing member 60 may be in a shape of a bag obtained by overlapping two sheet materials made of the above-described materials and joining edge portions using a method such as fusing, adhesion, etc. As illustrated in FIG. 17, an external shape of the pressing member 60 may be a rectangle in a state of not being inflated.

As illustrated in FIG. 18, the marker 70 is provided on the outer surface side of the inflatable portion 50, that is, on a surface of the inflatable portion 50 not facing the body surface of the wrist 200. When such a marker 70 is provided in the inflatable portion 50, the inflatable portion 50 may be rather easily positioned with respect to the puncture site 220, and thus a position shift of the inflatable portion 50 is suppressed.

A shape of the marker 70 is not particularly limited. Examples of the shape include a circle, a triangle, a rectangle, etc. In the present embodiment, the shape corresponds to the rectangle.

A size of the marker 70 is not particularly limited. However, when the shape of the marker 70 is rectangular, for example, a length of a side of the rectangular marker is preferably in a range of 1 to 4 mm. When the length of the side of the rectangular marker is 5 mm or more, the size of the marker 70 becomes larger when compared to a size of the puncture site 220, and thus it is difficult to position a central portion of the inflatable portion 50 in the puncture site 220.

A material forming the marker 70 is not particularly limited. Examples of such material include an oily coloring agent such as ink, a resin kneaded with a pigment, etc.

A color of the marker 70 is not particularly limited so long as the color allows the inflatable portion 50 to be positioned in the puncture site 220. However, a green-based color is preferable. When the green-based color is adopted, it is relatively easy to visually recognize the marker 70 on blood or skin, and thus the inflatable portion 50 is more easily positioned in the puncture site 220.

In addition, the marker 70 is preferably translucent or colored transparent. In this way, the puncture site 220 may be visually recognized from an outer surface side of the marker 70.

The manner in which the marker 70 is provided at the inflatable portion 50 is not particularly limited. Examples include printing the marker 70 on the inflatable portion 50, fusing the marker 70 to the inflatable portion 50, applying an adhesive to one surface of the marker 70 to paste the marker 70 to the inflatable portion 50, etc.

The marker 70 may be provided on the inner surface side of the inflatable portion 50. In this instance, the marker 70 is preferably provided on an inner surface, etc. of the inflatable portion 50 so as not to directly come into contact with the puncture site 220.

The first injection portion 80 and the second injection portion 81 are parts for injecting a fluid into the inflatable portion 50 and the pressing member 60, respectively, and are connected to the inflatable portion 50 and the pressing member 60, respectively, as illustrated in FIG. 17.

The first injection portion 80 includes a flexible first tube 82 having a proximal portion connected to the inflatable portion 50 and a lumen communicating with an inside of the inflatable portion 50, a first bag body 84 disposed at a distal portion of the first tube 82 to communicate with the lumen of the first tube 82, and a tube-shaped first connector 86 connected to the first bag body 84. A check valve (not illustrated) is incorporated in the first connector 86.

Similar, the second injection portion 81 includes a flexible second tube 83 having a proximal portion connected to the pressing member 60 and a lumen communicating with an inside of the pressing member 60, a second bag body 85 disposed at a distal portion of the second tube 83 to communicate with the lumen of the second tube 83, and a tube-shaped second connector 87 connected to the second bag body 85. A check valve (not illustrated) may be incorporated in the second connector 87. The second tube 83 may preferably disposed on the same side as a side where the first tube 82 is disposed with respect to the band 20. In this way, it is possible to inject a fluid into the first tube 82 and the second tube 83 from the same side. For this reason, when the same syringe is used for the first tube 82 and the second tube 83, it is possible to rather easily perform an operation of inserting and withdrawing the syringe.

Figure 21:
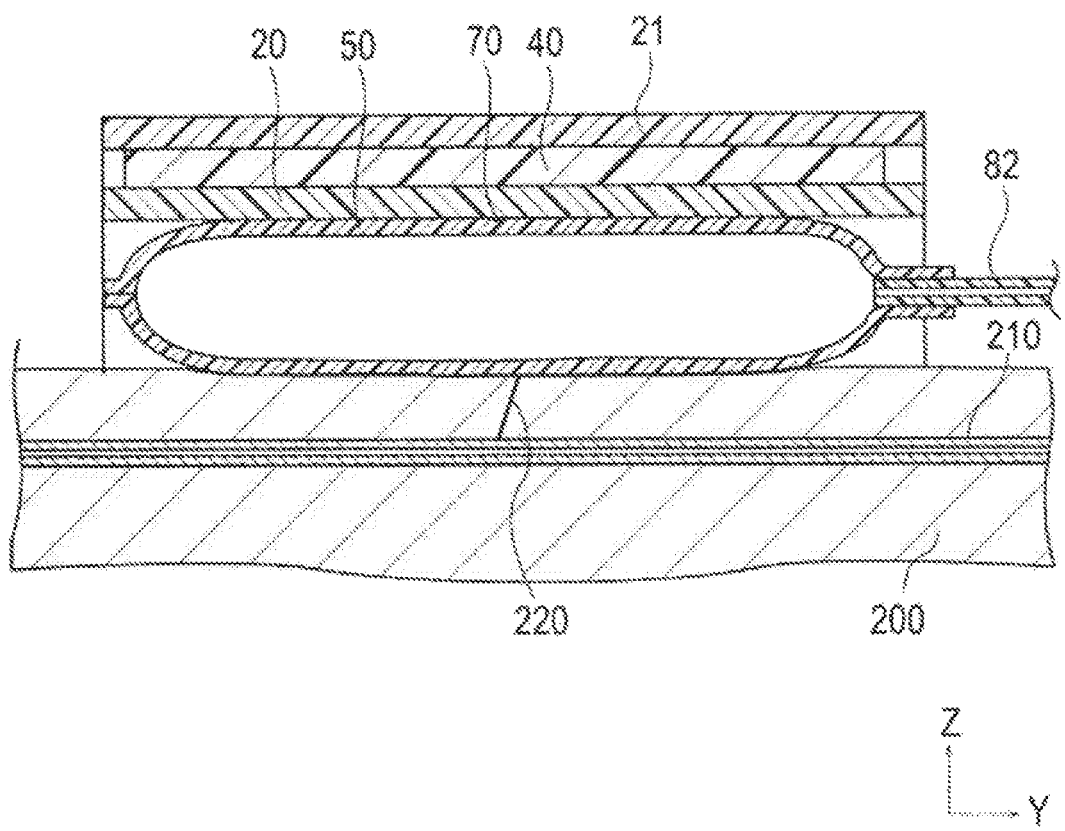
FIG. 21 is a cross-sectional view taken along the section line 21-21 of FIG. 19.
Figure 22:
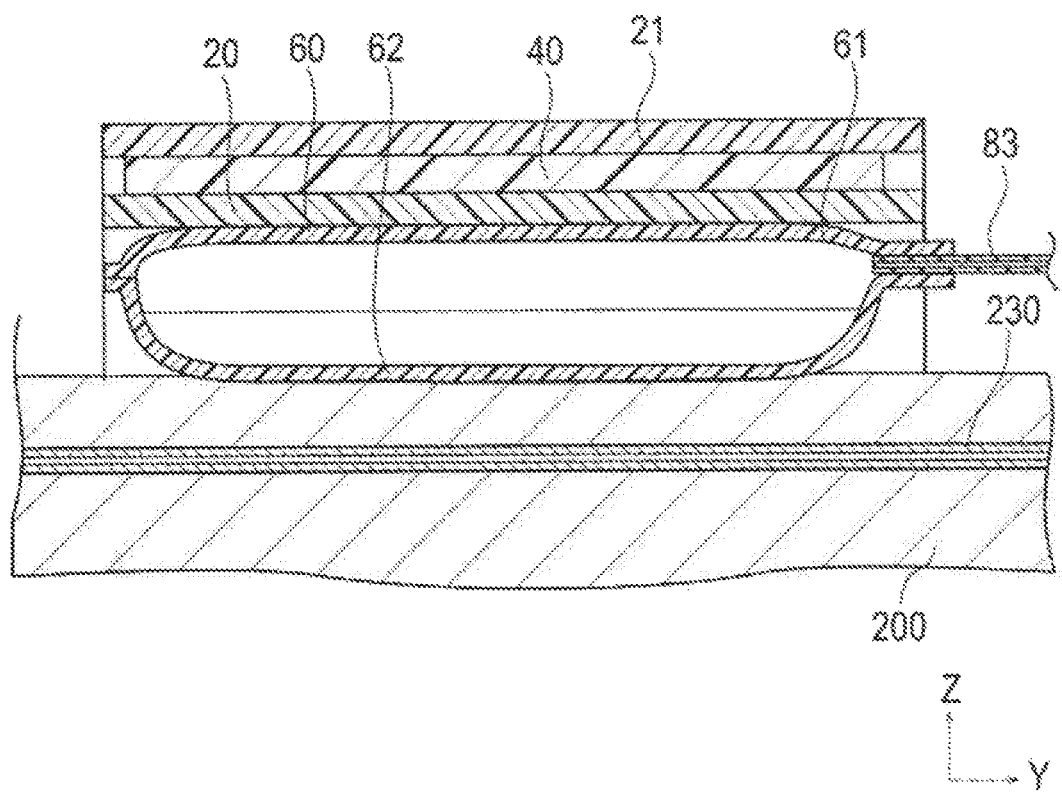
FIG. 22 is a cross-sectional view taken along the section line 22-22 of FIG. 19.

At the time of inflating (expanding) the inflatable portion 50, a tip of a syringe (not illustrated) is inserted into the first connector 86 to open the check valve, and a plunger of this syringe is pushed to inject a fluid in the syringe into the inflatable portion 50 through the first injection portion 80. When the inflatable portion 50 expands, the first bag body 84 communicating with the inflatable portion 50 through the first tube 82 also expands, and it is possible to visually confirm that the inflatable portion 50 can be pressed without leakage of the fluid. When the tip of the syringe is withdrawn from the first connector 86 after the fluid is injected into the inflatable portion 50, the check valve incorporated in the first connector 86 is closed to prevent leakage of the fluid, and an expanded state of the inflatable portion 50 is maintained. When the same operation is performed with respect to the second injection portion 81 connected to the pressing member 60, an expanded state of the pressing member 60 is maintained. In this way, as illustrated in FIG. 20 to FIG. 22, the inflatable portion 50 and the pressing member 60 inflate.

Next, a description will be given of a manner of using the hemostatic device 10 according to the present embodiment.

Before the hemostatic device 10 is mounted on the wrist 200, the inflatable portion 50 and the pressing member 60 are in a state of not being inflated. When the wrist 200 is punctured, the puncture site 220 with respect to the radial artery 210 is normally biased to a thumb side of the right hand wrist 200. Normally, the introducer sheath is indwelled in the puncture site 220. The band 20 is wrapped around the wrist 200 in which the introducer sheath is indwelled, the inflatable portion 50 and the band 20 are positioned such that the marker 70 provided in the inflatable portion 50 overlaps the puncture site 220, and the male side 31 and the female side 32 of the hook and loop fastener 30 are brought into contact with each other and joined to each other, thereby mounting the band 20 on the wrist 200.

The hemostatic device 10 may be mounted on the wrist 200 such that the first injection portion 80 and the second injection portion 81 face a downstream side of a blood flow of the radial artery 210. In this way, the first injection portion 80 and the second injection portion 81 may be operated without interfering with manipulation on the upstream side of the wrist or a device (for example, a sphygmomanometer, etc.) located on the upstream side. In addition, when the hemostatic device 10 is mounted on the right hand wrist 200 such that the first injection portion 80 and the second injection portion 81 face the downstream side, the inflatable portion 50 is located on the radial artery 210 biased to the thumb side of the wrist 200, and the pressing member 60 is located on the ulnar artery 230. In the case of the artery, the upstream side of the blood vessel refers to a direction of the blood vessel approaching a heart. In addition, the downstream side of the blood vessel refers to a direction of the blood vessel away from the heart.

After the hemostatic device 10 is mounted on the wrist 200, the syringe (not illustrated) is connected to the first connector 86 of the first injection portion 80, the fluid is injected into the inflatable portion 50 as described above, and the inflatable portion 50 is inflated to press the puncture site 220 as illustrated in FIG. 20(A) and FIG. 21. A degree of inflation of the inflatable portion 50, that is, a pressing force to the puncture site 220 located in the radial artery 210 may be rather easily adjusted depending on the case according to an injection amount of the fluid at this time.

After the inflatable portion 50 is inflated, the syringe is detached from the first connector 86. Then, the introducer sheath is withdrawn from the puncture site 220. In this way, the inflatable portion 50 maintains an inflated state, and a state of pressing the puncture site 220 is maintained.

Subsequently, the syringe is connected to the second connector 87 of the second injection portion 81, and the fluid is injected into the pressing member 60 as described above, thereby inflating the pressing member 60. A degree of inflation of the pressing member 60, that is, a pressing force to the ulnar artery 230 may be rather easily adjusted according to an injection amount of the fluid at this time. In addition, the injection amount of the fluid may be appropriately adjusted depending on the progress of hemostasis or the elapsed time.

When the inflatable portion 50 and the pressing member 60 are inflated, the curved plate 40 is separated from the body surface of the wrist 200 and hardly comes into contact with the wrist 200. In addition, when the inflatable portion 50 and the pressing member 60 are inflated after the hemostatic device 10 is mounted, inflation of the inflatable portion 50 and the pressing member 60 in a direction away from the body surface of the wrist 200 is suppressed by the curved plate 40, and a pressing force of the inflatable portion 50 and the pressing member 60 is concentrated on the wrist 200 side. For this reason, a pressing force from the inflatable portion 50 intensively acts on the vicinity of the puncture site 220, and thus the hemostatic effect may be improved.

In addition, when the inflatable portion 50 presses the radial artery 210, the ulnar artery 230 may be pressed, thereby preventing an excessive increase in the blood flow flowing to the ulnar artery 230, and suppressing a decrease in the blood flow rate of the radial artery 210. In this way, occlusion of the blood vessel may be prevented, and a decrease in the amount of the platelets, etc. may be suppressed, thereby performing hemostasis at the puncture site 220 in a relatively short time.

When hemostasis is completed, the pressing force of the inflatable portion 50 to the puncture site 220 is further reduced and the hemostatic device 10 is removed.

When hemostasis in the puncture site 220 is completed and the hemostatic device 10 is removed, the inflatable portion 50 is contracted, and then the male side 31 and the female side 32 of the hook and loop fastener 30 are peeled off or separated to remove the hemostatic device 10 from the wrist 200. The inflatable portion 50 may not be contracted when the hemostatic device 10 is removed.

As described above, the hemostatic device 10 according to the present embodiment includes the flexible band 20 that can be wrapped around the wrist 200 in which the radial artery 210 and the ulnar artery 230 run, the hook and loop fastener 30 that secures the band 20 to the wrist 200 in a wrapped state, the inflatable portion 50 connected to the band 20 and allowed to press a part of the radial artery 210 to be subjected to hemostasis by being inflated in response to injection of the fluid, and the pressing member 60 disposed at a different position from that of the inflatable portion 50 in the longitudinal direction of the band 20 and allowed to press the ulnar artery 230. The pressing member 60 includes the main body 61 and the projection 62 which is disposed on the main body 61 and may have a shape protruding with respect to the main body 61.

According to the hemostatic device 10 configured as described above, it is possible to apply a sufficient pressing force to the ulnar artery 230 by the projection 62 receiving a pressing force from the main body 61, and to adjust a pressing direction of the projection 62 by the main body 61. In this way, it is possible to restrict pressing a part other than the ulnar artery 230 such as a tendon, a nerve, etc. around the ulnar artery 230, suppress a position shift of a part in which the wrist 200 is pressed by the projection 62, and reduce occurrence of numbness or pain on the wrist 200 due to pressing over a long period of time.

In addition, the main body 61 can be inflated by being injected with a fluid, the projection 62 communicates with the main body 61 so as to inflate in response to injection of a fluid, and the projection 62 includes a part protruding with respect to the main body 61 in a state in which the main body 61 and the projection 62 inflate. In this way, the main body 61 and the projection 62 may be inflated by a single inflation operation, and thus the inflation operation is facilitated.

In addition, the length L2 of the projection 62 along the longitudinal direction of the band 20 may be shorter than the length L1 of the main body 61 along the longitudinal direction of the band 20. In this way, it is possible to apply a pressing force to an outer surface of the projection 62 over the whole band 20 in the longitudinal direction. Therefore, when the pressing member 60 is inflated, the projection 62 is held on the inner surface side of the main body 61, and a pressing direction of the projection 62 is defined based on a pressing direction of the main body 61. In this way, it is possible to prevent the projection 62 from pressing the wrist 200 in an unintended direction.

In addition, the length W2 of the projection 62 along the width direction of the band 20 (the direction of the arrow Y) may be less than or equal to the length W1 of the main body 61. In this way, since the length W2 of the projection 62 is relatively short, it is possible to narrow a range pressed by the pressing member 60. As a result, it is possible to restrict pressing a part other than the ulnar artery 230 such as a tendon, a nerve, etc. around the ulnar artery 230, and to reduce occurrence of numbness or pain on the wrist 200 due to pressing over a long period of time.

In addition, the projection 62 may have a shape continuously extending along the width direction of the band 20 (the direction of the arrow Y). In this way, a part of the projection 62 coming into contact with the wrist 200 may have a shape extending along running (direction of extent) of the ulnar artery 230. As a result, it is possible to favorably press the ulnar artery 230. For this reason, it is possible to further reduce occurrence of numbness or pain on the wrist 200 due to pressing for a long period of time.

Modification 1 of Third Embodiment

A hemostatic device 11 according to Modification 1 of the third embodiment is different from the third embodiment only in the shape of the pressing member 160, and the other aspects and configurations of the hemostatic device are substantially the same as that of the above-described third embodiment. In the description below, features that are the same or similar to those described above are identified by the same reference numerals and a detailed description of such features is not repeated.

Figure 23A:
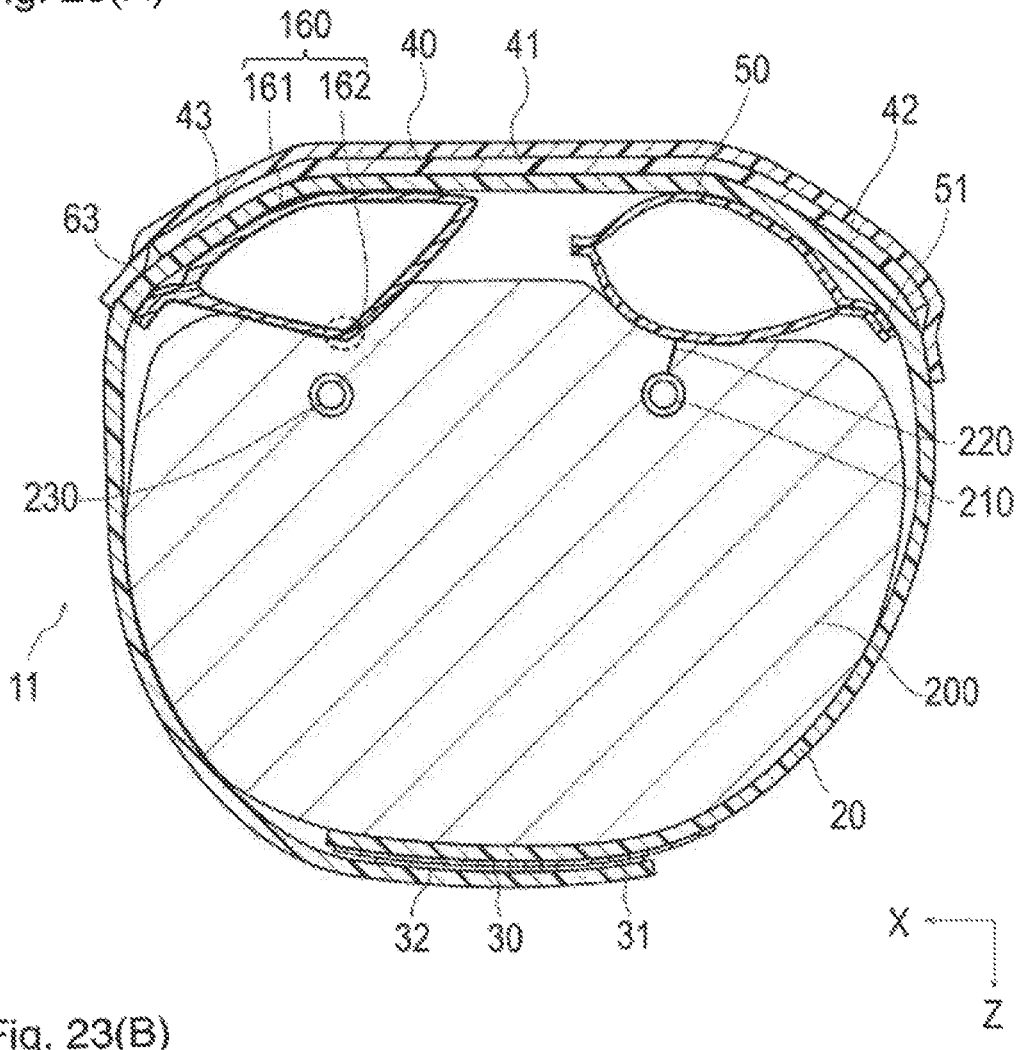
FIG. 23(A) is a cross-sectional view corresponding to FIG. 20(A), as a diagram illustrating a state of mounting a hemostatic device according to Modification 1 of the third embodiment.
Figure 23B:
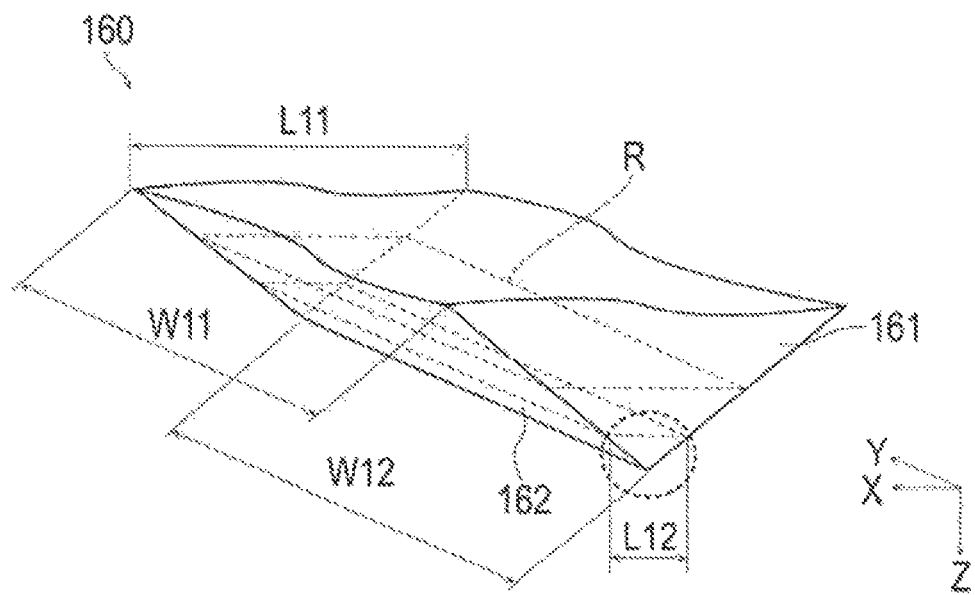
FIG. 23(B) is a perspective view schematically illustrating a pressing member.

Similar to the third embodiment, a pressing member 160 includes a main body 161 forming a main part and a projection 162 inflated and deformed together with the main body 161 in response to injection of a fluid to protrude from a part of a surface on an inner surface side of the main body 161 as shown in FIG. 23(A) and FIG. 23(B). The main body 161 is made of the same material as that of the projection 162 and integrally formed.

A cross-sectional shape of the pressing member 160 according to Modification 1 in an inflated state may be a triangle as illustrated in FIG. 23(A), and a three-dimensional shape of the pressing member 160 may be a shape similar to a triangular prism as illustrated in FIG. 23(B). The projection 162 is formed by a tapered distal end having a triangular shape and a peripheral portion (a distal portion) (a part surrounded by a broken line of FIG. 23(A)), and may have a shape continuously extending along the width direction of the band 20 (the direction of the arrow Y). For this reason, when the hemostatic device 11 is mounted on the wrist 200, a part of the pressing member 160 coming into contact with the wrist may have a shape extending along running (direction of extent) of the ulnar artery 230. Therefore, it is possible to favorably press the ulnar artery 230 by the pressing member 160, and to reduce a press range of a part (a tendon, a nerve, etc.) other than the ulnar artery 230. As a result, it is possible to reduce occurrence of numbness or pain on the wrist 200 at the time of mounting the hemostatic device 11.

Further, as illustrated in FIG. 23(B), similar to the third embodiment, a length L12 of the projection 162 along the longitudinal direction of the band 20 may be shorter than a length L11 of the main body 161 along the longitudinal direction of the band 20. In addition, a length W12 of the projection 162 along the width direction of the band 20 may be less than or equal to a length W11 of the main body 161.

As illustrated in FIG. 23(A), the pressing member 160 may be configured such that a length of an outer periphery R gradually shortens from the outer surface side toward the inner surface side of the band 20 (a direction of the arrow Z) at the time of being inflated and deformed. Here, the outer periphery R refers to a periphery of a Z (arrow Z) axis of the pressing member 160 as indicated by a broken line in FIG. 23(B).

According to the hemostatic device 11 according to Modification 1 of the third embodiment, the pressing member 160 may have a shape in which a length of the outer periphery R shortens from the outer surface side toward the inner surface side of the band 20 (the direction of the arrow Z) at the time of being inflated and deformed. In this way, on the outer surface side of the band 20, the outer periphery R of the pressing member 160 is relatively large, that is, an area is large in plan view in the direction of the arrow Z. Therefore, an area in which the pressing member 160 comes into contact with the inner surface of the band 20 on the outer surface side correspondingly increases. In this way, a securing force of the pressing member 160 by the band 20 increases. As a result, the pressing member 160 is more stable at the time of mounting on the wrist 200, and thus it is possible to prevent a position shift of a part in which the wrist 200 is pressed by the pressing member 160.

Modification 2 of Third Embodiment

Figure 25A:
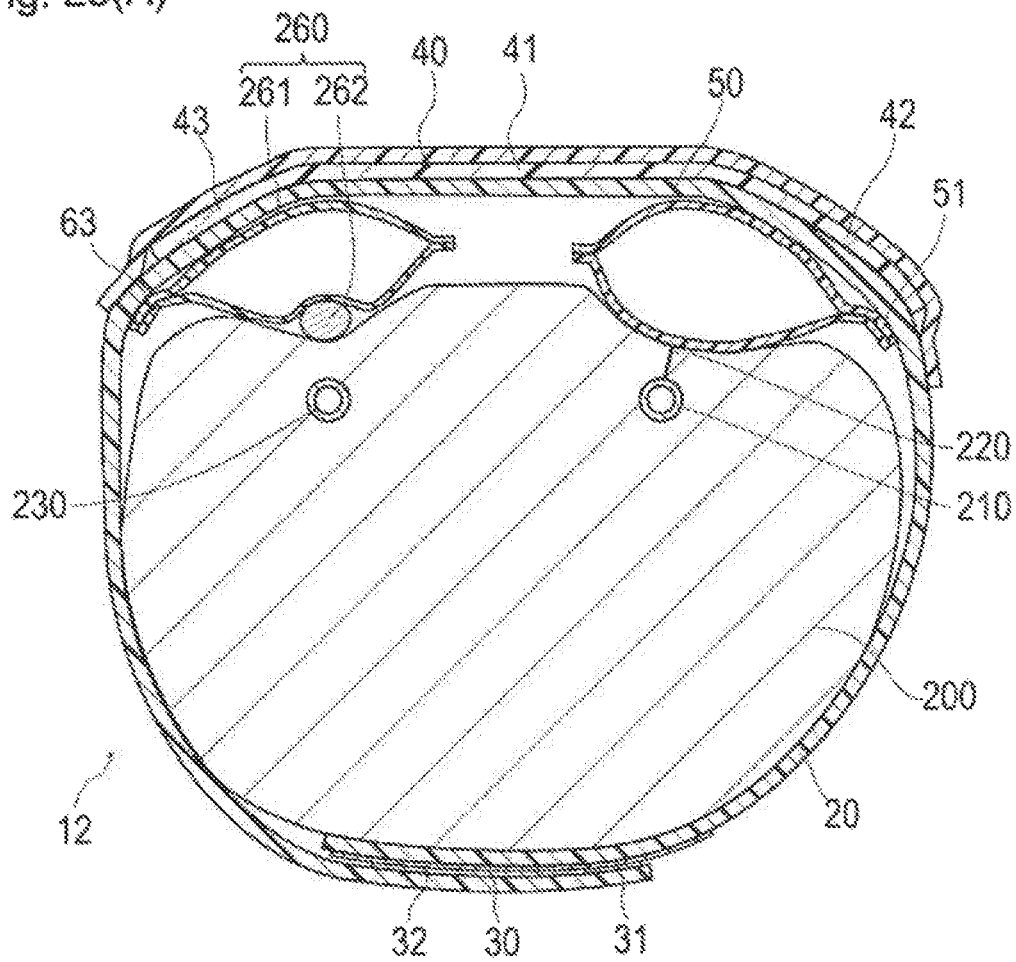
FIG. 25(A) is a cross-sectional view corresponding to FIG. 20(A), as a diagram illustrating a state of mounting a hemostatic device according to Modification 2 of the third embodiment.
Figure 25B:
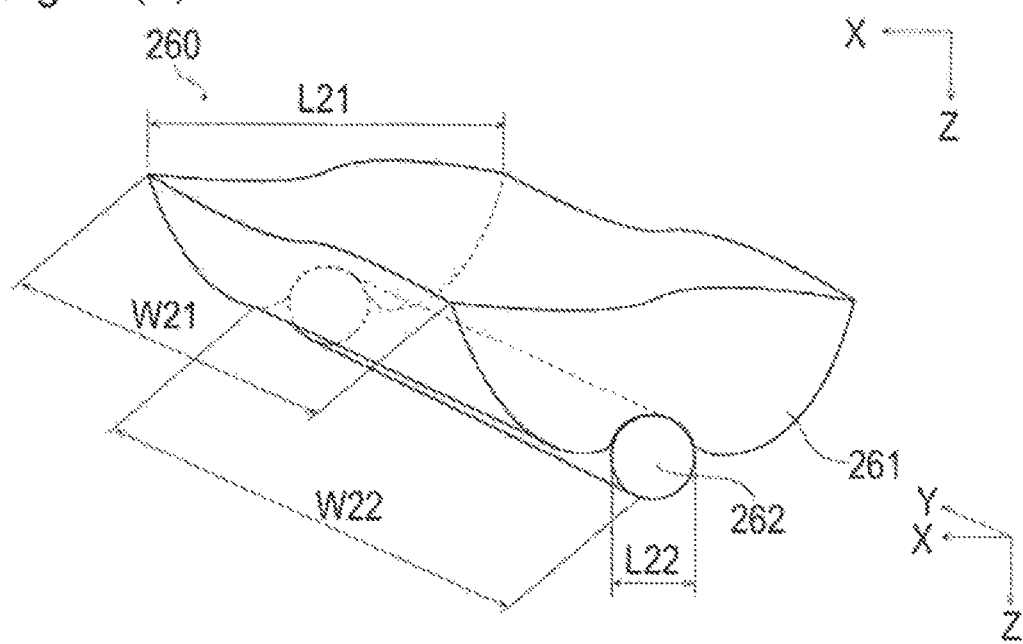
FIG. 25(B) is a perspective view schematically illustrating a pressing member.

In a hemostatic device 12 according to Modification 2 of the third embodiment, as illustrated in FIG. 24, FIG. 25(A), and FIG. 25(B), a main body 261 and a projection 262 included in a pressing member 260 are configured as separate members. The other aspects and configurations are substantially the same as that of the above-described third embodiment. In the description below, features that are the same or similar to those described above are identified by the same reference numerals and a detailed description of such features is not repeated.

As illustrated in FIG. 25(A), the main body 261 may be made of a flexible material, and presses the projection 262 by inflating in response to injection of a fluid.

The projection 262 may be made of a harder material than the material forming the main body 261, and presses the ulnar artery 230 by receiving a pressing force from the main body 261. In the present embodiment, as illustrated in FIG. 25(B), the projection 262 may have a circular cross section and may have a shape continuously extending along the width direction of the band 20 (a direction of an arrow Y). That is, the projection 262 may be formed by a cylindrical rod-shaped member. The projection 262 may be disposed on a surface (outer surface) of the main body 261 on an inner surface side of the main body 261. The projection 262 may be fixed to the main body 261 by an adhesive, an adhesive tape, etc.

As illustrated in FIG. 24, similar to the third embodiment, a length L22 of the projection 262 along the longitudinal direction of the band 20 may be shorter than a length L21 of the main body 261 along the longitudinal direction of the band 20. In addition, as illustrated in FIG. 25(B), a length W22 of the projection 262 along the width direction of the band 20 (the direction of the arrow Y) may be less than or equal to a length W21 of the main body 261. That is, the main body 261 may be disposed to cover a surface of the projection 262 on the outer surface side between the projection 262 and the band 20. In this way, when the main body 261 is inflated, the projection 262 is held on the inner surface side of the main body 261, and it is possible to adjust a direction in which the wrist 200 is pressed by the projection 262.

A constituent material forming the main body 261 is not particularly limited as long as the material is a flexible material. For example, it is possible to use the same material as the constituent material forming the band 20 mentioned above.

A constituent material forming the projection 262 is not particularly limited as long as the material is harder than that material of the main body 261. For example, it is possible to use an elastic material such as a sponge-like substance, an aggregate of fibers such as cotton, metal, a rigid material such as plastic, or a combination thereof.

As described above, according to the hemostatic device 12 according to Modification 2 of the third embodiment, the main body 261 may be inflated by being injected with a fluid, and the projection 262 may be made of a harder material than that of the main body 261 and attached to an outer surface of the main body 261. In this way, a shape of the projection 262 rarely changes due to an inflation degree of the main body 261. Therefore, a change of a range in which the wrist 200 is pressed by the projection 262 is relatively small, and thus it is possible to suppress a variation in the pressing range for each manipulation. As a result, it is possible to restrict pressing a part other than the ulnar artery 230 such as a tendon, a nerve, etc. around the ulnar artery 230, and to reduce occurrence of numbness or pain on the wrist 200 due to pressing over a long period of time.

The hemostatic devices according to the third embodiment and the modifications of the third embodiment described above may be appropriately modified while still being within the scope of the description in the claims.

For example, each portion included in the hemostatic device may be replaced with a portion having an arbitrary configuration capable of exerting the same function. In addition, an arbitrary component may be added.

In addition, the invention is not limited to the hemostatic device used by being mounted on the wrist, and is applicable to a hemostatic device used by being mounted on any part of the arm in which the radial artery and the ulnar artery run.

In addition, an external shape of the inflatable portion is not limited to a rectangle in a state of not being inflated. For example, the external shape may correspond to a circle, an ellipse, and a polygon such as a pentagon. In this case, a central portion of the inflatable portion corresponds to a center of a shape forming the external shape of the inflatable portion.

In addition, the marker may not be provided in the inflatable portion, and may be provided in the band or the curved plate. In addition, the marker is more preferably provided to overlap the central portion of the inflatable portion.

In addition, in the third embodiment and Modification 1 of the third embodiment, a description has been given of a configuration in which the pressing member can be inflated by being injected with a fluid. In Modification 2 of the third embodiment, a description has been given of a configuration in which the pressing member is based on the main body that can be inflated by being injected with a fluid and the projection made of the harder material than that of the main body. The pressing member according to the invention is not limited to these configurations as long as the ulnar artery can be pressed. For example, the whole pressing member may be formed by a sponge-like substance, an elastic material, etc. Alternatively, it is possible to have a configuration including a main body formed by a sponge-like substance, an elastic material, etc. and a projection that can be inflated by being injected with a fluid.

The detailed description above describes embodiments of a hemostatic device representing examples of the inventive hemostatic device disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A hemostatic device comprising:
    a flexible band configured to be wrapped around an arm in which a radial artery and an ulnar artery are located, the flexible band possessing a longitudinal extent that extends in a longitudinal direction;
    a securing portion that secures the flexible band on the arm while the flexible band is wrapped around the arm in a wrapped state;
    a support plate that is more rigid than the flexible band, the support plate being mounted on the flexible band so that the support plate and the flexible band move together as a unit;
    an inflatable member connected to the flexible band and expandable upon being inflated in response to introducing a first fluid into an interior of the inflatable member to press a part of the radial artery to be subjected to hemostasis;
    a pressing member disposed at a position spaced from a position of the inflatable member in the longitudinal direction of the flexible band to press the ulnar artery;
    the pressing member possessing a length along the longitudinal direction of the flexible band that is shorter than a width of the pressing member along a direction orthogonal to the longitudinal direction of the flexible band;
    the inflatable member possessing a first surface disposed on a side that will face the arm when the flexible band is in the wrapped state and a second surface disposed on a side facing the flexible band;
    the pressing member including a third surface disposed on the side that will face the arm when the flexible band is in the wrapped state and a fourth surface disposed on the side facing the flexible band;
    the pressing member is inflatable to outwardly expand by being injected with a second fluid;
    a volume of the inflatable member in an inflated state is larger than a volume of the pressing member in an inflated state;
    a length of a perpendicular line from the support plate to the first surface is longer than a length of a perpendicular line from the support plate to the third surface when the inflatable member and the pressing member are both in the inflated states in a state in which at least a part of the second surface of the inflatable member and at least a part of the fourth surface of the pressing member are in contact with a portion of the flexible band in which the support plate is disposed;
    the support plate includes an inner surface that faces toward the arm when the flexible band is wrapped around the arm in the wrapped state, the inner surface of the support plate including a center inner surface portion, a first curved inner surface portion and a second curved inner surface portion, the center inner surface portion being positioned between the first and second inner surface portions along the longitudinal direction of the flexible band, and the first curved inner surface portion having a length along a longitudinal direction of the support plate longer than a length of the second curved inner surface portion along the longitudinal direction of the support plate such that the support plate has a longitudinal cross-sectional shape that is asymmetrical.

2. The hemostatic device according to claim 1, wherein the flexible band possesses a width in the direction orthogonal to the longitudinal direction of the flexible band, the width of the pressing member being less than or equal to the width of the flexible band.

3. The hemostatic device according to claim 1, wherein the inflatable member possesses a length in the longitudinal direction of the flexible band, the length of the pressing member being shorter than the length of the inflatable member.

4. The hemostatic device according to claim 1, further comprising a first tube in communication with the interior of the inflatable member to introduce the first fluid into the interior of the inflatable member, and a second tube in communication with an interior of the pressing member to introduce the second fluid into the interior of the pressing member.

5. The hemostatic device according to claim 1, wherein the inflatable member overlaps with the first curved inner surface portion and the pressing member overlaps with the second curved inner surface portion, the center inner surface portion being exposed between the pressing member and the inflatable member.

6. The hemostatic device according to claim 1, wherein the inflatable member is connected to the flexible band at a connection, the connection being located so that during use of the hemostatic device, the inflatable member is positioned between the center inner surface portion and the connection.

7. A hemostatic device comprising:
    a flexible band configured to be wrapped around an arm in which a radial artery and an ulnar artery are located, the flexible band possessing a longitudinal extent that extends in a longitudinal direction, the flexible band being made of a first material;

a securing portion that secures the flexible band on the arm while the flexible band is wrapped around the arm in a wrapped state;

a support plate held by the flexible band and made of a second material more rigid than the first material from which the flexible band is made;

an inflatable member connected to the flexible band and expandable upon being inflated in response to introducing a first fluid into an interior of the inflatable member to press a part of the radial artery to be subjected to hemostasis;

a pressing member disposed at a position spaced from a position of the inflatable member in the longitudinal direction of the flexible band and configured to press the ulnar artery;

the inflatable member possessing a first surface disposed on a side that will face the arm when the flexible band is in the wrapped state and a second surface disposed on a side facing the band;

the pressing member including a third surface disposed on the side that will face the arm when the flexible band is in the wrapped state and a fourth surface disposed on the side facing the band;

the pressing member is inflatable to outwardly expand by being injected with a second fluid;

a volume of the inflatable member in an inflated state is larger than a volume of the pressing member in an inflated state;

a length of a perpendicular line from the support plate to the first surface is longer than a length of a perpendicular line from the support plate to the third surface when the inflatable member and the pressing member are both in the inflated states in a state in which at least a part of the second surface of the inflatable member and at least a part of the fourth surface of the pressing member are in contact with a portion of the band in which the support plate is disposed;

the support plate includes an inner surface that faces toward the arm when the flexible band is wrapped around the arm in the wrapped state, the inner surface of the support plate including a center inner surface portion, a first curved inner surface portion and a second curved inner surface portion, the center inner surface portion being positioned between the first and second curved inner surface portions along the longitudinal direction of the flexible band, and the first curved inner surface portion having a length along a longitudinal direction of the support plate longer than a length of the second curved inner surface portion along the longitudinal direction of the support plate such that the support plate has a longitudinal cross-sectional shape that is asymmetrical.

8. The hemostatic device according to claim 7, wherein a surface area of the first surface of the inflatable member in the inflated state is larger than a surface area of the third surface of the pressing member.

9. The hemostatic device according to claim 7, wherein a length of the pressing member along the longitudinal direction of the band is shorter than a length of the inflatable member along the longitudinal direction of the band.

10. The hemostatic device according to claim 7, wherein the inflatable member overlaps with the first curved inner surface portion and the pressing member overlaps with the second curved inner surface portion, the center inner surface portion being exposed between the pressing member and the inflatable member.

11. The hemostatic device according to claim 7, wherein the inflatable member is connected to the flexible band at a connection, the connection being located so that during use of the hemostatic device, the inflatable member is positioned between the center inner surface portion and the connection.

* * * * *